United States Patent
Wersland et al.

(10) Patent No.: US 10,857,064 B2
(45) Date of Patent: *Dec. 8, 2020

(54) PERCUSSIVE THERAPY DEVICE

(71) Applicant: Theragun, Inc., Beverly Hills, CA (US)

(72) Inventors: Jason Wersland, Manhattan Beach, CA (US); Benjamin Nazarian, Beverly Hills, CA (US); Jaime Sanchez Solana, Los Angeles, CA (US); Eduardo Merino, Beverly Hills, CA (US)

(73) Assignee: THERAGUN, INC., Beverly Hills, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 16/869,402

(22) Filed: May 7, 2020

(65) Prior Publication Data

US 2020/0261307 A1    Aug. 20, 2020

Related U.S. Application Data

(63) Continuation-in-part of application No. 16/796,143, filed on Feb. 20, 2020, and a continuation-in-part of
(Continued)

(51) Int. Cl.
*A61H 23/00* (2006.01)
*A61H 23/02* (2006.01)
(Continued)

(52) U.S. Cl.
CPC .......... *A61H 23/006* (2013.01); *A61H 1/008* (2013.01); *A61H 23/00* (2013.01);
(Continued)

(58) Field of Classification Search
CPC .......... A61H 1/00; A61H 1/006; A61H 1/008; A61H 23/00; A61H 23/004; A61H 23/006;
(Continued)

(56) References Cited

U.S. PATENT DOCUMENTS

| 3,172,675 A | 3/1965 | Gonzalez |
| 3,545,301 A | 12/1970 | Richter |

(Continued)

FOREIGN PATENT DOCUMENTS

| JP | 1990019157 | 1/1990 |
| JP | 1995051393 | 2/1995 |

(Continued)

OTHER PUBLICATIONS

PCT/US2016/038326 International Search Report & Written Opinion dated Sep. 1, 2016.

(Continued)

*Primary Examiner* — Colin W Stuart
(74) *Attorney, Agent, or Firm* — Jeffer Mangels Butler & Mitchell LLP; Brennan C. Swain, Esq.

(57) ABSTRACT

A percussive therapy device that includes a housing, an electrical source, a motor positioned in the housing, a switch for activating the motor, and a push rod assembly operatively connected to the motor and configured to reciprocate in response to activation of the motor. The housing includes first, second and third handle portions and a head portion that cooperate to define a handle opening. The first handle portion defines a first axis, the second handle portion defines a second axis and the third handle portion defines a third axis and the first, second and third axes cooperate to form a triangle. The motor is positioned in the head portion of the housing, and at least a portion of the push rod assembly extends outside of the head portion.

23 Claims, 50 Drawing Sheets

Related U.S. Application Data application No. 16/869,402, filed on May 7, 2020, now Pat. No. 10,702,448.

(60) Provisional application No. 62/844,424, filed on May 7, 2019, provisional application No. 62/899,098, filed on Sep. 11, 2019, provisional application No. 62/912,392, filed on Oct. 8, 2019, provisional application No. 62/785,151, filed on Dec. 26, 2018.

(51) Int. Cl.
| | |
|---|---|
| *A61H 1/00* | (2006.01) |
| *B27B 19/00* | (2006.01) |
| *B23D 51/16* | (2006.01) |
| *B27B 19/02* | (2006.01) |
| *B23D 49/00* | (2006.01) |
| *B23D 49/10* | (2006.01) |
| *A61B 17/14* | (2006.01) |

(52) U.S. Cl.
CPC ........ *A61H 23/0254* (2013.01); *A61B 17/142* (2016.11); *A61H 2023/029* (2013.01); *A61H 2201/0153* (2013.01); *A61H 2201/0165* (2013.01); *A61H 2201/12* (2013.01); *A61H 2201/1207* (2013.01); *A61H 2201/1215* (2013.01); *A61H 2201/14* (2013.01); *A61H 2201/149* (2013.01); *A61H 2201/1481* (2013.01); *A61H 2201/1664* (2013.01); *A61H 2201/5025* (2013.01); *A61H 2201/5035* (2013.01); *A61H 2201/5046* (2013.01); *A61H 2201/5097* (2013.01); *B23D 49/007* (2013.01); *B23D 49/10* (2013.01); *B23D 51/16* (2013.01); *B27B 19/00* (2013.01); *B27B 19/002* (2013.01); *B27B 19/02* (2013.01)

(58) Field of Classification Search
CPC ................ A61H 23/02; A61H 23/0218; A61H 23/0254; A61H 23/0263; A61H 23/04; A61H 23/06; A61H 2023/002; A61H 2023/0209; A61H 2023/0272; A61H 2023/0281; A61H 2023/029; A61H 39/00; A61H 39/002; A61H 39/007; A61H 39/04; A61H 2201/0165; A61H 2201/12; A61H 2201/1207; A61H 2201/1215; A61H 2201/1223; A61H 2201/123; A61H 2201/1238; A61H 2201/14; A61H 2201/1409; A61H 2201/1418; A61H 2201/1481; A61H 2201/149; A61H 2201/1664; B23D 51/16; B23D 49/162; B23D 49/165; B23D 49/00; B23D 49/007; B23D 49/008; B23D 49/10; B23D 49/16; B23D 49/167; B26D 7/2621; B26D 7/2614; B26D 5/14; A61B 17/148; A61B 17/142; A61B 17/14; A61B 17/144; B27B 19/00; B27B 19/002; B27B 19/006; B27B 19/09; B27B 19/02; B27B 11/06
USPC .... 83/615, 623, 632, 626, 427; 30/392, 393, 30/394, 182, 208, 241, 217–220, 242; 173/49, 114, 122, 205, 227/131; D08/8, D08/61, 64; 144/121, 122, 147; 125/16.01; 76/31, 36; 601/97, 107
See application file for complete search history.

(56) References Cited

U.S. PATENT DOCUMENTS

| | | | |
|---|---|---|---|
| 3,626,934 A | 12/1971 | Andis | |
| 3,942,251 A | 3/1976 | Grithes | |
| 4,150,668 A | 4/1979 | Johnston | |
| 4,173,217 A | 11/1979 | Johnston | |
| 4,549,535 A | 10/1985 | Wing | |
| 4,566,442 A | 1/1986 | Mabuchi | |
| 4,730,605 A | 3/1988 | Noble et al. | |
| 5,085,207 A | 2/1992 | Fiore | |
| 5,212,887 A | 5/1993 | Farmerie | |
| 5,417,644 A | 5/1995 | Lee et al. | |
| 5,569,168 A | 10/1996 | Hartwig | |
| 5,573,500 A | 11/1996 | Katsunuma | |
| 5,951,501 A | 9/1999 | Griner | |
| 6,228,042 B1 | 5/2001 | Dungan | |
| 6,663,657 B1 | 12/2003 | Miller | |
| 6,682,496 B1 | 1/2004 | Pivaroff | |
| 7,041,072 B2 * | 5/2006 | Calvert ................ | A61H 7/001 128/898 |
| 7,927,259 B1 | 4/2011 | Rix | |
| 7,996,996 B2 | 8/2011 | Hirabayashi | |
| 8,342,187 B2 | 1/2013 | Kalman | |
| 8,951,216 B2 | 2/2015 | Yoo et al. | |
| 10,314,762 B1 | 6/2019 | Marton | |
| 10,357,425 B2 * | 7/2019 | Wersland ............... | A61H 1/008 |
| 10,702,448 B2 * | 7/2020 | Wersland ........... | A61H 15/0085 |
| 2001/0016697 A1 | 8/2001 | Gorsen | |
| 2003/0009116 A1 | 1/2003 | Luettgen | |
| 2003/0094356 A1 | 5/2003 | Waldron | |
| 2003/0144615 A1 | 7/2003 | Lin | |
| 2003/0195443 A1 | 10/2003 | Miller | |
| 2005/0126018 A1 * | 6/2005 | Haas ...................... | B23D 51/16 30/394 |
| 2005/0252011 A1 * | 11/2005 | Neumeier ............. | B23D 51/02 30/371 |
| 2006/0025710 A1 | 2/2006 | Schulz | |
| 2006/0123941 A1 | 6/2006 | Wadge | |
| 2006/0192527 A1 | 8/2006 | Kageler | |
| 2007/0144310 A1 | 6/2007 | Pozgay | |
| 2007/0150004 A1 | 6/2007 | Colloca | |
| 2008/0103419 A1 | 5/2008 | Adamson | |
| 2010/0162579 A1 * | 7/2010 | Naughton ............. | B23D 49/16 30/392 |
| 2012/0253245 A1 | 10/2012 | Stanbridge | |
| 2013/0014968 A1 * | 1/2013 | Kehoe ....................... | B25F 5/02 173/216 |
| 2013/0133210 A1 | 5/2013 | Weir | |
| 2013/0138023 A1 | 5/2013 | Lerro | |
| 2013/0261516 A1 | 10/2013 | Cilea | |
| 2013/0281897 A1 | 10/2013 | Hoffmann | |
| 2014/0180331 A1 | 6/2014 | Turner | |
| 2015/0005682 A1 | 1/2015 | Danby | |
| 2015/0119771 A1 * | 4/2015 | Roberts ................ | A61N 5/0619 601/135 |
| 2015/0148592 A1 | 5/2015 | Kanbar | |
| 2015/0375315 A1 | 12/2015 | Ukai | |
| 2017/0027798 A1 * | 2/2017 | Wersland ............... | A61H 1/008 |
| 2017/0156974 A1 * | 6/2017 | Griner .................. | A61H 23/006 |
| 2017/0304145 A1 * | 10/2017 | Pepe .................... | A61H 23/006 |
| 2018/0236572 A1 | 8/2018 | Ukai | |
| 2018/0288160 A1 * | 10/2018 | Paul ...................... | H04L 67/125 |
| 2019/0175434 A1 * | 6/2019 | Zhang .................. | A61H 23/006 |

FOREIGN PATENT DOCUMENTS

| | | |
|---|---|---|
| JP | 003077837 | 6/2001 |
| JP | 2005204777 | 4/2005 |
| JP | 2010534110 | 11/2010 |
| KR | 101123926 | 4/2012 |
| WO | 2009014727 | 1/2009 |

(56) References Cited

FOREIGN PATENT DOCUMENTS

WO       2014118596       8/2014
WO       2015038005       3/2015

OTHER PUBLICATIONS

PCT/US2018/022426 International Search Report & Written Opinion dated May 31, 2018.
AU 2016284030 Examination Report dated May 7, 2018.
JP2018-517683 Office Action received Oct. 25, 2018.
CA 2990178 Office Action received Oct. 25, 2018.
Worx Trans4mer "Safety and Operating Manual Original Instructions" for 12V Li-Ion Multi-purpose saw, WX540, WX540.3, WX540.9, 2013.
Rachel [no family name indicated], "Jigsaw Massager", Apr. 18, 2010 (https://web.archive.org/web/20100418041422/http://www.instructables.com/id/Jigsaw-Massager/).
Rockwell Trans4mer Operating Manual for Multi-purpose saw, Model RK2516/RK2516K, 2011.

* cited by examiner

FIG. 44

| | PROTOCOL 1 | | | |
|---|---|---|---|---|
| STEP | 1 | 2 | 3 | 4 |
| TIME(M) | 0:30 | 0:15 | 0:30 | 0:45 |
| SPEED (RPM) | 1550 | 2100 | 2200 | 2400 |
| AMPLITUDE | 2 | 3 | 1 | 4 |
| ATTACHMENT | DAMPENER | SMALL BALL | DAMPENER | LARGE BALL |
| FORCE | 1 | 3 | 3 | 2 |
| TEMPERATURE (°C) | 21 | 26 | 29 | 32 |
| GRIP | 1 | 1 | 1 | 1 |

PROTOCOL: SHIN SPLINTS

| STEP | 1 | 2 | 3 | 4 |
|---|---|---|---|---|
| TIME(M) | 1:00 | 1:00 | 1:00 | 1:00 |
| SPEED (RPM) | 1500 | 1500 | 2000 | 2000 |
| AMPLITUDE | 1 | 1 | 3 | 3 |
| ATTACHMENT | DAMPENER | DAMPENER | DAMPENER | DAMPENER |
| FORCE | 2 | 2 | 3 | 3 |
| TEMPERATURE (°C) | 21 | 21 | 24 | 24 |
| GRIP | REVERSE | REVERSE | BASE | BASE |
| ARM POSITION | 1 | 1 | 1 | 1 |
| BODY PART | R. SHIN | L. SHIN | R. CALF | L. CALF |

FIG. 45

PERCUSSIVE THERAPY DEVICE

CROSS-REFERENCE TO RELATED APPLICATIONS

This application is a continuation-in-part of U.S. patent application Ser. No. 16/796,143, filed Feb. 20, 2020, which claims the benefit of U.S. Provisional Application No. 62/844,424, filed May 7, 2019, U.S. Provisional Application No. 62/899,098, filed Sep. 11, 2019 and U.S. Provisional Application No. 62/912,392, filed Oct. 8, 2019. This application is also a continuation-in-part of U.S. patent application Ser. No. 16/675,772, filed Nov. 6, 2019, which claims the benefit of U.S. Provisional Application No. 62/785,151, filed on Dec. 26, 2018. All applications listed above are incorporated by reference herein in their entireties.

FIELD OF THE INVENTION

The present invention relates generally to massage devices and more particularly to a percussive therapy device that provides reciprocating motion.

BACKGROUND OF THE INVENTION

Massage devices often provide ineffective massages that are superficial and do not provide any real benefit. Accordingly, there is a need for an improved massage device. Furthermore, percussive massage devices are often used in an ineffective manner. Accordingly, there is a need for a percussive therapy device to be automated to provide effective massage or recovery.

SUMMARY OF THE PREFERRED EMBODIMENTS

In accordance with a first aspect of the present invention there is provided a percussive therapy or percussive massage device that includes a housing, an electrical source, a motor positioned in the housing, a switch for activating the motor, and a routine controller configured to initiate a protocol configured to apply at least one output of the percussive therapy device in response to user input, and initiate at least one step of the protocol in which the percussive therapy device is applied in accordance with the at least one output. It will be appreciated that the terms percussive massage device and percussive therapy device are used interchangeably throughout. The terms are synonymous and generally have the same meaning. Commercial embodiments of the applicant's devices are generally being called percussive therapy devices in the market and therefore this term is used therein.

In a preferred embodiment, the at least one output comprises one or more of a time period the percussive therapy device is activated (either automatically or by the user turning it on and off via a prompt), a speed of an attachment of the percussive therapy device (either automatically or by the user switching from one speed to another via a prompt), a force applied by the attachment (by the user using the device), an amplitude of the attachment, and a temperature of the attachment.

In a preferred embodiment, the percussive therapy device includes a force meter configured to monitor and display a force applied by an attachment of the percussive therapy device. The display of the force is provided to a user and configured so that the user may adjust the force to correspond to a target force (which may be defined to include a target force range) to be applied during the at least one step of the protocol.

In a preferred embodiment, the percussive therapy device includes or is configured to communicated with an application (software application or app) configured to provide a user interface (e.g., on a user mobile device such as a phone or tablet). Preferably, the percussive therapy device includes a touch screen configured to provide or that does provide a user interface. In a preferred embodiment, a user is prompted to use a specified grip of the percussive therapy device (e.g., via the app visually, audibly or haptically, the touch screen on the percussive therapy device visually, audibly or haptically or via another screen or audible prompt).

In a preferred embodiment, a user is prompted (e.g., visually, audibly or haptically) to apply an attachment of the percussive therapy device to a specified body part. Preferably, the user is prompted (e.g., visually, audibly or haptically) to set an arm position of the percussive therapy device. The percussive therapy generally wherein a user is prompted through at least one of haptic feedback, sound, visual representation (e.g., a picture, graphic, etc.) and text during the at least one step to apply the at least one output. In a preferred embodiment, the user is prompted to move the attachment from a start point to an end point (e.g., visually, audibly or haptically) on a specified body part during the at least one step of the protocol.

In accordance with another aspect of the present invention there is provided a method of executing a routine for a percussive therapy device. The method includes initiating a protocol configured to apply at least one output of the percussive therapy device in response to user input; and executing at least one step of the protocol in which the percussive therapy device is applied in accordance with the at least one output. In a preferred embodiment, the at least one output includes one or more of a specified time period the percussive therapy device is activated (either automatically or by the user), a speed of an attachment of the percussive therapy device, a force of the attachment, an amplitude of the attachment, a type of attachment, a temperature of the attachment, an arm position of the percussive therapy device, and a grip of the percussive therapy device.

In a preferred embodiment, the method includes monitoring a force being applied by an attachment of the percussive therapy device; and displaying the force to a user. Preferably, the force is configured to be displayed to the user so that the user may adjust the force to correspond to a target force (which may be a range) predetermined by the at least one step of the protocol. Preferably, the user is prompted to apply one or more of the at least one output during the at least one step of the protocol. In a preferred embodiment, the user input initiates the protocol via at least one of an application interface and a touch screen. In a preferred embodiment, the protocol is configured to provide therapeutic effect to one or more body parts of a user.

In accordance with another aspect of the present invention there is provided a method of executing a routine for a percussive therapy device that includes initiating a protocol configured to apply at least one output of the percussive therapy device in response to user input, and initiating at least one step of the protocol in which the percussive therapy device is applied in accordance with the at least one output. The at least one output comprises a time period the percussive therapy device is activated, a speed of an attachment of the percussive therapy device, an amplitude of the attachment, a force applied by the attachment, and a temperature applied by the attachment. The percussive therapy device is configured to provide a prompt to use a specified grip of the percussive therapy device and apply the attachment to a specified body part upon initiating the protocol, monitoring a measured force being applied by the attachment, and displaying the measured force to a user, wherein the measured force is configured to be displayed to the user so that the user may adjust an applied force to correspond to a target force predetermined by the at least one step of the protocol.

In a preferred embodiment, the user is prompted to set an arm position of the percussive therapy device, and/or the user is prompted to apply the attachment to a new specified body part during the at least one step of the protocol, and/or the user is prompted to affix a new attachment to the percussive therapy device during the at least one step of the protocol, and/or the user is prompted to move the attachment from one predetermined point of a body part to a second predetermined body part during the at least one step of the protocol.

In accordance with another aspect of the present invention there is provided a percussive therapy device that includes a housing, an electrical source, a motor positioned in the housing, a switch for activating the motor, and a push rod assembly operatively connected to the motor and configured to reciprocate in response to activation of the motor. In a preferred embodiment, the housing includes first, second and third handle portions and a head portion that cooperate to define a handle opening. The first handle portion defines a first axis, the second handle portion defines a second axis and the third handle portion defines a third axis and the first, second and third axes cooperate to form a triangle. The motor is positioned in the head portion of the housing, and at least a portion of the push rod assembly extends outside of the head portion. In a preferred embodiment the first handle portion is generally straight, the second handle portion is generally straight, and the third handle portion is generally straight.

In a preferred embodiment, the percussive therapy device includes a wireless connection device (e.g., Bluetooth or the like) for connecting to a remote device. Remote means that any device separate from the percussive therapy device. The device does not need to be far away to be remote. Preferably, the electrical source is an optional rechargeable battery, and the percussive massage device further includes an optional wireless charging receiver that is in electrical communication with the battery. Preferably, the percussive therapy device includes and optional touchscreen.

In a preferred embodiment, the motor is a brushless motor, a motor mount is positioned in the housing, the motor is secured to the motor mount, and the motor mount is secured to the housing. Preferably, the motor mount includes first and second side walls that define a motor mount interior therebetween. The motor is secured to the first side wall and the second side wall is secured to the housing. In a preferred embodiment, the motor includes a motor shaft that extends through a protrusion opening defined in the first side wall of the motor mount and into the motor mount interior, and at least a portion of the push rod assembly is positioned in the motor mount interior.

In a preferred embodiment, the percussive therapy device includes an attachment connected to a distal end of the push rod assembly, and a routine controller that is configured to initiate a protocol configured to provide user instructions to apply the attachment to a first body part for a first period of time along a first treatment path and to apply the attachment to the first or a second body part for a second period of a time along a second treatment path. Preferably, the user instructions are provided via a touch screen on the percussive therapy device or on an application on a remote electronic device. In a preferred embodiment, the percussive therapy device includes an attachment connected to a distal end of the push rod assembly, and a routine controller that is configured to initiate a protocol configured to provide user instructions to apply the attachment to a first body part for a first period of time and to apply the attachment to the first or a second body part for a second period of a time. The routine controller is configured to reciprocate the attachment at a first speed during the first period of time and at a second speed during the second period of time.

In a preferred embodiment, the percussive therapy device includes a routine controller that is configured to initiate a protocol to activate the motor for at least a first period of a time and a subsequent second period of time During the first period of time the routine controller is configured to provide first user instructions to perform a first task comprising at least one of treating a first body part, moving the attachment along a first treatment path, and connecting a first attachment to a distal end of the push rod assembly, and during the second period of time the routine controller is configured to provide second user instructions to perform a second task comprising at least one of treating a second body part, moving the attachment along a second treatment path, and connecting a second attachment to the distal end of the push rod assembly. The first user instructions may also include instructions regarding grasping one of a first, second or third handle portion, and the second user instructions may also include instructions regarding grasping the same or another of the first, second or third handle portions. Preferably, the first and second user instructions are provided via a touch screen on the percussive therapy device or on an application on a remote electronic device. The first user instructions may also include instructions regarding applying a first target force (based on readings by the force meter), and the second user instructions may also include instructions regarding applying the first target force or a second target force (based on readings by the force meter).

In a preferred embodiment, the electrical source is a battery that is positioned in the second handle portion, and a wireless charging receiver that is in electrical communication with the battery is positioned in the third handle portion.

In accordance with another aspect of the present invention there is provided a method of using a percussive massage device that includes obtaining the percussive massage device that includes a housing having first, second and third handle portions that cooperate to define a handle opening, an electrical source, a motor positioned in the housing, a switch for activating the motor, and a push rod assembly operatively connected to the motor and configured to reciprocate in response to activation of the motor. The method also includes activating the motor using the switch, grasping the first handle portion, massaging a first body part, alternatively grasping the second handle portion and massaging the first body part, and alternatively grasping the third handle portion and massaging the first body part. In a preferred embodiment, the first handle portion defines a first axis, the second handle portion defines a second axis and the third handle portion defines a third axis, and the first, second and third axes cooperate to form a triangle. In a preferred embodiment, the method also includes grasping the second handle portion, massaging a second body part, grasping the third handle portion, and massaging a third body part.

In accordance with another aspect of the present invention there is provided percussive massage device that includes a housing, an electrical source, a motor positioned in the housing, a switch for activating the motor, and a push rod assembly operatively connected to the motor and configured to reciprocate in response to activation of the motor. In a preferred embodiment, the housing includes first, second and third handle portions that cooperate to define a handle opening, wherein the first handle portion defines a first axis, the second handle portion defines a second axis and the third handle portion defines a third axis, and wherein the first, second and third axes cooperate to form a triangle.

Preferably, the first handle portion includes a first handle portion interior edge and defines a first handle portion length and the first handle portion length is long enough that when a user grasps the first handle portion with a hand at least a portion of three fingers extend through the handle opening and contact the first handle portion interior edge. Preferably, the second handle portion includes a second handle portion interior edge and defines a second handle portion length and the second handle portion length is long enough that when a user grasps the second handle portion with a hand at least a portion of three fingers extend through the handle opening and contact the second handle portion interior edge. Preferably, the third handle portion includes a third handle portion interior edge and defines a third handle portion length and the third handle portion length is long enough that when a user grasps the third handle portion with a hand at least a portion of three fingers extend through the handle opening and contact the third handle portion interior edge. In a preferred embodiment, the first handle portion is generally straight, the second handle portion is generally straight and the third handle portion is generally straight. Generally straight means that the majority of the handle portion is straight, but can include rounded edges or corners where the different handle portions meet or where the handle portions meet the bulge portion or the finger protrusion, etc.

In a preferred embodiment, the switch includes switch electronics associated therewith, the electrical source is a battery that is housed in the second handle portion and the switch electronics are housed in the first handle portion. Preferably, the motor is configured to rotate a pinion shaft having a pinion gear thereon about a shaft rotation axis. The housing includes a gear member disposed therein that is operatively engaged with the pinion gear and rotates about a gear rotation axis. The push rod assembly is operatively connected to the gear member, and rotational motion of the pinion shaft is converted to reciprocating motion of the push rod assembly through the engagement of the pinion gear and the gear member. The motor includes a motor shaft extending outwardly therefrom and a pinion coupling assembly is positioned between the motor shaft and the pinion shaft. The pinion coupling includes a lower connector that is operatively connected to the motor shaft, an upper connector that is operatively connected to the pinion shaft, and a cross coupling positioned between the lower connector and the upper connector. In a preferred embodiment, the lower connector includes a main body portion that defines a central opening that receives the motor shaft and first and second lower connector arms extending outwardly from the main body portion, the upper connector includes a main body portion that defines a central opening that receives the pinion shaft and first and second upper connector arms extending outwardly from the main body portion, the cross coupling includes radially extending ribs, and the first and second lower connector members and the first and second upper connector members operatively engage the radially extending ribs. Preferably, the lower and upper connectors comprise a plastic and the cross coupling comprises an elastomer.

In a preferred embodiment, the gear member is disposed in a rotation housing that is rotatable between at least first and second positions. A gearbox housing that houses the gear member is disposed in the rotation housing. The gearbox housing includes a clearance slot having first and second ends defined therein. The push rod assembly extends through the clearance slot, such that when the rotation housing is rotated from the first position to the second position the push rod assembly moves within the clearance slot from adjacent the first end to adjacent the second end.

In a preferred embodiment, the push rod assembly includes a first rod portion having a proximal end and a distal end and a second rod portion having a proximal end and a distal end. The proximal end of the first rod portion is operatively connected to the motor. An adapter assembly is positioned between the first and second rod portions. The adapter assembly allows the first rod portion to pivot with respect to the second rod portion. Preferably, the adapter assembly includes an adapter member that includes a pocket that receives the distal end of the first rod portion therein. A pivot pin spans the pocket and extends through the distal end of the first rod portion. In a preferred embodiment, the adapter member includes a protrusion that is received in the proximal end of the second rod portion.

In accordance with another aspect of the present invention there is provided a massage device that includes a housing, an electrical input, a motor, a switch in electrical communication with the electrical input and the motor and configured to selectively provide power from the electrical input to the motor, an actuated output operatively connected to the motor and configured to reciprocate in response to activation of the motor, and a treatment structure operatively connected to a distal end of the actuated output. The actuated output is configured to reciprocate the treatment structure at a frequency of between about 15 Hz and about 100 Hz, and at an amplitude of between about 0.15 and about 1.0 inches. The combination of amplitude and frequency provides efficient reciprocation of the treatment structure such that the treatment structure provides therapeutically beneficial treatment to a targeted muscle of a user.

In a preferred embodiment, the actuated output is configured to reciprocate the treatment structure at a frequency of between about 25 Hz and about 48 Hz, and at an amplitude of between about 0.23 and about 0.70 inches. In another preferred embodiment, the actuated output is configured to reciprocate the treatment structure at a frequency of between about 33 Hz and about 42 Hz, and at an amplitude of between about 0.35 and about 0.65 inches.

In accordance with another aspect of the present invention there is provided a percussive massage device with a force meter that includes a housing, an electrical source, a motor positioned in the housing, a switch for activating the motor, and a controller configured to obtain a voltage of the motor, generate a lookup table correlating voltage to force applied by the percussive massage device, and display a force magnitude corresponding to the obtained voltage using the lookup table. In a preferred embodiment, the lookup table is generated by determining a maximum magnitude of force configured to be applied by the percussive massage device, determining a maximum magnitude of voltage configured to be applied to the percussive massage device from a power source, dividing the maximum magnitude of force into equal force increments, and dividing the maximum magnitude of voltage into equal voltage increments. The number of equal force increments and the number of equal voltage increments is the same. Preferably, the percussive massage device includes a battery pack and a display configured to depict an amount of force applied by the percussive massage device. In a preferred embodiment, the display includes a series of LEDs. In a preferred embodiment, the percussive massage device includes an organic light-emitting diode screen.

In a preferred embodiment, the motor is a brushless direct-current (BLDC) motor. Preferably, the percussive massage device includes a voltage-sensing resistor electrically coupled to the BLDC motor and the controller.

In accordance with another aspect of the present invention there is provided a method of displaying force of a percussive massage device that includes obtaining a voltage of a motor of the percussive massage device, generating a lookup table correlating voltage to force applied by the percussive massage device, and displaying a force magnitude corresponding to the obtained voltage using the lookup table. In a preferred embodiment, the lookup table correlating voltage to force is linear. Preferably, the lookup table is generated by determining a maximum magnitude of force configured to be applied by the percussive massage device, determining a maximum magnitude of voltage configured to be applied to the percussive massage device from a power source, dividing the maximum magnitude of force into equal force increments, and dividing the maximum magnitude of voltage into equal voltage increments, wherein the number of equal force increments and the number of equal voltage increments is the same.

In a preferred embodiment, the method includes obtaining a maximum power source voltage of the percussive massage device, setting the maximum power source voltage to be the maximum magnitude of voltage, dividing the maximum magnitude of voltage into equal voltage increments, wherein the number of equal force increments and the number of equal voltage increments is the same, generating an updated lookup table correlating voltage to force applied by the percussive massage device corresponding to the range of voltages determined by the maximum power source voltage, and displaying a calibrated force magnitude corresponding to the power source voltage using the updated lookup table. In a preferred embodiment, the method includes obtaining at least two power source voltages each corresponding to a magnitude of force, wherein the magnitude of force is determined from the displayed force magnitude, measuring a magnitude of force exerted by the percussive massage device using an external force meter for each of the at least two power source voltages, and generating an updated lookup table correlating voltage to force applied by the percussive massage device corresponding to the measured magnitudes of force.

In a preferred embodiment, the method includes displaying a calibrated force magnitude corresponding to the measured magnitudes of force using the updated lookup table. Preferably, the lookup table is updated for each magnitude of force capable of being displayed on the percussive massage device.

In accordance with another aspect of the present invention there is provided a method of displaying force of a percussive massage device that includes obtaining a current magnitude of a battery pack of the percussive massage device, obtaining a voltage magnitude of the battery pack, determining a power magnitude using the current magnitude and voltage magnitude of the battery pack, generating a lookup table correlating power magnitude to force magnitude applied by the percussive massage device, and displaying a force magnitude corresponding to the obtained power magnitude using the lookup table. In a preferred embodiment, the force magnitude is displayed utilizing a series of LEDs which are activated corresponding with the force magnitude. Preferably, the lookup table is generated by determining a maximum power magnitude to be input into the percussive massage device, determining a minimum power magnitude of the percussive massage device when no load is applied to the percussive massage device, determining a maximum force magnitude configured to be applied to the percussive massage device from a power source, dividing the maximum power magnitude into equal power increments, and dividing the maximum force magnitude into equal force increments. The number of equal power increments and the number of equal force increments is the same. Preferably, the maximum power magnitude is a maximum effective power magnitude derived from a total effective power.

In a preferred embodiment, the method includes determining at least two power magnitudes using current and voltage measurements of the battery pack, each corresponding to a magnitude of force. The magnitude of force is determined from the displayed force magnitude. Measuring a magnitude of force exerted by the percussive massage device using an external force meter for each of the at least two power magnitudes, and generating an updated lookup table correlating power to force applied by the percussive massage device corresponding to the measured magnitudes of force. In a preferred embodiment, the method includes displaying a calibrated force magnitude corresponding to the measured magnitudes of force using the updated lookup table. Preferably, the lookup table is updated for each magnitude of force capable of being displayed on the percussive massage device.

It will be appreciated that the inventive features discussed herein can be used with any type of percussive massage device. For example, the force meter and other features taught herein can be used with the percussive massage device disclosed in U.S. Pat. No. 10,357,425 ("the '425 patent"), the entirety of which is incorporated herein by reference.

In an embodiment, a non-transitory computer-readable medium has stored thereon software instructions that, when executed by a processor, cause the processor to obtain a voltage of a motor of the percussive massage device, generate a lookup table correlating voltage to force applied by the percussive massage device, and display a force magnitude corresponding to the obtained voltage using the lookup table.

In an embodiment, the lookup table is generated by determining a maximum magnitude of force configured to be applied by the percussive massage device, determining a maximum magnitude of voltage configured to be applied to the percussive massage device from a power source, dividing the maximum magnitude of force into equal force increments, and dividing the maximum magnitude of voltage into equal voltage increments. In an embodiment, the number of equal force increments and the number of equal voltage increments is the same.

In another embodiment, a non-transitory computer-readable medium has stored thereon software instructions that, when executed by a processor, cause the processor to obtain a maximum power source voltage of the percussive massage device, set the maximum power source voltage to be the maximum magnitude of voltage, and divide the maximum magnitude of voltage into equal voltage increments, generate an updated lookup table correlating voltage to force applied by the percussive massage device corresponding to the range of voltages determined by the maximum power source voltage, and display a calibrated force magnitude corresponding to the power source voltage using the updated lookup table.

In another embodiment, a non-transitory computer-readable medium has stored thereon software instructions that, when executed by a processor, cause the processor to obtain at least two power source voltages each corresponding to a magnitude of force, wherein the magnitude of force is determined from the displayed force magnitude, measure a magnitude of force exerted by the percussive massage device using an external force meter for each of the at least two power source voltages; and generate an updated lookup table correlating voltage to force applied by the percussive massage device corresponding to the measured magnitudes of force.

In an embodiment, a non-transitory computer-readable medium has stored thereon software instructions that, when executed by a processor, cause the processor to obtain a current magnitude of a battery pack of the percussive massage device, obtain a voltage magnitude of the battery pack, determine a power magnitude using the current magnitude and voltage magnitude of the battery pack, generate a lookup table correlating power magnitude to force magnitude applied by the percussive massage device, and display a force magnitude corresponding to the obtained power magnitude using the lookup table.

In an embodiment, a non-transitory computer-readable medium has stored thereon software instructions that, when executed by a processor, cause the processor to determine at least two power magnitudes using current and voltage measurements of the battery pack, each corresponding to a magnitude of force, wherein the magnitude of force is determined from the displayed force magnitude, measure a magnitude of force exerted by the percussive massage device using an external force meter for each of the at least two power magnitudes, and generate an updated lookup table correlating power to force applied by the percussive massage device corresponding to the measured magnitudes of force.

In a preferred embodiment, the motor, in one embodiment, converts power from the power source into motion. In some embodiments, the motor is an electric motor. The electric motor may be any type of electric motor known in the art, including, but not limited to, a brushed motor, a brushless motor, a direct current (DC) motor, an alternating current (AC) motor, a mechanical-commutator motor, an electronic commutator motor, or an externally commutated motor.

In some embodiments, the actuated output or output shaft reciprocates at a rate of approximately 65 Hz. The actuated output, in some embodiments, reciprocates at a rate over 50 Hz. The reciprocating treatment device, in some embodiments, provides reciprocation at a rate ranging between 50 Hz and 80 Hz. In some embodiments, the actuated output has a maximum articulation rate of between 50 Hz and 80 Hz. In another embodiment, the actuated output has an articulation rate of between 30 Hz and 80 Hz. In certain embodiments, the actuated output has an articulation rate of approximately 37 Hz. In one embodiment, the actuated output has an articulation rate of approximately 60 Hz. In a preferred embodiment, the actuated output articulates or reciprocates at a frequency of between about 15 Hz and about 100 Hz. In a more preferred embodiment, the actuated output articulates or reciprocates at a frequency of between about 25 Hz and about 48 Hz. In the most preferred embodiment, the actuated output articulates or reciprocates at a frequency of between about 33 Hz and about 42 Hz. Any chosen range within the specified ranges is within the scope of the present invention.

The actuated output may move through a predetermined range of reciprocation. For example, the actuated output may be configured to have an amplitude of one half inch. In another embodiment, the actuated output may be configured to have an amplitude of one quarter inch. As will be appreciated by one skilled in the art, the actuated output may be configured to have any amplitude deemed therapeutically beneficial.

In some embodiments, the actuated output may be adjustable through a variable range of reciprocation. For example, the reciprocating treatment device may include an input to adjust the reciprocation amplitude from one quarter of an inch through a range of up to one inch. In a preferred embodiment, the actuated output moves through an amplitude of between about 0.15 inches and about 1.0 inches. In a more preferred embodiment, the actuated output articulates or reciprocates at a frequency of between about 0.23 inches and about 0.70 inches. In the most preferred embodiment, the actuated output articulates or reciprocates at a frequency of between about 0.35 inches and about 0.65 inches. Any chosen range within the specified ranges is within the scope of the present invention.

It will be appreciated that the device operates most effectively within the combined frequency and amplitude ranges. When developing the invention, the inventor determined that if the frequency and amplitude are above the ranges set forth above the device can cause pain and below the ranges the device is ineffective and does not provide effective therapeutic relief or massage. Only when the device operates within the disclosed combination of frequency and amplitude ranges does it provide efficient and therapeutically beneficial treatment to the muscles targeted by the device.

In certain embodiments, the reciprocating treatment device includes one or more components to regulate the articulation rate of the actuated output in response to varying levels of power provided at the power input. For example, the reciprocating treatment device may include a voltage regulator (not shown) to provide a substantially constant voltage to the motor over a range of input voltages. In another embodiment, the current provided to the motor may be regulated. In some embodiments, operation of the reciprocating treatment device may be restricted in response to an input voltage being below a preset value.

In a preferred embodiment, the percussive massage device includes a brushless motor. It will be appreciated that the brushless motor does not include any gears and is quieter than geared motors.

The device includes a push rod or shaft that is connected directly to the motor by a pin. In a preferred embodiment, the push rod is L-shaped or includes an arc shape. Preferably, the point where the push rod is connected to the pin is offset from reciprocating path that the distal end 40 of the push rod (and the massage attachment) travel. This capability is provided by the arc or L-shape. It should be appreciated that the push rod is designed such that it can transmit the force diagonally instead of vertically so the motor can be located at or near the middle of the device, otherwise a protrusion would be necessary to keep the shaft in the center with the motor offset therefrom (and positioned in the protrusion). The arc also allows the push rod to have a close clearance with the motor and allows the outer housing to be smaller than similar prior art devices, therefore making the device lower profile. Preferably two bearings are included at the proximal end of the push rod where it connects to the motor to counteract the diagonal forces and preventing the push rod for moving and touching the motor.

In a preferred embodiment, the device includes a touch screen for stopping, starting, activating, etc. The touch screen can also include other functions. Preferably, the device includes a thumbwheel or rolling button positioned near the touch screen/on off button to allow the user to scroll or navigate through the different functions. Preferably, the device also includes variable amplitude or stroke. For example, the stroke can change or be changed between about 8-16 mm.

In a preferred embodiment, the device is associated with and can be operated by an app or software that runs on a mobile device such as a phone, watch or tablet (or any computer). The app can connect to the device via bluetooth or other connection protocol. The app can have any or all of the following functions. Furthermore, any of the functions discussed herein can be added to the touch screen/scroll wheel or button(s) capability directly on the device. If the user walks or is located too far away from the device, the device will not work or activate. The device can be turned on an off using the app as well as the touch screen or button on the device. The app can control the variable speeds (e.g., anywhere between 1750-3000 RPM). A timer so the device stops after a predetermined period of time. The app can also include different treatment protocols associated therewith. This will allow the user to choose a protocol or area of the body they want to work on. When the start of the protocol is selected, the device will run through a routine. For example, the device may run at a first RPM for a first period of time and then run at a second RPM for a second period of time and/or at a first amplitude for a first period of time and then run at a second amplitude for a second period of time. The routines can also include prompts (e.g., haptic feedback) for letting the user to know to move to a new body part. These routines or treatments can be related to recovery, blood flow increase, performance, etc. and can each include a preprogrammed routine. The routines can also prompt or instruct the user to switch treatment structures (AmpBITS) or positions of the arm or rotation head. The prompts can include sounds, haptic feedback (e.g., vibration of the device or mobile device), textual instructions on the app or touch screen, etc. For example, the app may instruct the user to start with the ball treatment structure with the arm in position two. Then the user hits start and the device runs at a first frequency for a predetermined amount of time. The app or device then prompts the user to begin the next step in the routine and instructs the user to change to the cone treatment structure and to place the arm in position 1. The user hits start again and the device runs at a second frequency for a predetermined amount of time.

In a preferred embodiment, the app includes near field communication ("NFC") capability or other capability that allows the user's mobile device with the app thereon to scan an identifier, such as a barcode or a QR code that prompts the app to display certain information, such as the routines discussed above. In use, a user will be able to tap or place their mobile device near an NFC tag (or scan a QR code) on a piece of gym equipment and the app will show instructions, content or a lesson that is customized for using the device with that piece of equipment. For example, on a treadmill, the user scans the QR code or NFC tag and the app recognizes that the user is about to use the treadmill. The app can then provide instructions for how to use the device in conjunction with the treadmill and can initiate a preprogrammed routine for using the treadmill. For example, the user can be instructed to start with the left quad. Then, after a predetermined period of time (e.g., 15 seconds), the device, or the mobile device that includes the app software thereon, vibrates or provides other haptic feedback. The user then switches to their left quad and after a predetermined period of time the device again vibrates. The user can then begin using the treadmill. Any routine is within the scope of the present invention. In an embodiment, the device and/or app (i.e., the mobile device containing the app) can also communicate (via bluetooth or the like) with the gym equipment (e.g., treadmill).

The device can also include a torque or force meter to let the user know how much force they are applying. The display associated with the force meter shows how much force is being applied on the muscle. The force meter allows for a more precise and effective treatment. The device includes a torque measuring sensor and display. Depending on the muscle the device is being used on and the benefit the user is looking to get (prepare, perform, recover) the force that should be applied varies. By having a torque sensor, the user is able to get a more precise and personalized treatment. The app and the touchscreen can provide the force information to the user. The force meter can be integrated with the routines and the user can be provided feedback with whether they are applying too much or too little pressure. The device can also include a thermal sensor or thermometer that can determine the temperature of the user's muscle and to provide feedback to the device and/or app. The haptic feedback can also provide feedback for too much pressure or force.

In a preferred embodiment, the percussive massage device includes a motor mount for mounting the brushless motor within the housing and for distributing forces from the motor as it operates to the housing. The motor is secured to a first side of the motor mount and the second or opposing side of the motor mount is secured to the housing. The motor mount includes a plurality of arms that space the motor from the housing and define a reciprocation space in which the push rod and associated components (counterweight, etc.) reciprocate. Threaded fasteners connect the motor mount to the housing. In a preferred embodiment, dampening members or feet are received on the shaft of the threaded fastener. The dampening members each include an annular slot defined therein. The annular slots receive housing. This prevents direct contact of the threaded fasteners with the housing and reduces sound from vibrations. The threaded fasteners are received in openings in tabs at the end of the arms.

In a preferred embodiment, the motor is housed in a motor housing that is rotatable within the main housing. The motor housing is basically the equivalent of the gear box housing in related embodiments. In a preferred embodiment, there are opposite openings in the outside of the motor housing that expose the motor on one side and the motor mount on the other. The openings provide ventilation for the motor and allow the motor mount to connect directly to the main housing.

In a preferred embodiment, the device includes a touch screen as well as button(s) for operating the device. For example, the device can include a touch screen, a center button for turning the device on and off and a ring/rocker button that provides the ability to scroll left and right (e.g., to the preset treatments discussed herein) and up and down (e.g., to control the speed or frequency). The screen can also be a non-touch screen.

In another preferred embodiment, any of the devices taught herein can include the ability to vary the amplitude, thus providing a longer or shorter stroke depending on the application or needs of the user. The amplitude variability can also be part of the routines or presets discussed herein. For example, the device can include a mechanical switch that allows the eccentricity of the connector to be modified (e.g., between 4 mm and 8 mm). The mechanism can include a push button and a slider. The pin structure has a spring that lets it fall back into the locked position.

In a preferred embodiment, the device includes a touch screen for stopping, starting, activating, etc. The touch screen can also include other functions. Preferably, the device includes a thumbwheel or rolling button positioned near the touch screen/on off button to allow the user to scroll or navigate through the different functions.

BRIEF DESCRIPTION OF THE DRAWINGS

The invention may be more readily understood by referring to the accompanying drawings in which:

FIG. 44 is a chart showing steps of Protocol 1 in accordance with a method of performing a routine for a percussive massage device;

FIG. 45 is a chart showing steps of a "Shin Splints" protocol in accordance with a method of performing a routine for a percussive massage device;

Like numerals refer to like parts throughout the several views of the drawings.

DETAILED DESCRIPTION OF THE PREFERRED EMBODIMENTS

Figure 1:
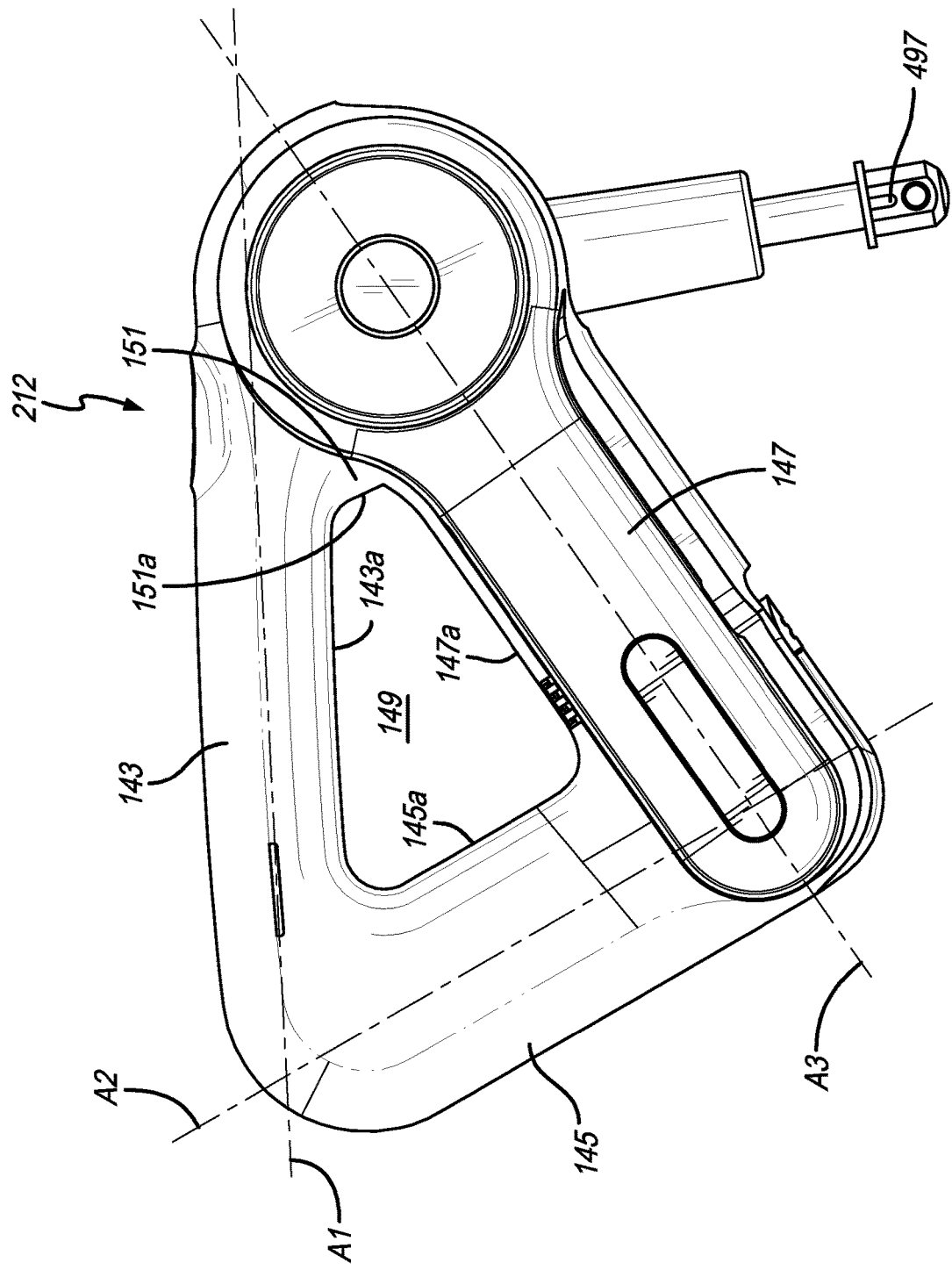
FIG. 1 is a side elevational view of a percussive massage device in accordance with a preferred embodiment of the present invention.

The following description and drawings are illustrative and are not to be construed as limiting. Numerous specific details are described to provide a thorough understanding of the disclosure. However, in certain instances, well-known or conventional details are not described in order to avoid obscuring the description. References to one or another embodiment in the present disclosure can be, but not necessarily are, references to the same embodiment; and, such references mean at least one of the embodiments.

Reference in this specification to "one embodiment" or "an embodiment" means that a particular feature, structure, or characteristic described in connection with the embodiment is included in at least one embodiment of the disclosure. Appearances of the phrase "in one embodiment" in various places in the specification do not necessarily refer to the same embodiment, nor are separate or alternative embodiments mutually exclusive of other embodiments. Moreover, various features are described which may be exhibited by some embodiments and not by others. Similarly, various requirements are described which may be requirements for some embodiments but not other embodiments.

The terms used in this specification generally have their ordinary meanings in the art, within the context of the disclosure, and in the specific context where each term is used. Certain terms that are used to describe the disclosure are discussed below, or elsewhere in the specification, to provide additional guidance to the practitioner regarding the description of the disclosure. For convenience, certain terms may be highlighted, for example using italics and/or quotation marks: The use of highlighting has no influence on the scope and meaning of a term; the scope and meaning of a term is the same, in the same context, whether or not it is highlighted. It will be appreciated that the same thing can be said in more than one way.

Consequently, alternative language and synonyms may be used for any one or more of the terms discussed herein. Nor is any special significance to be placed upon whether or not a term is elaborated or discussed herein. Synonyms for certain terms are provided. A recital of one or more synonyms does not exclude the use of other synonyms. The use of examples anywhere in this specification including examples of any terms discussed herein is illustrative only, and is not intended to further limit the scope and meaning of the disclosure or of any exemplified term. Likewise, the disclosure is not limited to various embodiments given in this specification.

Without intent to further limit the scope of the disclosure, examples of instruments, apparatus, methods and their related results according to the embodiments of the present disclosure are given below. Note that titles or subtitles may be used in the examples for convenience of a reader, which in no way should limit the scope of the disclosure. Unless otherwise defined, all technical and scientific terms used herein have the same meaning as commonly understood by one of ordinary skill in the art to which this disclosure pertains. In the case of conflict, the present document, including definitions, will control.

It will be appreciated that terms such as "front," "back," "top," "bottom," "side," "short," "long," "up," "down," and "below" used herein are merely for ease of description and refer to the orientation of the components as shown in the figures. It should be understood that any orientation of the components described herein is within the scope of the present invention.

While many embodiments are described herein, at least some of the described embodiments provide an apparatus, system, and method for a reciprocating treatment device.

Figure 1A:
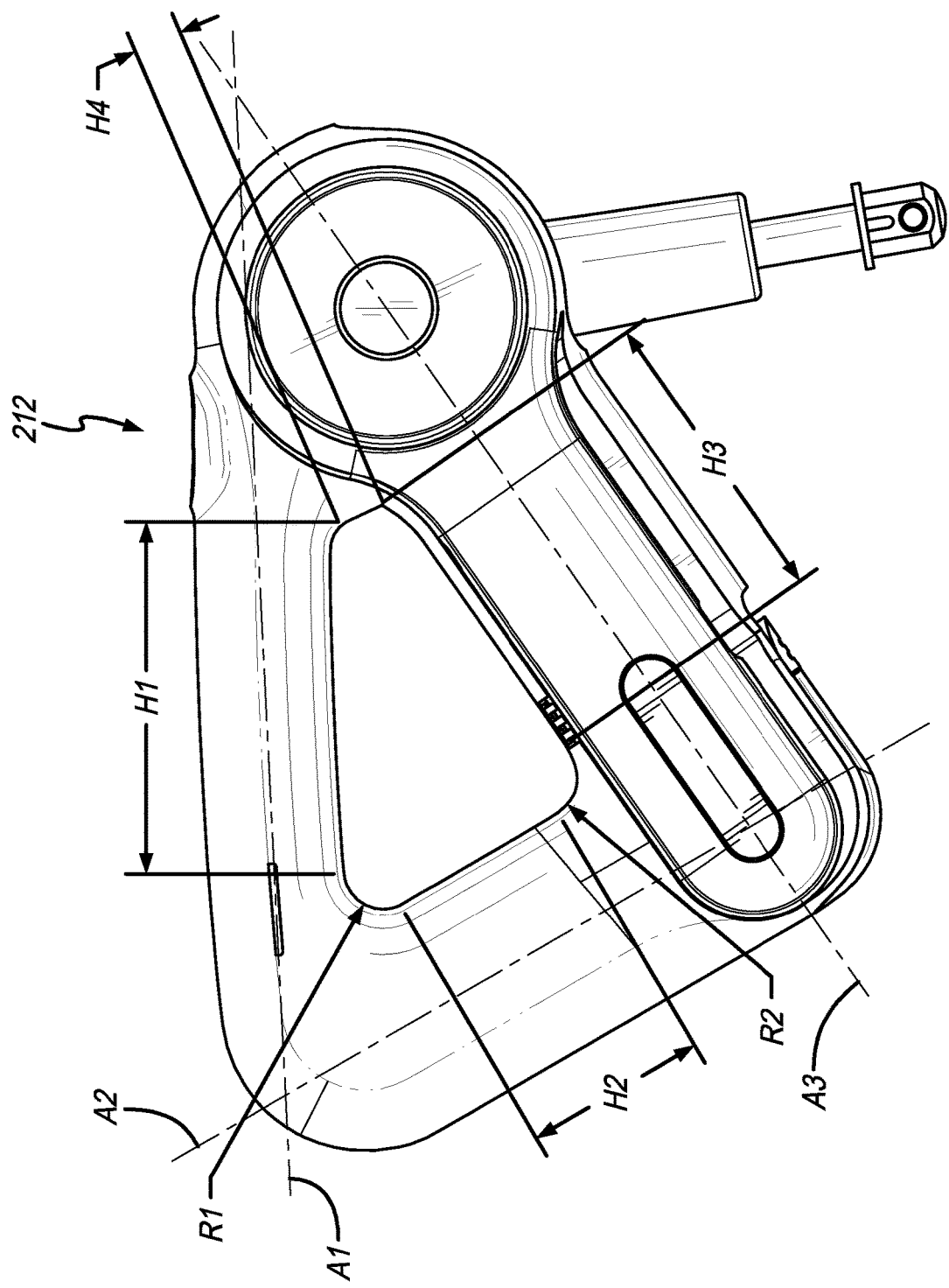
FIG. 1A is another side elevational view of the percussive massage device of FIG. 1.

FIGS. 1-10 show an embodiment of a percussive massage device 212 that includes a rechargeable battery (and replaceable or removable battery) 114. Device 212 is referred to commercially as the G3PRO. As shown in FIGS. 1-1A, in a preferred embodiment, the percussive massage device 212 includes three handle portions (referred to herein as first handle portion 143, second handle portion 145 and third handle portion 147) that cooperate to define a central or handle opening 149. All of the handle portions are long enough that they are configured such that a person can grasp that particular handle portion to utilize the device. The ability to grasp the different handle portions allows a person (when using the device on their own body) to use the device on different body parts and from different angles, thus providing the ability to reach body parts, such as the back, that might not be possible without the three handle portions.

As shown in FIG. 1, the first handle portion 143 defines a first handle portion axis A1, the second handle portion 145 defines a second handle portion axis A2 and the third handle portion 147 defines a third handle portion axis A3 that cooperate to form a triangle. In a preferred embodiment, the battery 114 is housed in the second handle portion 145 and the motor 106 is housed in the third handle portion 147.

Figure 3:
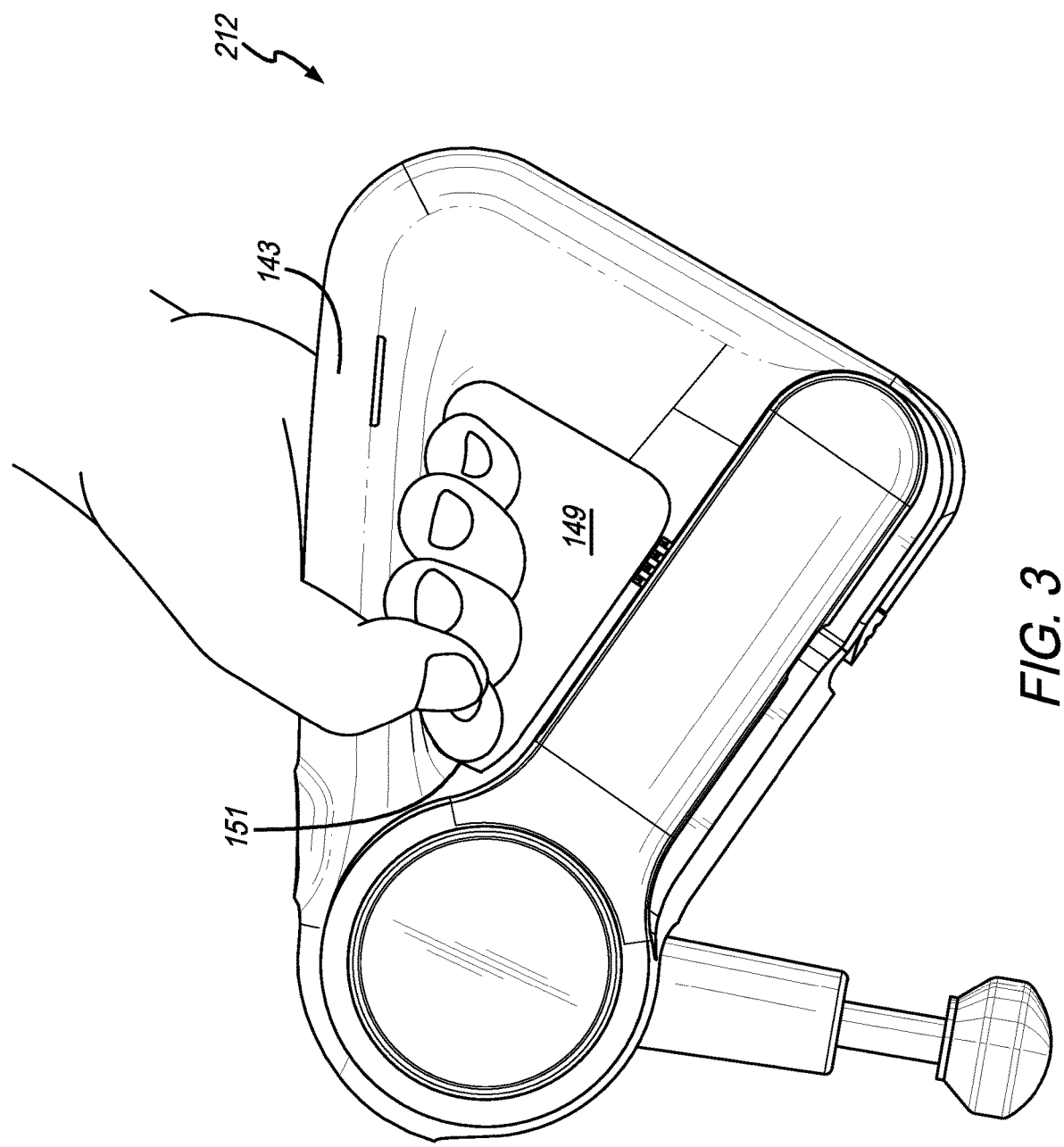
FIG. 3 is a side elevational view of the percussive massage device showing a user grasping the first handle portion.
Figure 4:
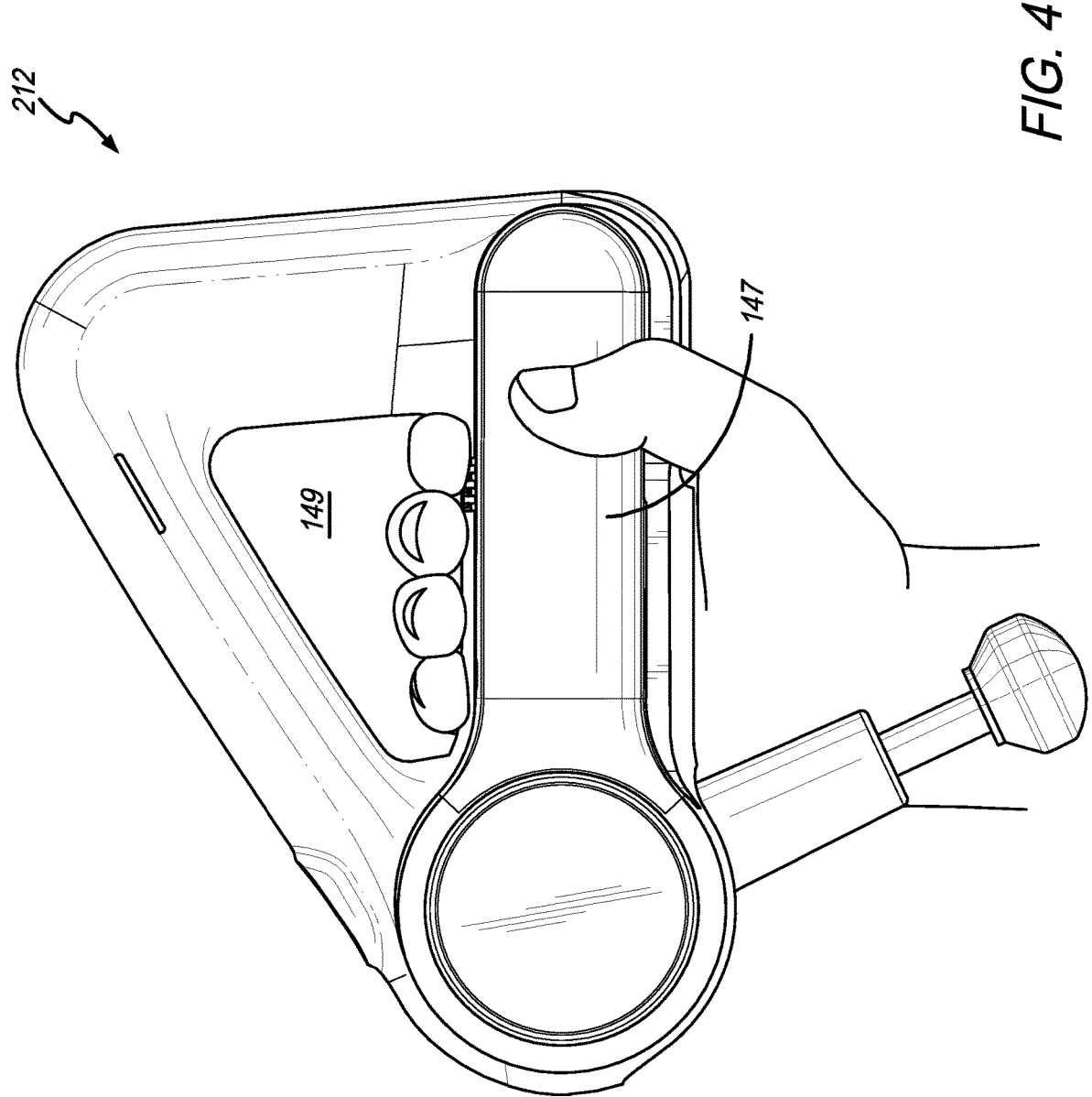
FIG. 4 is a side elevational view of the percussive massage device showing a user grasping the third handle portion.
Figure 5:
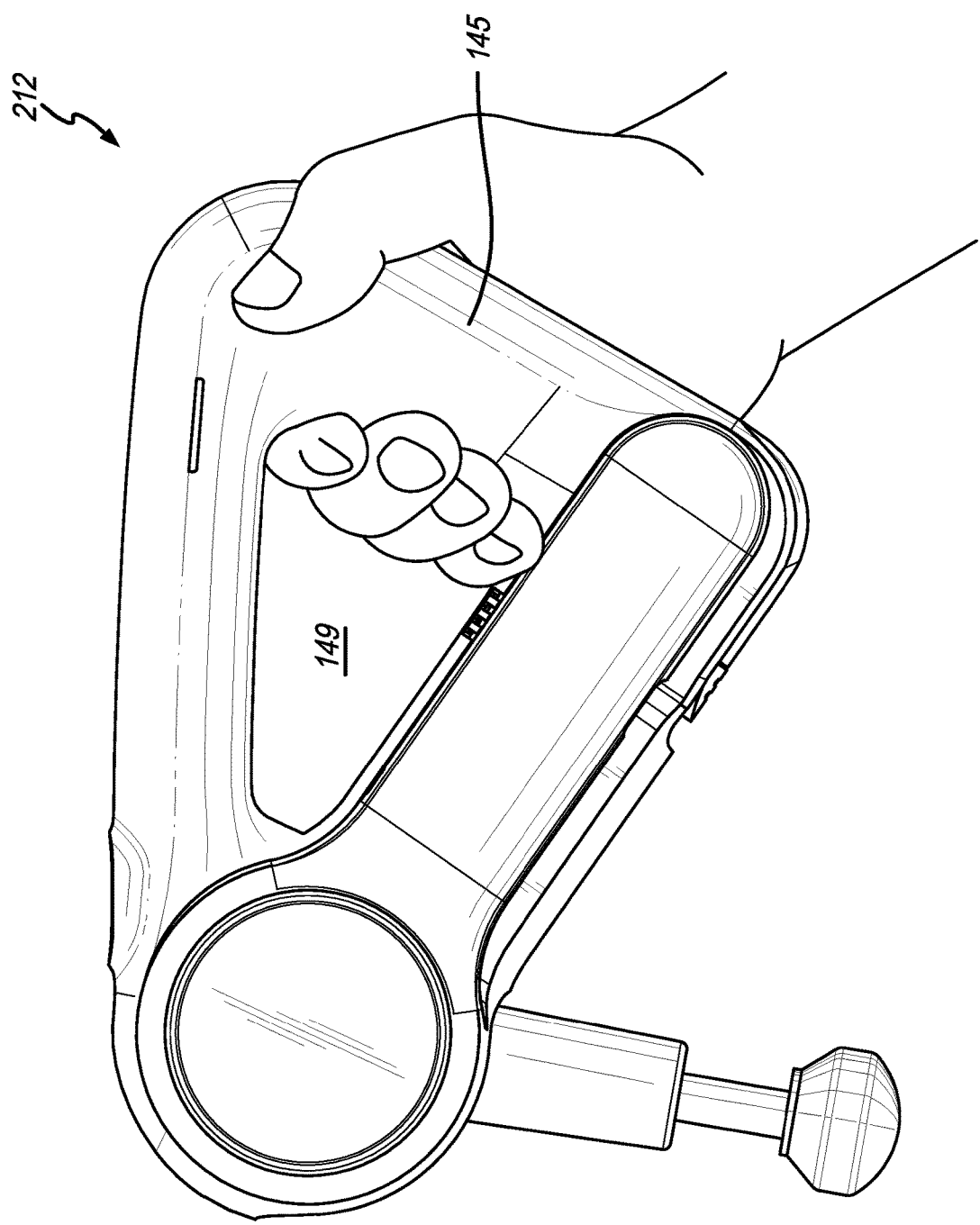
FIG. 5 is a side elevational view of the percussive massage device showing a user grasping the second handle portion.

FIGS. 3-5 show a user's hand grasping the various handle portions. The length of each of the first, second and third handle portions is long enough so that a person with a large hand can comfortably grasp each handle portion with at least three to four fingers extending through the handle opening, as shown in FIGS. 3-5. In a preferred embodiment, the first handle portion 143 has an interior edge 143a, the second handle portion 145 has an interior edge 145a and the third handle portion 147 has an interior edge 147a, which all cooperate to at least partially define the handle opening 149.

As shown in FIG. 1, in a preferred embodiment, the first handle portion 143 includes a finger protrusion 151 that includes a finger surface or fourth interior surface 151a that extends between the interior edge 143a of the first handle portion and the interior edge 147a of the third handle portion 147 and at least partially defines the handle opening 149. As shown in FIG. 3, in use, a user can place their index finger against the finger surface 151a. The finger protrusion and surface provide a feedback point or support surface such that when a user places their index finger against the surface it helps the user with control and comfort of using the device. In a preferred embodiment, at least a portion of the finger surface 151a is straight, as shown in FIG. 1 (as opposed to the other "corners" of the handle opening 149 being rounded).

FIG. TA shows the preferred dimensions of the interior surfaces of the handle opening 149. It will be appreciated that the interior surfaces comprise a series of flat and curved surfaces. H1 is the dimension of the interior edge 143a of the first handle portion 143 (the first handle portion length). H2 is the dimension of the interior edge 145a of the second handle portion 145 (the second handle portion length). H3 is the dimension of the interior edge 147a of the third handle portion 147 (the third handle portion length). H4 is the dimension of the finger surface 151a (the finger protrusion length). R1 is the dimension of the radius between interior edges 143a and 145a and R2 is the dimension of the radius between interior edges 145a and 147a. In a preferred embodiment, H1 is about 94 mm, H2 is about 66 mm, H3 is about 96 mm, H4 is about 12 mm, R1 is about 6.5 mm and R2 is about 6.5 mm, which provides an arc length of about 10.2 mm. In the context herein, "about" is within 5 mm. In a preferred embodiment, the length of the interior edge of the handle opening is about 289 mm. The length of the interior edge of the handle opening can be between about 260 mm and about 320 mm, with any combination of H1, H2, H3, H4, R1 and R2. It will be appreciated that these dimensions are optimized so that a 95th percentile male can grip any of the three handle portions with at least three and preferably four fingers extending through the handle opening to utilize the device. It will be appreciated that any or all of surfaces R1 and R2 can be considered a part of any of the three adjacent handle portions. As shown in FIGS. 1 and 1A, with the finger surface 151a being straight, the first handle portion interior surface, second handle portion interior surface, third handle portion interior surface and finger surface cooperate to define a quadrilateral with radii or rounded edges between each of the straight surfaces.

Device 212 also includes multiple speed settings (preferably 1500 and 2400 RPM, but can be any speed or frequency taught herein). Furthermore, those of ordinary skill in the art will appreciate that although the RPM is listed as a specific number that, due to manufacturing tolerances, the RPM may oscillate during use. For example, at the 2400 RPM setting the RPM may actually oscillate between 2260 and 2640.

Figure 6:
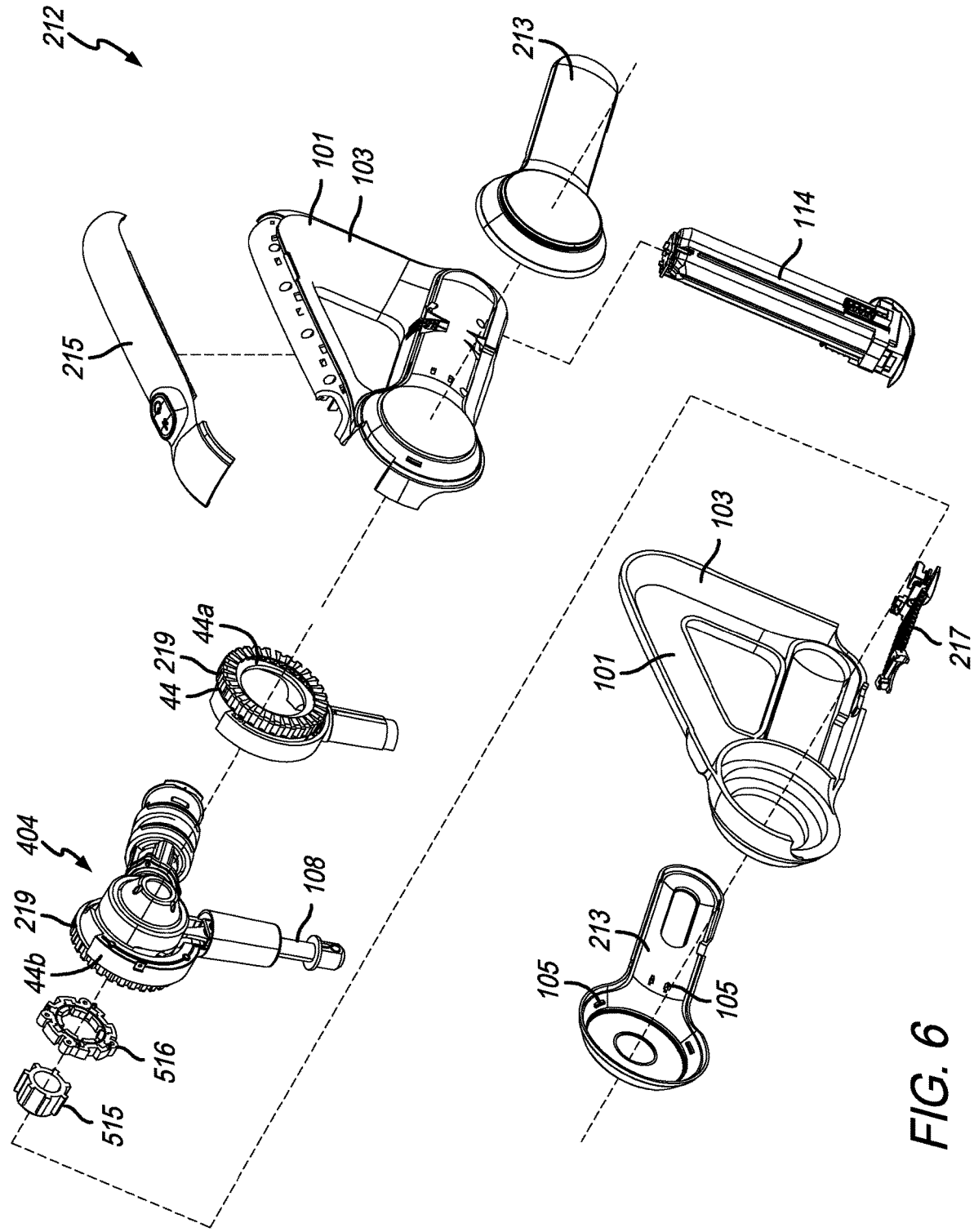
FIG. 6 is an exploded perspective view of the percussive massage device.

FIGS. 6-10 show some of the interior and exterior components that are included in the treatment devices 212 (208 and 210) shown in FIGS. 1-5 and 11-16. As shown in FIG. 6, the percussive massage device 212 includes a housing 101 that is comprised of first and second housing halves 103. Outer covers 213 and top cover 215 are received on and connected to the first and second housing halves 103, via tabs 105 or other mechanism or attachment method (e.g., threaded fasteners, clips, adhesive, sonic welding, etc.). The percussive massage device 212 also includes a tambour door 217, battery 114, inner suspension rings 219 and rotation housing 44 (with first and second rotation housing halves 44a and 44b) that houses the gearbox 404.

Figure 7:
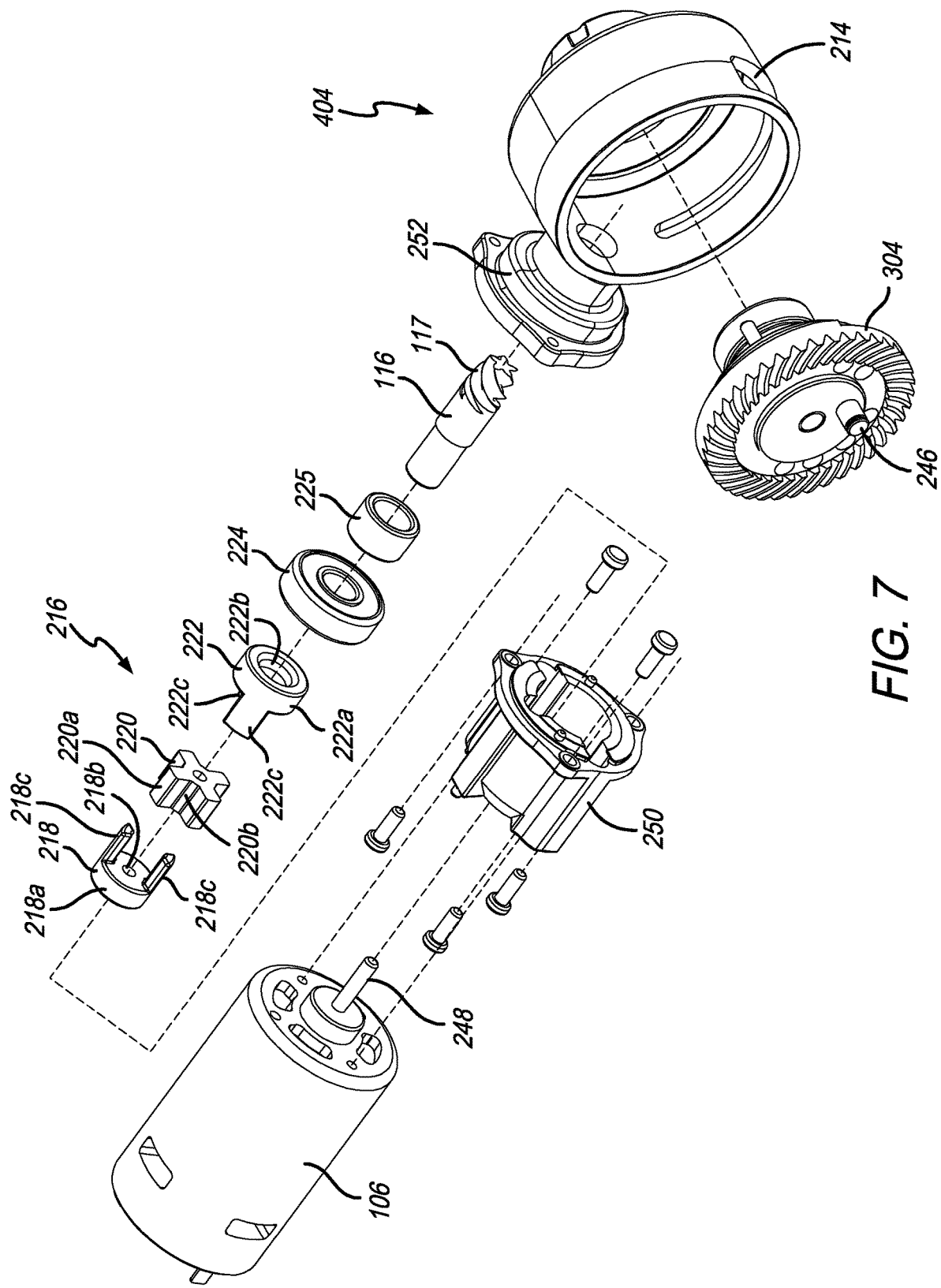
FIG. 7 is an exploded perspective view of a portion of the drive train components of the percussive massage device.

As shown in FIG. 7, the device includes a pinion coupling assembly 216 that is disposed between the motor and the shaft gear 117 (located on the shaft or pinion shaft 116). The pinion coupling assembly 216 is used to couple the motor to the gearbox so that the torque is fully transmitted, such that there is no radial movement and the vibrations and noise are minimized. The pinion coupling assembly 216 preferably includes three separate components, a lower connector 218, a cross coupling 220 and an upper connector 222. In a preferred embodiment, the lower connector 218 includes a main body portion 218a that defines a central opening 218b that receives the motor shaft 248 and first and second lower connector arms 218c extending outwardly from the main body portion 218a. The upper connector 222 includes a main body portion 222a that defines a central opening 222b that receives the pinion shaft 116 and first and second upper connector arms 222c extending outwardly from the main body portion 222a. Preferably, the cross coupling 220 includes radially extending ribs 220a that define channels 220b therebetween. The first and second lower connector arms 218c and the first and second upper connector arms 222c are sized and shaped to be received in the channels 220b to operatively engage the radially extending ribs. In use, the motor shaft 248 rotates the pinion coupling assembly, which rotates the pinion shaft 116. These components work together to reduce noise and vibration. In a preferred embodiment, the lower and upper connectors are made of plastic and the cross coupling is made of an elastomer. In a preferred embodiment, the cross coupling 220 is made of rubber that includes a hardness where vibrations generated by the motor are isolated while keeping the strength and transmitting the torque efficiently (without significant energy dissipation). However, the materials are not a limitation on the present invention.

In a preferred embodiment, the pinion shaft 116 is received in and extends through bearings 224 and 225. Preferably, bearing 224 includes ball bearings (and provides radial support) and bearing 225 includes needle bearings (and provides radial support, but can withstand higher temperatures). The pinion coupling assembly 216 is housed in motor mount 250, which is connected to the motor 106 and through which the motor shaft 248 extends. The motor mount 250 is connected to the gear box mount 252, as shown in FIG. 9.

Figure 8:
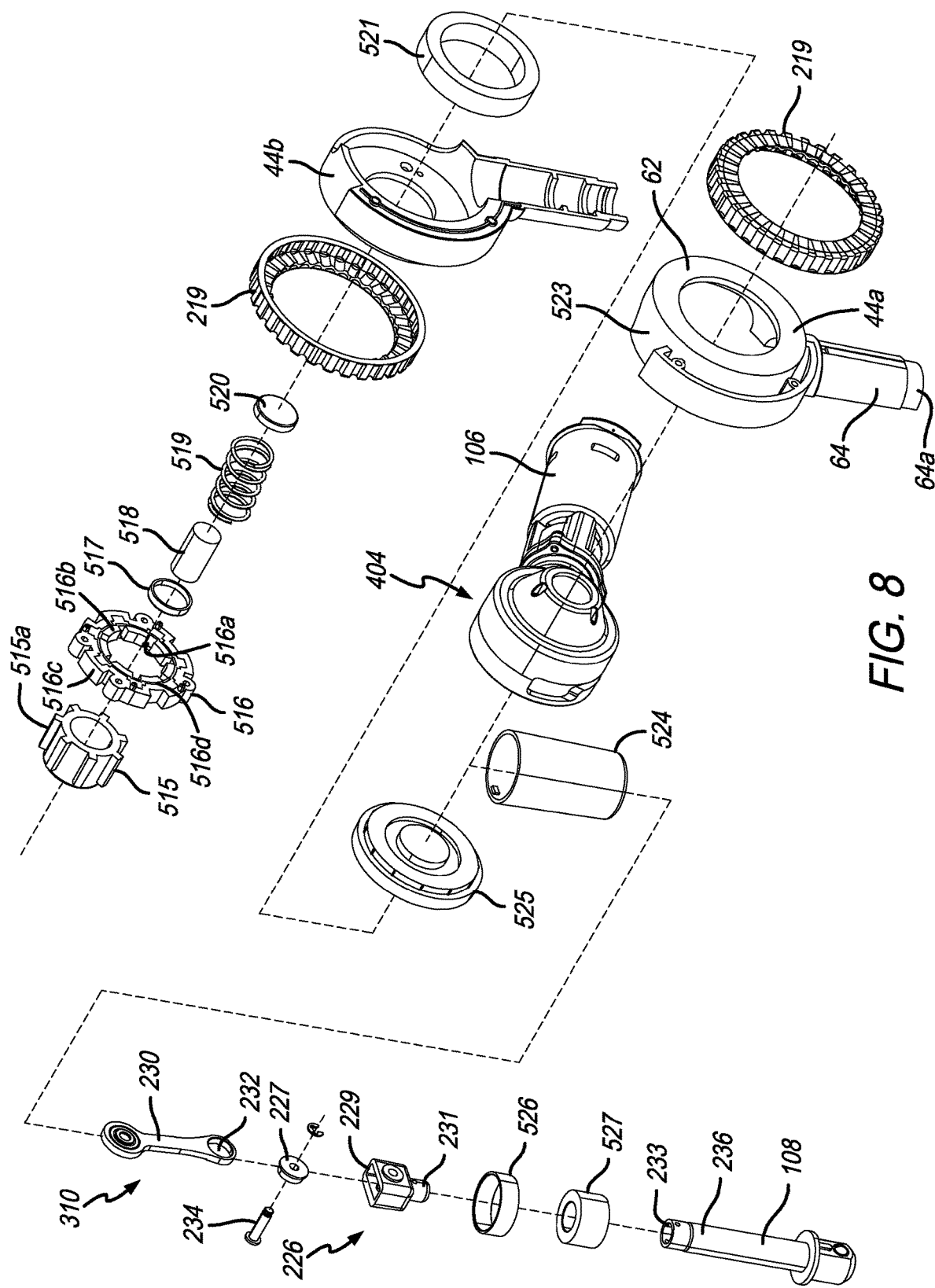
FIG. 8 is another an exploded perspective view of a portion of the percussive massage device.
Figure 9:
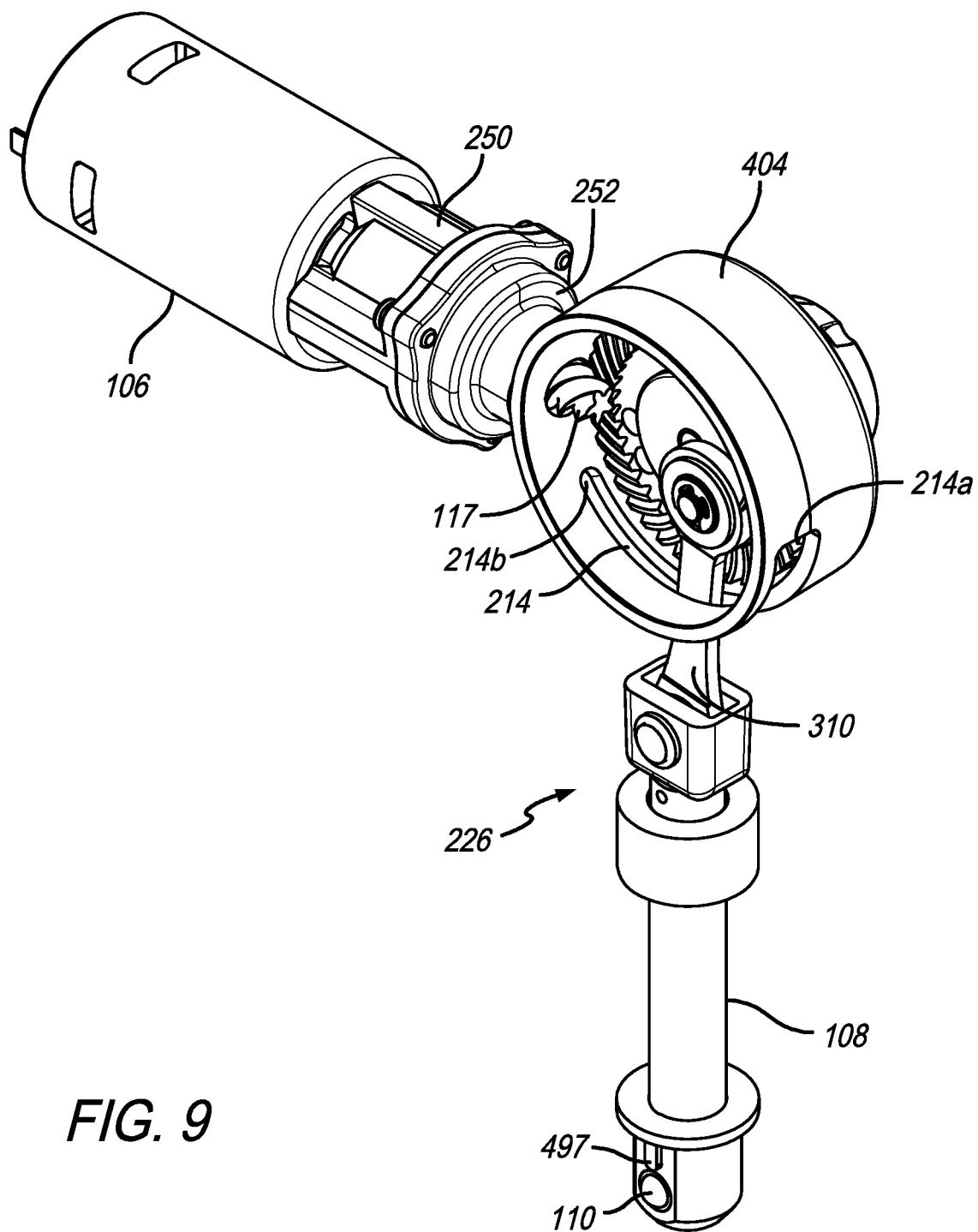
FIG. 9 is a perspective view of the drive train components of the percussive massage device.

As shown in FIGS. 7-9, the gearbox 404, in one embodiment, includes the gear member 304 and the reciprocator or push rod 310. Preferably, the gear member 304 includes a shaft 246 extending therefrom to which the reciprocator 310 is connected. The gearbox 404 may provide mounting points for the gear member 304 and the reciprocator 310. The gearbox 404 may restrict the motion of the gear member 304 and the reciprocator to certain directions or rotational axes. The gearbox 404 may be mounted to the housing 101. In some embodiments, the gearbox 404 is separated from the housing 101 by the one or more compliant dampening blocks.

As shown in FIGS. 6 and 8, in a preferred embodiment, to prevent the gearbox from transmitting vibrations to the housing a rubber cover can be provided. Further inner suspension rings 219 isolate vibration of the gearbox from handle and the treatment structures. Preferably, the rings 219 are made of an elastomer and act as a cushion to dampen vibrations between the rotation housing and the housing 101. In a preferred embodiment, the inner suspension rings 219 surround the outer radial surface of the main body portion 62 (see seat surface 523 in FIG. 8).

In one embodiment, rotation of the actuated output or shaft 108 may be selectively locked and unlocked by a user. For example, the user may unlock rotation of the shaft 108, rotate the actuated output 108 to a desired position relative to the housing 101, lock rotation of the actuated output 108, and operate the reciprocating treatment device 100. FIG. 8 shows the components that allow rotation of the rotation housing 44 together with the push rod assembly 108 and related components. Button 515 includes radially extending teeth 515a and is biased outwardly by spring 519, which surrounds and is seated on spacer 518 (which is preferably made of foam). Spring 519 is seated against dampening members 520 and 517, which are preferably made of rubber to dampen any vibrations of the spring 519. The assembly also includes a gear box cover 525 and dampening ring 521. Button 515 is outwardly biased by spring 519 to a position where teeth 515a are engaged with teeth 516a, which are defined hoop 516, which is connected to housing 101.

Figure 2:
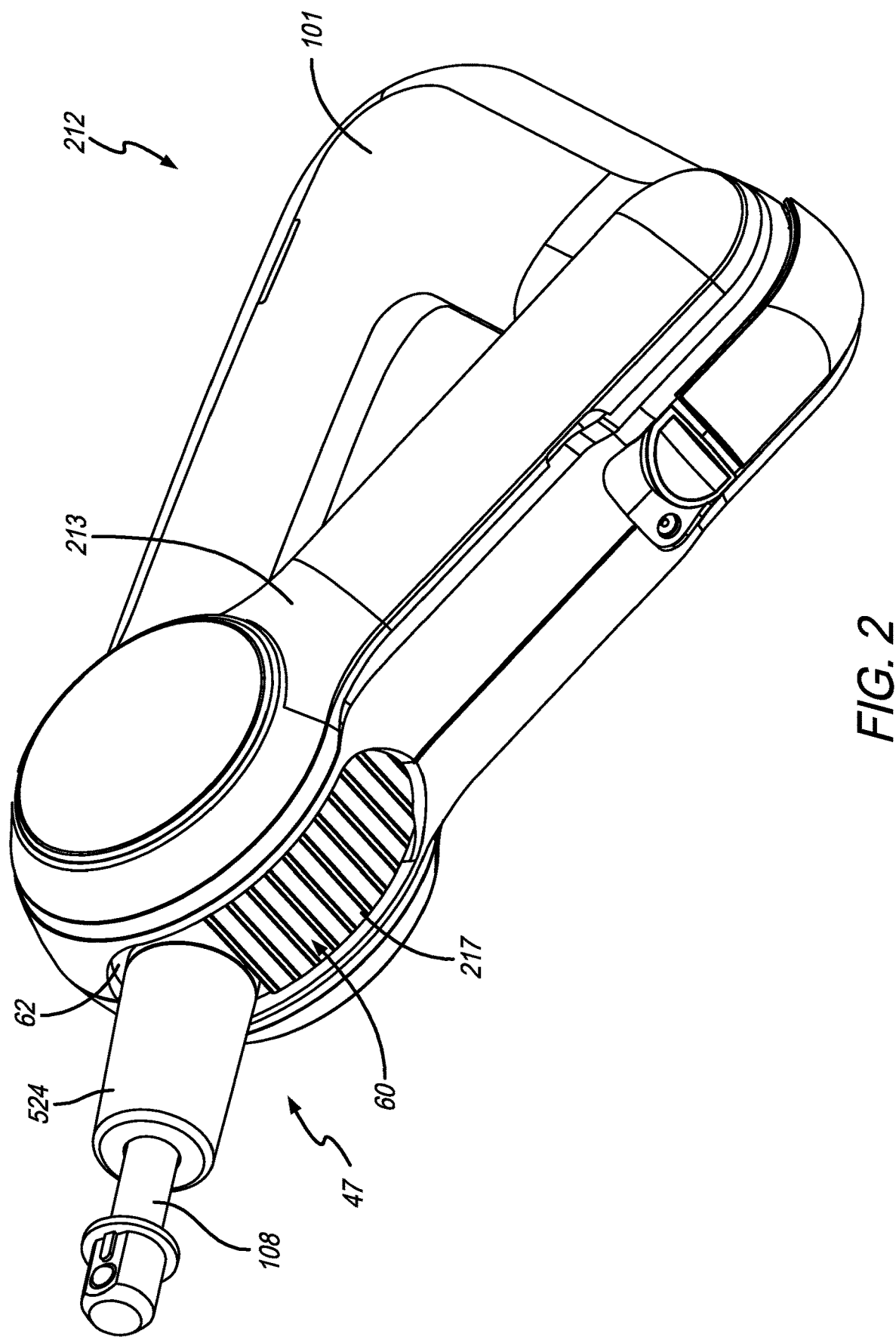
FIG. 2 is a perspective view of the percussive massage device.

Preferably hoop 516 includes inner and outer plastic rings 516b and 516c that sandwich a rubber ring 516d therebetween to help dampen vibrations and reduce noise. The button 515 is movable between a first position where teeth 515a are engaged with teeth 516a and a second position where teeth 515 are not engaged with teeth 516a. When the button 515 is in the first position, the rotation assembly 47 cannot rotate. When the button is pushed to the second position, the teeth 515a disengage from teeth 516a, thereby allowing the entire rotation assembly 47 to rotate. The rotation housing 44 includes a main body portion 62 disposed in the housing and an arm portion 64 extending through the rotation space 60 and outside the housing. The arm portion 64 rotates within the rotation space 60 defined in the housing 101. As shown in FIG. 2, in a preferred embodiment, the device 212 includes a tambour door 217 that unfolds within the rotation space 60 as the rotation assembly is moved from the position shown in FIG. 1 to the position shown in FIG. 2. The tambour door 217 covers slot 214. As shown in FIG. 2, an arm cover 524 covers the arm portion 64 of the rotation housing 44.

As shown in FIG. 9, the gearbox housing 404 includes a clearance slot 214 defined therein for the push rod assembly 108. The slot 214 is provided so the push rod assembly 108 can move freely and allow the rotation housing 44 to articulate. The clearance slot 214 has first and second ends 214a and 214b. As shown in FIG. 9, the push rod assembly 108 extends through the clearance slot 214. it will be appreciated that when the rotation housing 44 is rotated from a first position to a second position the push rod assembly 108 moves within the clearance slot 214 from the first end to the second end thereof.

Figure 10:
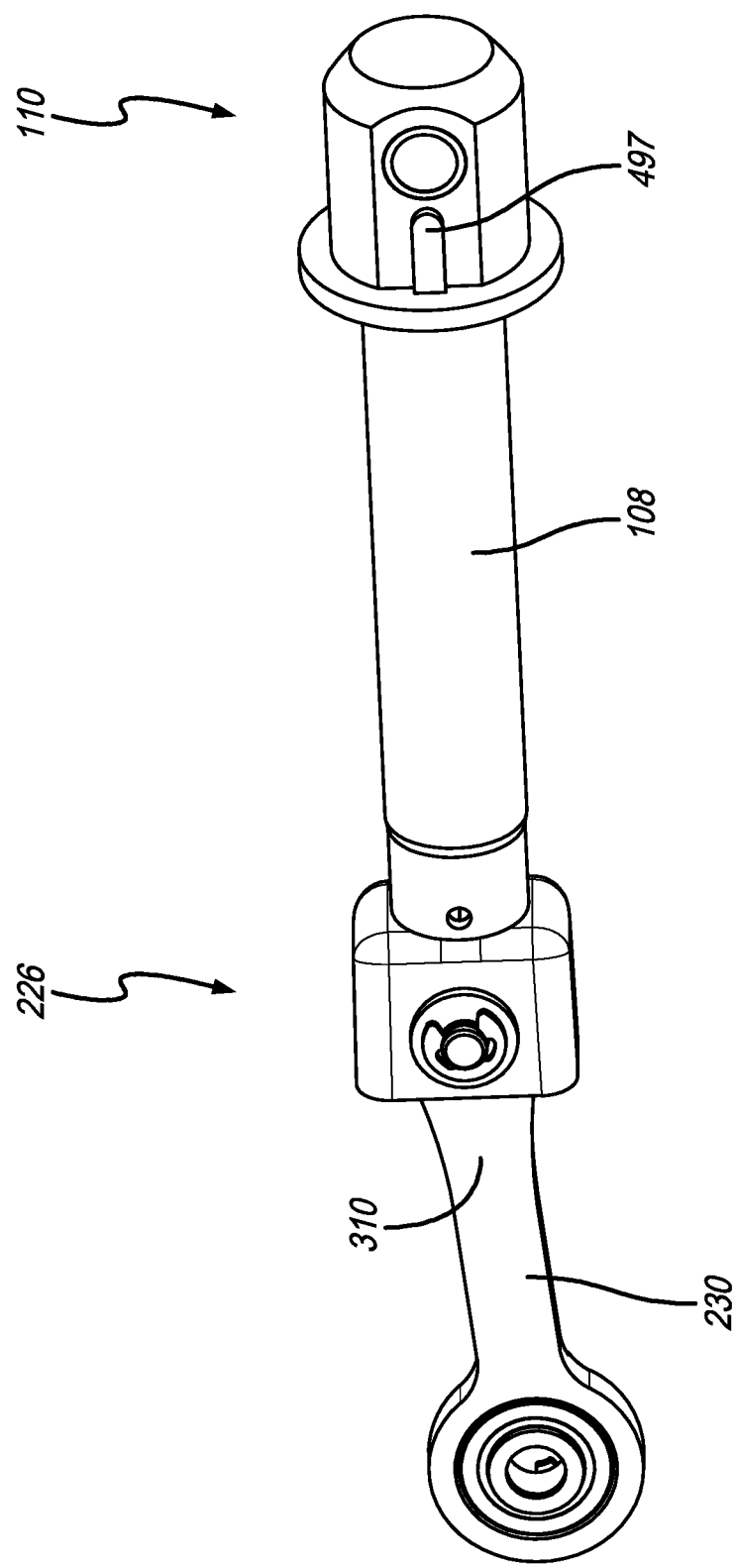
FIG. 10 is a perspective view of the push rod assembly of the percussive massage device.
Figure 11:
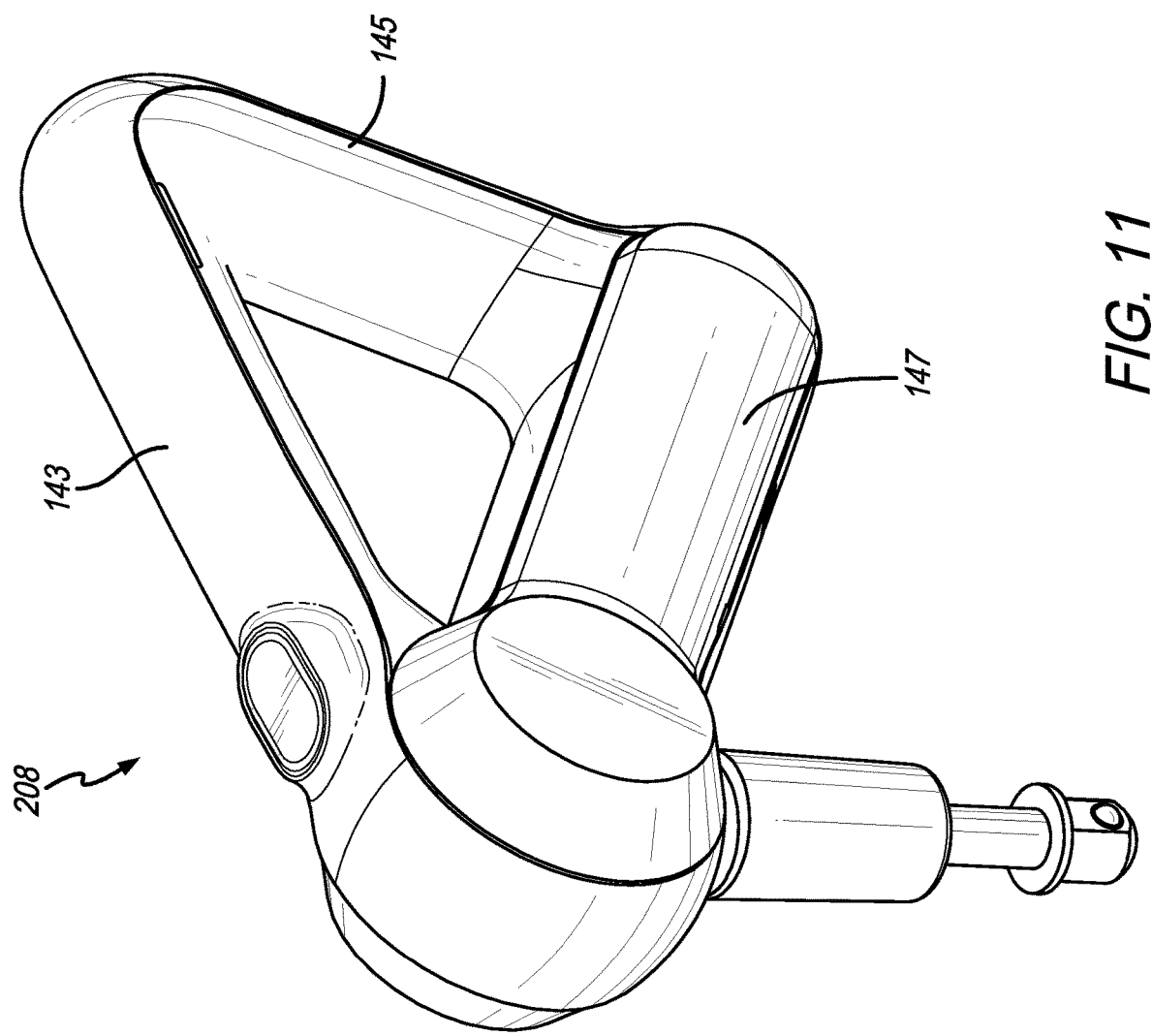
FIG. 11 is a perspective view of another percussive massage device.
Figure 12:
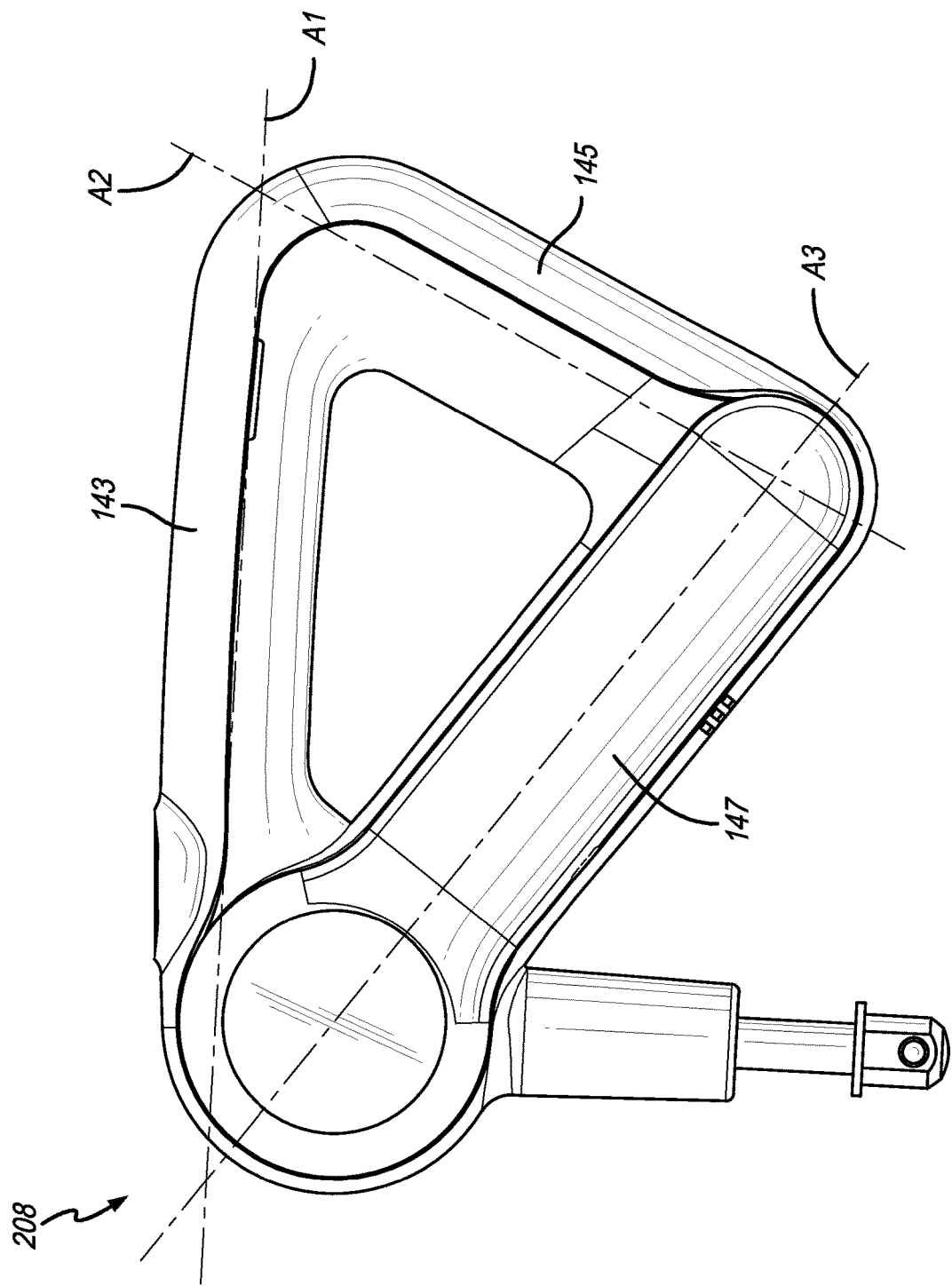
FIG. 12 is a side elevational view of the percussive massage device of FIG. 11.

As shown in FIGS. 8-10, in a preferred embodiment, the pushrod assembly or output shaft 108 includes two halves or rods with an adapter member 226 therebetween to also help reduce noise and vibration. The adapter member 226 isolates the vibrations generated in the gearbox and prevents them from being transmitted down the shaft to the treatment structure. The adapter member 226 can include anti-rotation tabs to protect the push rod from user applied torque during use. The first rod portion 230 of the output shaft 108 (push rod or reciprocator 310) includes an opening 232 on an end thereof that receives a pivot pin 234. The connection between the first rod portion 230 and the adapter member 226 includes a bushing 227 with the pin 234 and elastomeric material to dampen vibrations. The end of first rod portion 230 that includes opening 232 is received in a pocket 229 in adapter member 226. The pin 234 extends through openings in the side walls of adapter member 226, through bushing 227 and through opening 232, to secure first rod portion 230 to adapter member 226. Adapter member 226 includes a protrusion 231 extending therefrom that is received in an opening 233 in an end of the second rod portion 236, to connect the adapter member 226 to the second rod portion 236. In another embodiment, the end of the second rod portion 236 can be received in an opening in the adapter member 226. In use, the size of the top opening of pocket 229 allows the first rod portion to move side to side as the opening 232 pivots on pin 234 and first rod portion 230 reciprocates. This translates to linear reciprocation of second rod portion 236. Because the bushing 227 comprises at least some elastomeric material, vibrations are dampened (and noise reduced) as the push rod assembly 108 reciprocates.

Ring 526 is seated on and surrounds the bottom portion of the arm portion 64 (see seat 64a in FIG. 8) to help hold the first and second housing halves 44a and 44b together. Washer or guide member 527 is received in the rotation housing 44 and provides stability and a path for the reciprocating push rod assembly or output shaft 108.

As shown in FIG. 9, in this embodiment, the first rod portion 230 or push rod assembly 108 extends through clearance slot 214. It will be appreciated that the term pushrod assembly includes any of the embodiments described herein and can include a shaft with an adapter member allowing pivoting between two halves or can include a single shaft that does not include any pivoting.

As shown in FIGS. 9-10, in a preferred embodiment, the male connector 110 includes an alignment tab 497 above each ball that mates with a slot in the female opening. These tabs 497 help with proper alignment with the treatment structure. See U.S. Patent App. No. 2019/0017528, the entirety of which is incorporated herein by reference.

Figure 13:
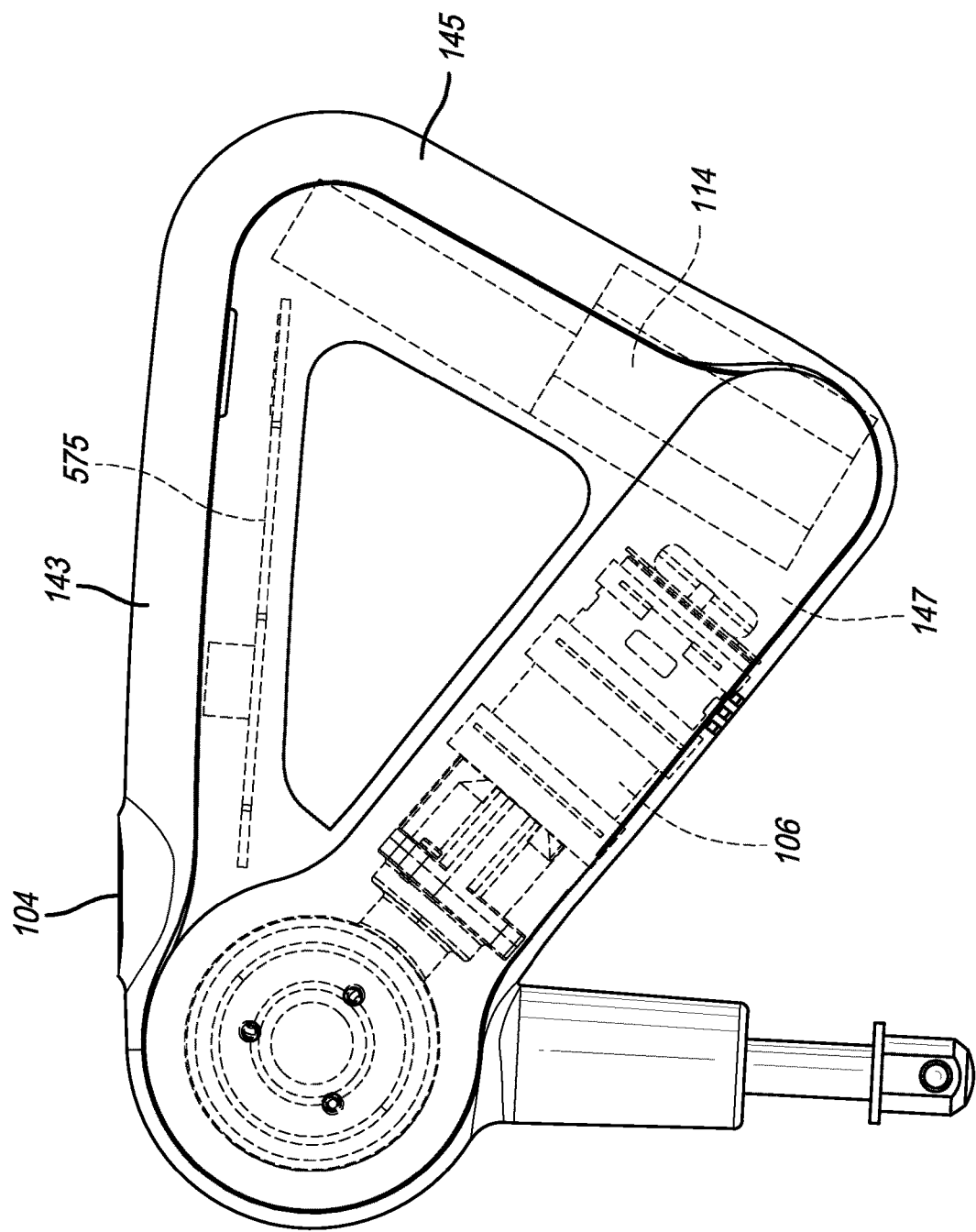
FIG. 13 is a side elevational view of the percussive massage device showing some internal components in hidden lines.
Figure 14:
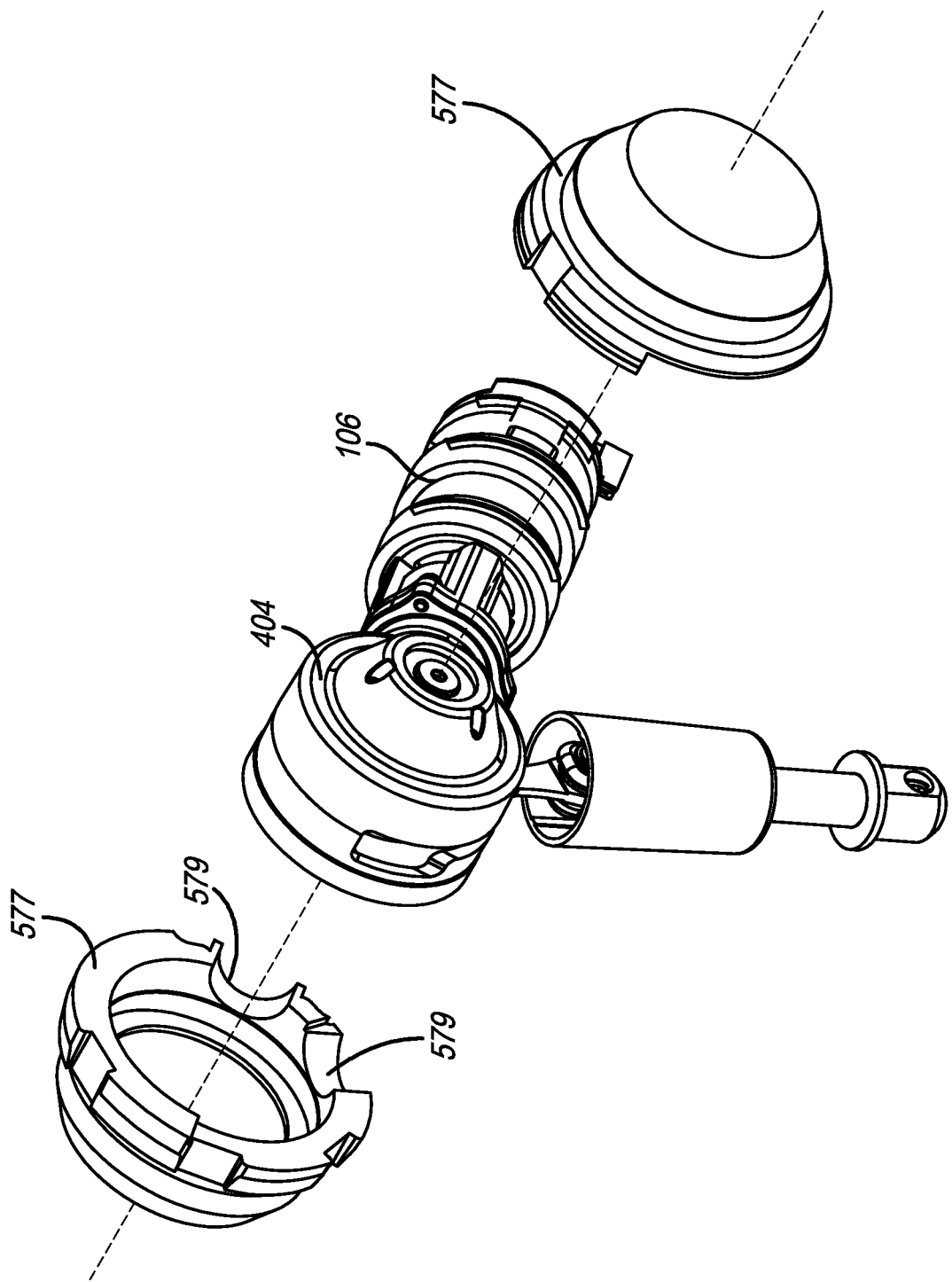
FIG. 14 is an exploded perspective view of some of the internal components of the percussive massage device.
Figure 15:
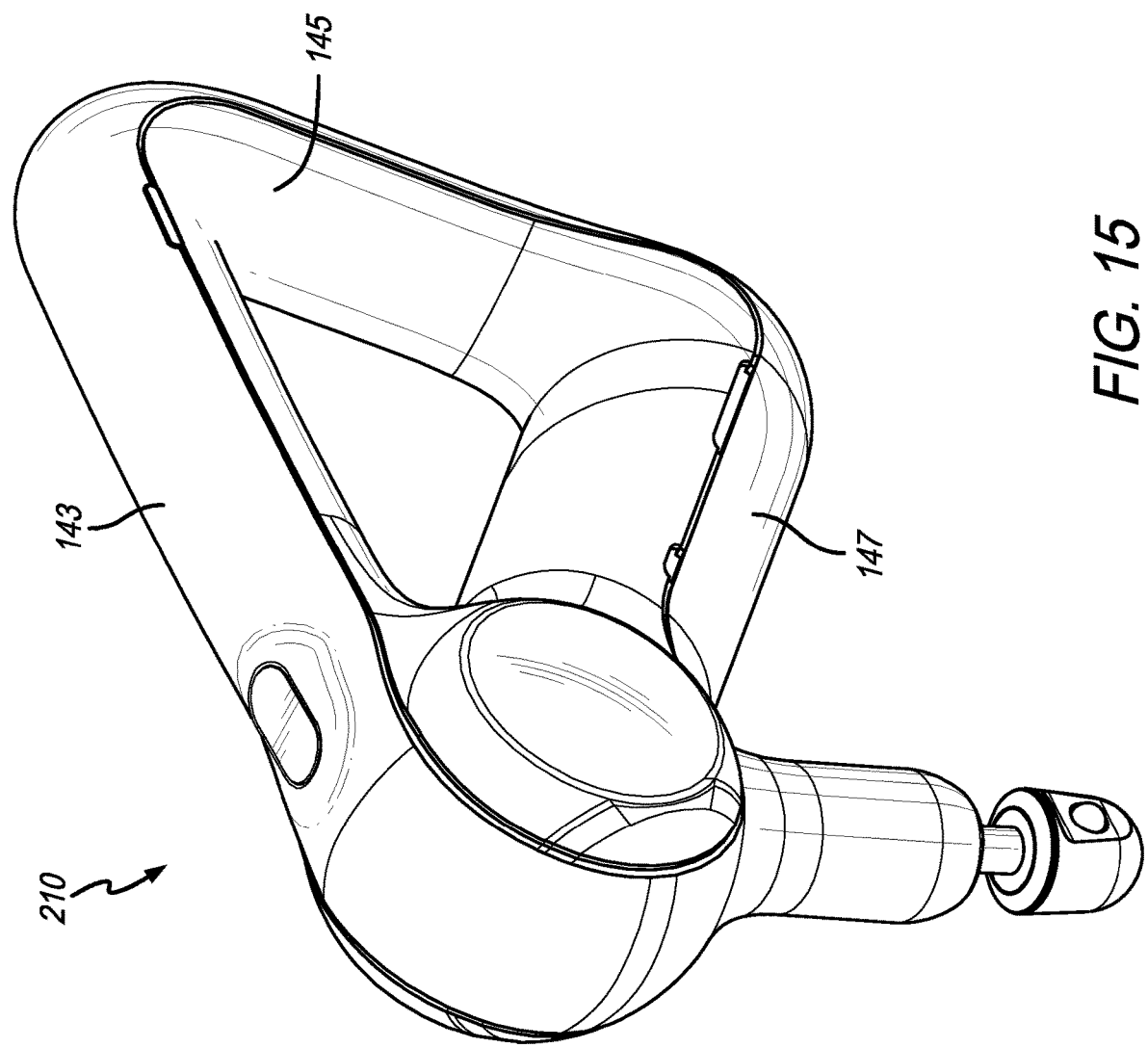
FIG. 15 is a perspective view of another percussive massage device.
Figure 16:
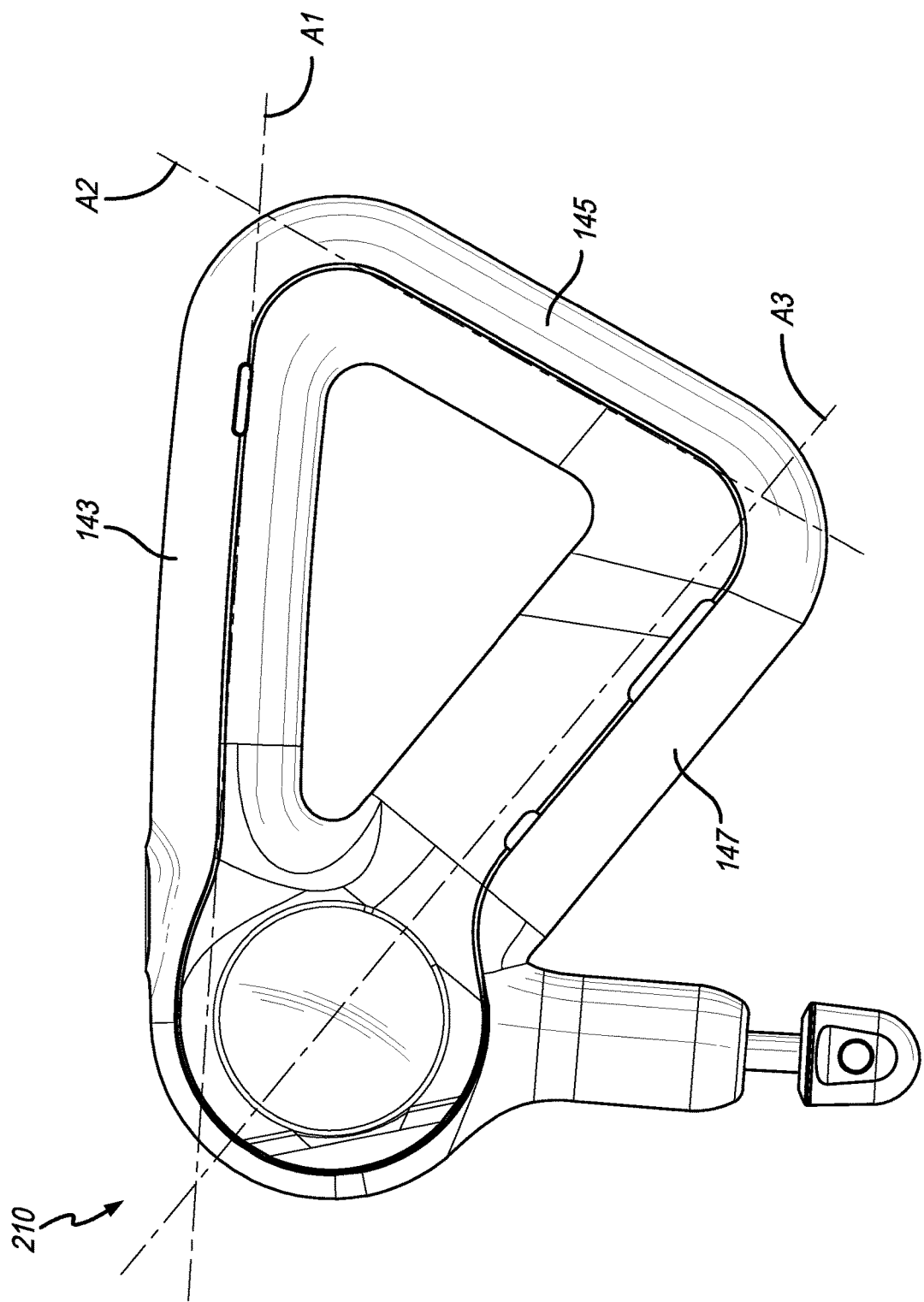
FIG. 16 is a side elevational view of the percussive massage device of FIG. 15.

FIGS. 11-16 show embodiments of percussive massage devices similar to percussive massage device 212 above, but without a rotation assembly. Device 208, shown in FIGS. 11-14 is referred to commercially as the G3. Device 210, shown in FIGS. 15-16 is referred to commercially as the LIV. As is shown in FIG. 13, in a preferred embodiment, switch 104 includes switch electronics 575 associated therewith. The switch electronics 575 may include a printed circuit board (PCB) and other components to allow the switch 104 to activate the motor 106 and to change the speed of the motor, turn the device on and off, among other tasks. As shown in FIG. 13, in a preferred embodiment, the motor 106 is housed in the third handle portion 147, the battery 114 is housed in the second handle portion 145 and the switch electronics 575 are housed in the first handle portion 143. This configuration also applies to devices 210 and 212. FIG. 14 shows cushion members 577 that surround the gearbox 404 and help dampen and reduce noise and vibration generated by the components in the gearbox. Cushion members 577 are similar to inner suspension rings 219 in device 212. However, cushion members 577 are thicker and do not need to rotate due to the exclusion of the rotation housing in devices 208 and 210. Cushion members 577 include cutouts or channels 579 therein to allow clearance of components such as the push rod assembly and pinion shaft.

Figure 17:
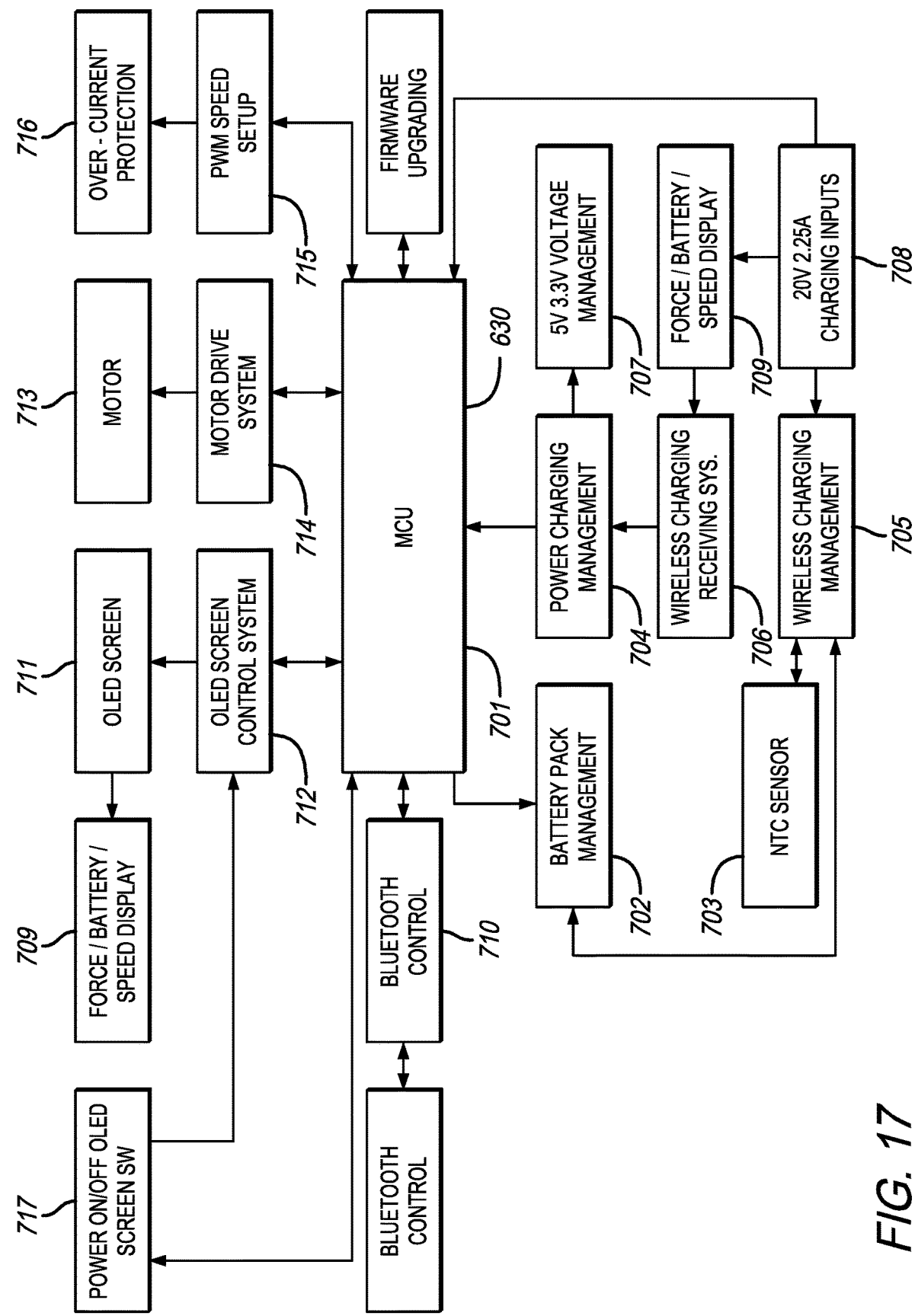
FIG. 17 is a block diagram showing interconnected components of a percussive massage device with a force meter.

FIGS. 17-35 show embodiments in accordance with a percussion massage device with a force meter. FIG. 17 is a block diagram showing interconnected components of a percussive therapy device with a force meter 400 (see also FIG. 33). In an embodiment, the percussive therapy device with force meter 400 includes a microcontroller unit 701, a battery pack management unit 702, an NTC sensor 703, a power charging management unit 704, a wireless charging management unit 705, a wireless charging receiving system 706, a voltage management unit 707 (5V 3.3V Voltage Management in drawings), battery charging inputs 708 (20V 2.25 A Charging Inputs in drawings), a display 709 (Force/Battery/Speed Display in drawings), a wireless control unit 710 (Bluetooth Control in drawings), an OLED screen 711, an OLED screen control system 712, a motor 713, a motor drive system 714, a PWM speed setup unit 715, an overcurrent protection unit 716, and a power switch unit 717 (Power On/Off OLED Screen SW in drawings). In the embodiment shown in accordance with FIG. 17, each block in the diagram is shown as a separate component. In alternative embodiments, however, certain components may be combined without departing from the scope of the present disclosure.

The microcontroller unit 701, in an embodiment, is a microcontroller unit including a processor, a memory, and input/output peripherals. In other embodiments, however the microcontroller unit 701 is an ST Microelectronics STM32F030K6 series of microcontroller units, STM32F030C8T6 series of microcontrollers, STM32F030CCT6 series of microcontrollers, or an equivalent microcontroller.

One of ordinary skill would understand that the memory of the microcontroller unit 701 is configured to store machine-readable code for processing by the processor of the microcontroller unit 701. Various other configurations may exist depending on whether the designer of the percussive massage device with force meter 400 desires to implement the machine-readable code in software, firmware, or both. In an embodiment, the machine-readable code is stored on the memory and configured to be executed by a processor of the microcontroller 701. In an embodiment, the machine-readable code is stored on computer-readable media.

The battery pack management unit 702, in an embodiment, is implemented in firmware or software and configured to be used in connection with the microcontroller unit 701. In this embodiment, the firmware or software is stored in memory (not shown) and configured to be obtainable by the microcontroller unit 701. The battery pack management unit 702 may also be a combination of firmware, software, and hardware, in another embodiment. The battery pack management unit 702 is coupled with the NTC sensor 703. The NTC sensor 703 is a negative temperature coefficient thermistor used by the battery pack management unit 702 to sense temperature of the battery pack. For example, the NTC sensor 703 is a thermistor with B value of 3950+/−1%, and a resistance of 10 kΩ. In another example, the thermistor has a resistance of 100 kΩ. One of ordinary skill in the art would recognize that a thermistor is a resistor whose resistance is dependent upon temperature. In other embodiments, however, the NTC sensor 703 may be another type of temperature sensing device or component used in connection with the battery pack management unit 702.

The power charging management unit 704, in an embodiment, is implemented in firmware or software and configured to be used in connection with the microcontroller unit 701. Similarly to the battery pack management unit 702, the power charging management unit 704 firmware or software is stored in memory (not shown) and configured to be obtainable by the microcontroller unit 701. The power charging management unit 704 may also be a combination of firmware, software, and hardware, in another embodiment. In various embodiments, the power charging management unit 704 is configured to charge a battery pack via a direct connection or through an external charger, such as when configured to be operable with rechargeable batteries.

The wireless charging management unit 705, in an embodiment, is coupled to the battery pack management unit 702 and the battery charging inputs 708. In other embodiments, the battery or battery pack is charged using other conventional methodologies, such as, for example, charging the battery or battery pack using a wire or cord coupled to the battery charging inputs 708.

The wireless charging receiving system 706, in an embodiment, is coupled to the power charging management unit 704 and the display 709. The wireless charging receiving system 706 includes one or more of firmware, software, and hardware. In an embodiment, the wireless charging receiving system 706 is configured to receive information pertaining to battery capacity, charging metrics, and other information pertaining to wireless charging, and to pass along the information to the power charging management unit 704. The wireless charging receiving system 706 preferably includes a wireless charging pad used to charge the percussive massage device with force meter 400. One of ordinary skill in the art would understand that a variety of wireless charging devices may be utilized to wirelessly charge the percussive massage device with force meter 400. As one example, the Qi wireless charging standard and related devices may be utilized to wirelessly charge the percussive massage device with force meter 400.

The voltage management unit 707, in an embodiment, is a DC voltage regulator that steps down 5 volt to 3.3 volt power for use by the microcontroller unit 701. The voltage management unit 707 may also perform additional functions for management of 3.3 volt power for use by the microcontroller unit 701. In an embodiment, the voltage management unit 707 is implemented using a series of electronic components such as, for example, implementing a resistive divider using electronic components. In another embodiment, the voltage management unit 707 is a stand-alone voltage regulator module and/or device designed to step down voltage from 5 volts to 3.3 volts. One of ordinary skill in the art would understand the various methodologies and devices available to step down 5 volts to 3.3 volts.

The battery charging inputs 708, in an embodiment, are interfaces by which a wire or cord may be inserted for charging the percussive massage device with force meter 400. For example, a standardized barrel connector is the battery charging inputs 708. In another example, the battery charging inputs 708 is a USB connector. Other more specialized charging methodologies may require a particular battery charging input not described above.

The display 709, in an embodiment, displays a series of LEDs depicting an amount of force applied by the percussive massage device with force meter 400. In an alternative embodiment, the display 709 displays a series of LEDs depicting the current battery or battery pack charge of the percussive massage device with force meter 400. In yet another embodiment, the display 709 displays a series of LEDs depicting the current speed of the percussive massage device with force meter 400. One of ordinary skill in the art would recognize that while LEDs have been specified in the above-referenced embodiments, other embodiments not using LEDs are within the scope of this disclosure, such as, for example, liquid crystal displays, OLEDs, CRT displays, or plasma displays. One of ordinary skill in the art would also understand that it may be advantageous in an embodiment utilizing a battery or battery pack to use low-power options to ensure battery power longevity. In an embodiment, the display 709 is a 128×64 pixel OLED display.

The wireless control unit 710 is a wireless connectivity device that may be implemented in a wireless microcontroller unit. In an embodiment, the wireless control unit 710 is a Bluetooth transceiver module configured to couple, via Bluetooth, to a remote device. In an embodiment, the Bluetooth module is a Bluetooth Low-Energy (BLE) module configured to be run in broadcast mode. The wireless control unit 710 is coupled to the microcontroller unit 701. In an embodiment, the remote device is a smartphone having an embedded Bluetooth module. In an alternative embodiment, the remote device is a personal computer having Bluetooth connectivity. In other embodiments, other wireless connectivity standards besides the Bluetooth wireless standard may be utilized. It will be appreciated that the Bluetooth connectivity or other wireless connectivity may be described herein as being implemented in a wireless connection device. The wireless connection device can be a separate module, can be included in the MCU or other component of the device, or can be a separate chip. In summary, the percussive therapy device including a wireless connection device means that the percussive massage device can connect to another electronic device wirelessly (e.g., a phone, tablet, computer, computer, voice controlled speaker, regular speaker, etc.). One of ordinary skill in the art would recognize that low-power wireless control modules may be advantageous when the percussive massage device with force meter 400 is utilizing a battery or battery pack.

The OLED screen 711 and the OLED screen control system 712, in an embodiment, are configured to display substantially the same information as the display 709 referenced above. The OLED screen 711 is coupled to the OLED screen control system 511. The OLED screen control system 712 is coupled to the microcontroller unit 701, the OLED screen 711, and the power switch unit 717. In an embodiment, the display 709 and the OLED screen 711 may be redundant and it may only be necessary to utilize one or the other.

The motor 713, in an embodiment, is a brushless direct current (BLDC) motor. The motor 713 and the motor drive system 714, in an embodiment, are configured to vary the speed (i.e., rotational motion) that may be converted to reciprocal motion. In other embodiments, the motor 713 is a brushed DC motor, a brushed AC motor, or a brushless AC motor. One of ordinary skill in the art would understand that choosing a brushless or brushed motor, or direct current or alternating current, may vary depending on the application and intended size, battery power, and use.

The PWM speed setup unit 715, in an embodiment, is used to control pulse width modulation utilized to drive the motor 713. The PWM speed setup unit 715 is coupled to the microcontroller unit 701 and the over-current protection unit 716. One of ordinary skill in the art would understand that pulse width modulation is one way to vary the average power applied to the motor 713, resulting in varying speed as desired. In alternative embodiments, one of ordinary skill in the art would understand that there are a variety of methods to vary the speed of a brushless DC motor. For example, voltage to the motor 713 may be controlled in other non-PWM methods.

The over-current protection unit 716, in an embodiment, may be a feature of an integrated system-in-package to prevent damage caused by high currents to the motor. In other embodiments, the over-current protection unit 716 is implemented using a series of electronic components configured to protect the motor from excessively high current.

The power switch unit 717, in an embodiment, is configured to turn on and turn off the percussive massage device with force meter 400. The power switch unit 717 is coupled to the OLED screen control system 712 and the microcontroller unit 701. In an embodiment, the power switch unit 717 is the switch 405.

Figure 18:
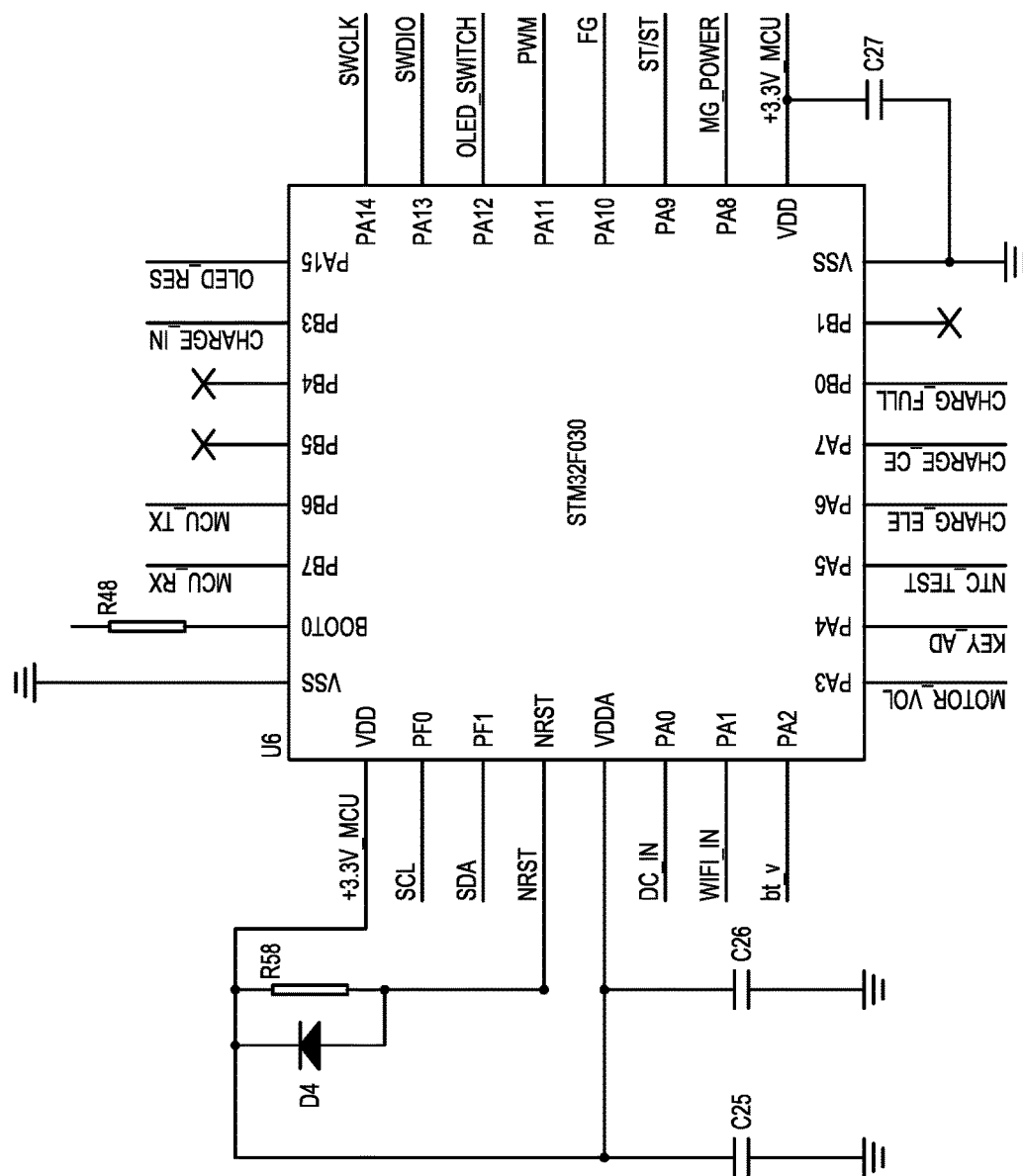
FIG. 18 is a circuit diagram of a microcontroller unit with pin outputs in accordance with one embodiment.

FIG. 18 shows a circuit diagram of the microcontroller unit 701 with pin outputs. In this embodiment, the STM32F030K6 series of microcontroller units is utilized. The circuit diagram depicts +3.3 volt power being provided to the VDD inputs of the microcontroller unit 701. Input PA3 is labeled "Motor_VOL", the voltage of the motor 713. Input PA2 is "bt_v", the battery or battery pack voltage. The microcontroller unit is configured to receive analog voltage on inputs PA2 and PA3 and to convert it to digital voltage using the microcontroller's analog-to-digital converter. In this embodiment, the analog-to-digital converter is a 12-bit ADC. One of ordinary skill in the art would understand that other microcontrollers may utilize voltage sensing and analog-to-digital converters to perform similar functions. In yet other embodiments, an analog-to-digital converter module separate from a microcontroller may be utilized.

Figure 19:
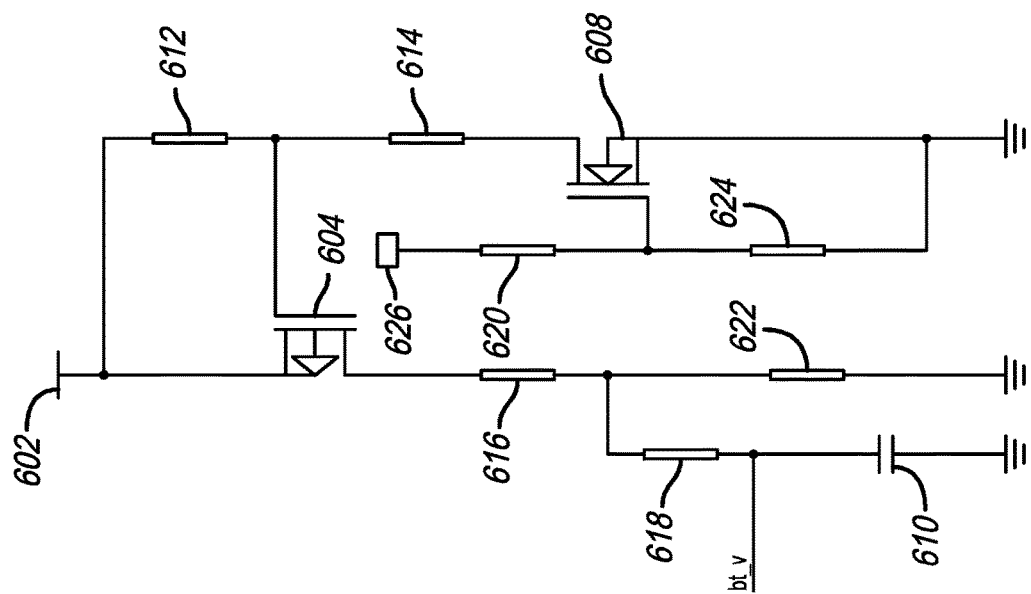
FIG. 19 is a circuit diagram used for battery voltage detection in accordance with one embodiment.

FIG. 19 shows a circuit diagram used for battery voltage detection. In this embodiment, +BT, the positive battery terminal 518, is coupled to a circuit consisting of a P-channel MOSFET 519, an N-Channel MOSFET 520, 0.1 µF capacitor 521, 100 kΩ resistors 522, 523, 68 kΩ resistor 524, 1 kΩ resistors 525, 526, and 10 kΩ resistors 527, 528. The circuit is configured to provide an input analog voltage of the battery or battery pack, or bt_v, to the microcontroller unit 701 of FIG. 18. In other embodiments, voltage of the battery or battery pack may be achieved using a voltage reader coupled to the terminals of the battery or battery pack.

Figure 20:
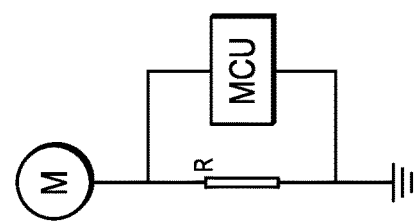
FIG. 20 is a circuit diagram for detection and measurement of voltage of the motor of the percussive massage device in accordance with one embodiment.

FIG. 20 shows a circuit diagram for detection and measurement of voltage of the motor 713 of the percussive massage device. In this embodiment, voltage sensing resistor 529 is coupled in parallel with the microcontroller unit 701, and coupled to the motor 713. In an embodiment, the voltage sensing resistor has a value of 0.0025Ω. The circuit depicted in FIG. 20 is configured to provide the Motor_VOL input into the microcontroller unit 701 of FIG. 17. In an embodiment, the input analog voltage is amplified. In another embodiment, the voltage of the motor 713 is measured or sensed using a separate series of electronic components or a standalone device and input into a microprocessor for use with the method of displaying a force on the percussive massage device.

Figures 21, 22:
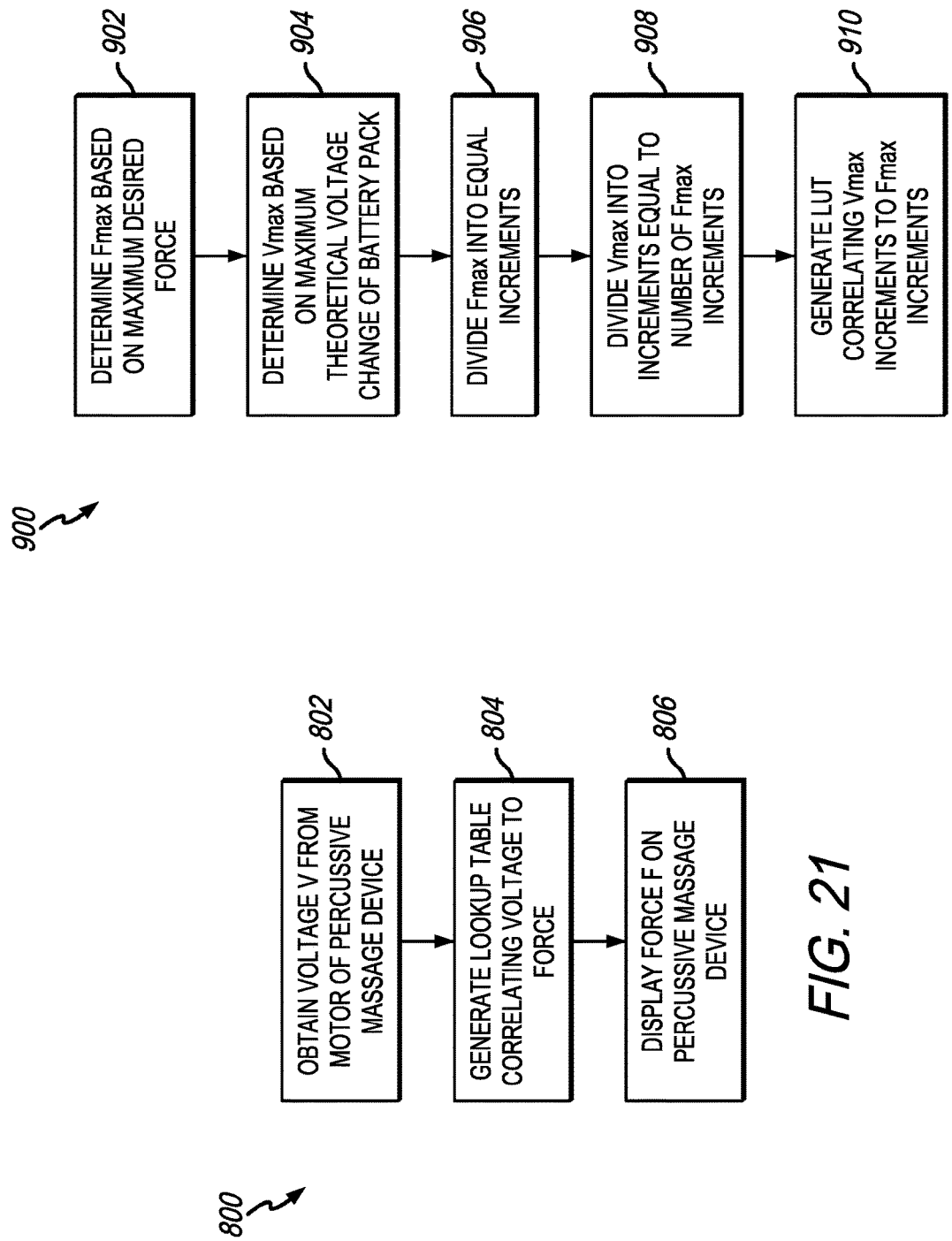
FIG. 21 is a flow diagram showing a method of detecting force applied by the percussive massage device in accordance with a preferred embodiment.
FIG. 22 is a flow diagram showing a method of generating a lookup table correlating voltage to force in accordance with a preferred embodiment.

FIG. 21 is a flow diagram showing a method 800 of detecting force applied by the percussive massage device in accordance with a preferred embodiment. At Step 802, a voltage magnitude V is obtained. In an embodiment, voltage magnitude V is an analog voltage obtained by using the circuit disclosed in FIG. 17. In that circuit, a block curve signal from the motor 713 (i.e., a Hall effect sensor) is simulated in the circuit as current using the resistor R, which is placed in parallel with the microcontroller unit 701. In other embodiments, voltage that corresponds to the current operating speed of the motor 713 may be generated in a variety of other ways. The voltage magnitude V may be input to a microcontroller unit 701 that converts analog voltage to digital voltage using an analog-to-digital converter, such as that implemented in the STM32F030K6 microcontroller unit. The STM32F030K6 microcontroller unit coverts analog voltage magnitude to a digital code corresponding to the 12-bit ADC (i.e., 0 to 4096). The digital code represents a voltage magnitude corresponding to the original voltage magnitude V obtained.

At Step 804, a lookup table is generated that correlates voltage V to force magnitude F. In an embodiment, the lookup table is generated using a method 900 of generating a lookup table correlating voltage to force. For example, the force magnitude F may be expressed in pounds of force. In an alternative embodiment, the force magnitude F may be expressed in Newtons of force.

At Step 806, the force magnitude F corresponding to voltage magnitude V is displayed on the percussive massage device with force meter 400. In an embodiment, a series of LED lights may be utilized to depict varying amounts of force as the force is being applied by the percussive massage device with force meter 400. Thus, as the amount of force magnitude F increases, more LEDs on the series of LED lights will be lit. Preferably, the series of LED lights consists of 12 LED lights.

FIG. 22 is a flow diagram showing a method 900 of generating a lookup table correlating voltage to force. At Step 902, a maximum magnitude of force, Fax, is determined. The magnitude of $F_{MAX}$ may be determined by assessing the maximum desired force to apply using the percussive massage device with force meter 400. As an example, $F_{MAX}$ is 60 pounds of force.

At Step 904, a maximum magnitude of voltage, $V_{MAX}$, is determined. The magnitude of $V_{MAX}$ may be determined by assessing the maximum theoretical voltage change possible by the percussive massage device with force meter 400. As an example, $V_{MAX}$ is 1.8 volts.

At Step 906, $F_{MAX}$ is divided into equal increments. Using the above example from Step 902, 60 pounds of force is divided into 60 one-pound increments.

At Step 908, $V_{MAX}$ is divided into the same amount of increments as determined in Step 906 above. Thus, using the above example from Step 904, 1.8 volts is divided into 60 0.03-volt increments.

Figure 23:
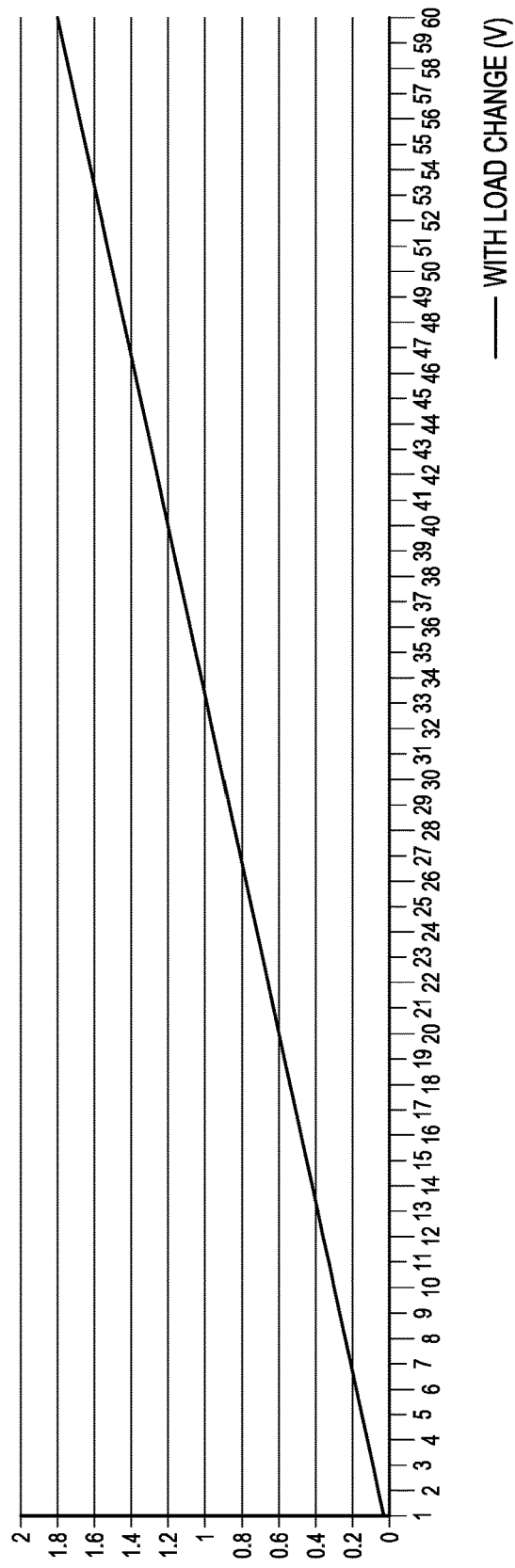
FIG. 23 is a graph plotting a lookup table for use by a method of detecting force applied by the percussive massage device that was generated by correlating voltage to force in accordance with a preferred embodiment.

At Step 910, a lookup table (LUT) is generated that correlates the increments of pounds of force with the increments of voltage. This necessarily creates a linear relationship between force and voltage. FIG. 23 is a graph plotting the LUT for use by the method of detecting force of FIG. 21 that was generated using the specific example identified in FIG. 22. The graph depicts calculated force that was calculated using the method 900.

A problem may arise in that the theoretical maximum voltage assumption at Step 904 in the method 900 is inaccurate. It may also be the case that as the percussive massage device with force meter 400 is used, the maximum available voltage degrades over time. In other words, the battery or battery pack voltage may decrease.

Figure 24:
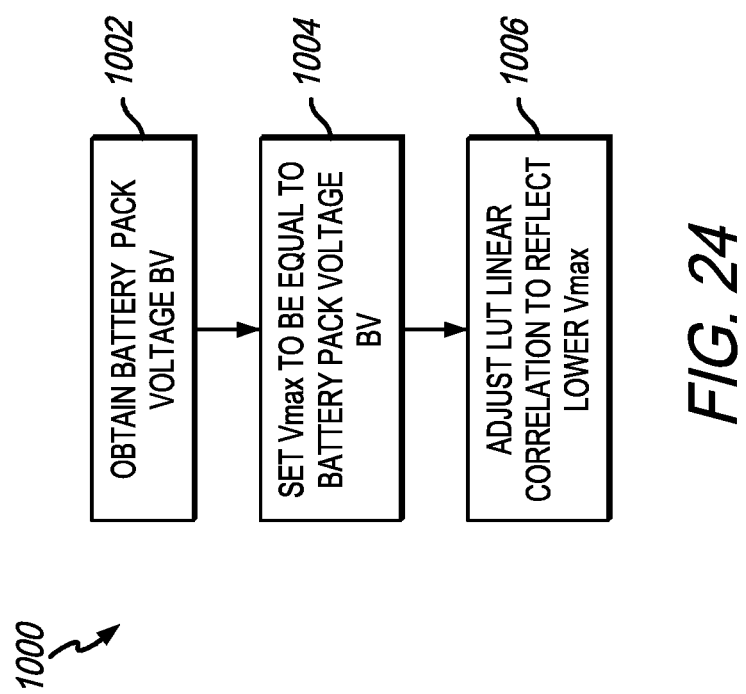
FIG. 24 is a flow diagram showing a method of calibrating a lookup table according to a preferred embodiment.

Accordingly, a method 1000 of calibrating the LUT generated by method 900 may be advantageous. FIG. 24 is a flow diagram showing a method 1000 of calibrating a LUT. At Step 1002, battery pack voltage BV is obtained. In an embodiment, battery pack voltage magnitude BV is an analog voltage obtained by using the circuit disclosed in FIG. 19. In that circuit, the battery pack voltage magnitude BV may be input to a microcontroller unit 701 that converts analog voltage to digital voltage using an analog-to-digital converter, such as that implemented in the STM32F030K6 microcontroller unit. The STM32F030K6 microcontroller unit coverts analog voltage magnitude to a digital code corresponding to the 12-bit ADC (i.e., 0 to 4096). The digital code represents a voltage magnitude corresponding to the original battery pack voltage magnitude BV obtained.

Figure 25:
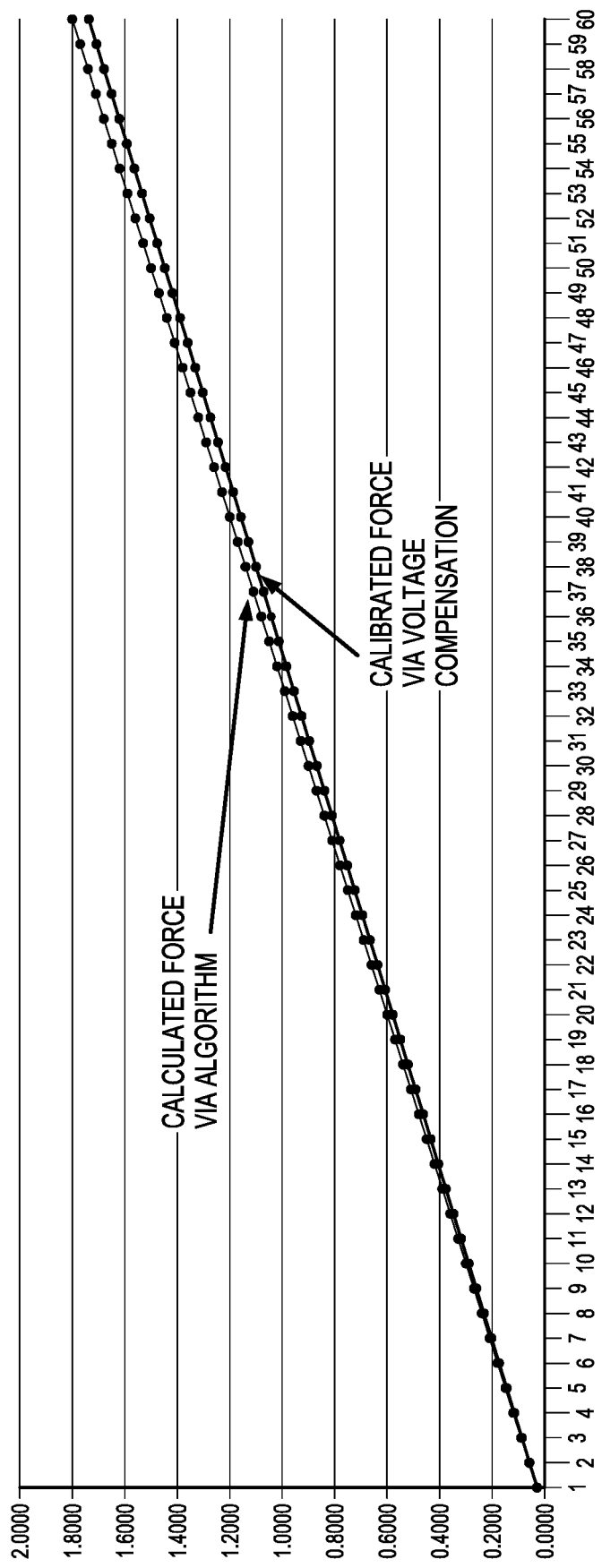
FIG. 25 is a graph plotting a lookup table generated by a method of detecting force applied by the percussive massage device against a lookup table calibrated by using a method of calibrating a lookup table according to a preferred embodiment.

At Step 1004, $V_{MAX}$ is set to the actual battery voltage magnitude BV output. As an example, may decrease from 1.8 volts to 1.74 volts, a 0.6 volt decrease. At Step 1006, the LUT linear correlation is adjusted to reflect the lower $V_{MAX}$. FIG. 25 is a graph plotting the LUT calculated by the method 900 against the LUT calibrated by using the method 1000. The LUT resulting from method 1000 depicts a calibrated force rather than a calculated force.

Figure 26:
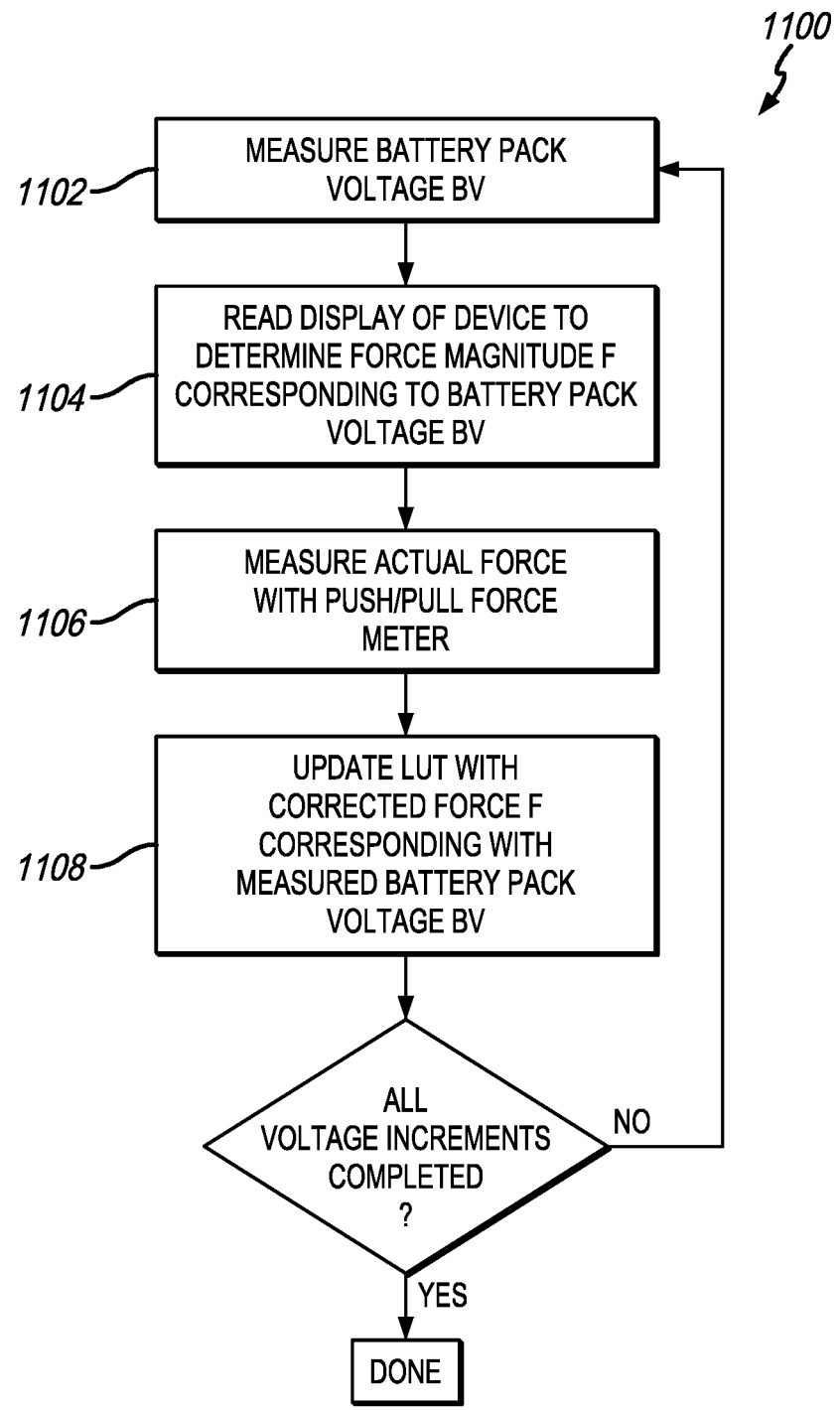
FIG. 26 is a flow diagram showing a method of calibrating a lookup table.

FIG. 26 is a flow diagram showing a method 1100 of calibrating a LUT. The method 1100 may be performed after the method 900, or entirely separately from the method 900. At Step 1102, battery pack voltage BV is measured. In an embodiment, the measurement is done without applying any force from the percussive massage device with force meter 400. In an embodiment, the battery pack voltage BV is measured using an external voltage meter. In another embodiment, the battery pack and/or microcontroller unit 701 have embedded solutions for directly measuring battery pack voltage BV.

At Step 1104, the display on the percussive massage device with force meter 400 that displays the force magnitude F is read to determine the force magnitude F corresponding to the measured battery pack voltage BV.

Figure 27:
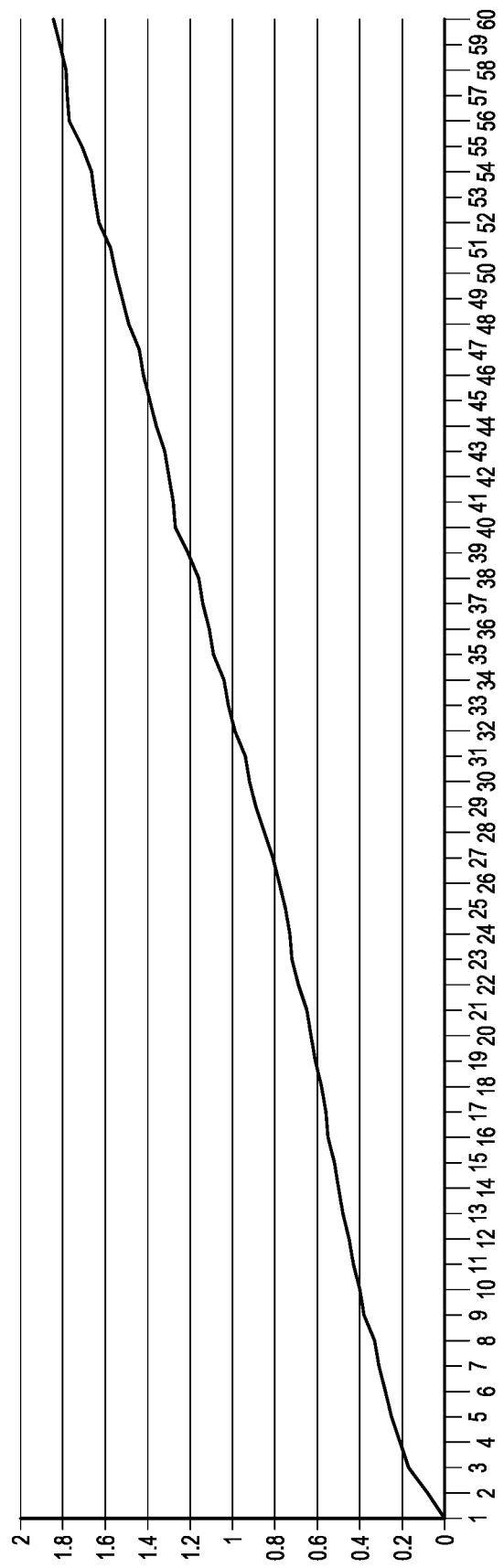
FIG. 27 is a graph plotting a lookup table after being calibrated in accordance with a preferred embodiment.

At Step 1106, a force meter is used to measure actual force being applied. In an embodiment, the force meter is a push/pull force meter. The direct measurement of force allows calibration of the LUT by comparing the displayed force magnitude F with the measured actual force. At Step 1108, the LUT is updated with a corrected force corresponding with the measured battery pack voltage BV. After Step 1108, Steps 1102-1106 are repeated for each successive voltage increment. In the embodiment depicted in accordance with the method 900, Steps 1102-1106 are repeated for every 0.03-volt increment. FIG. 27 is a graph plotting the LUT calculated by the method 1100 after all 3-volt increments had been updated.

Figures 28, 29:
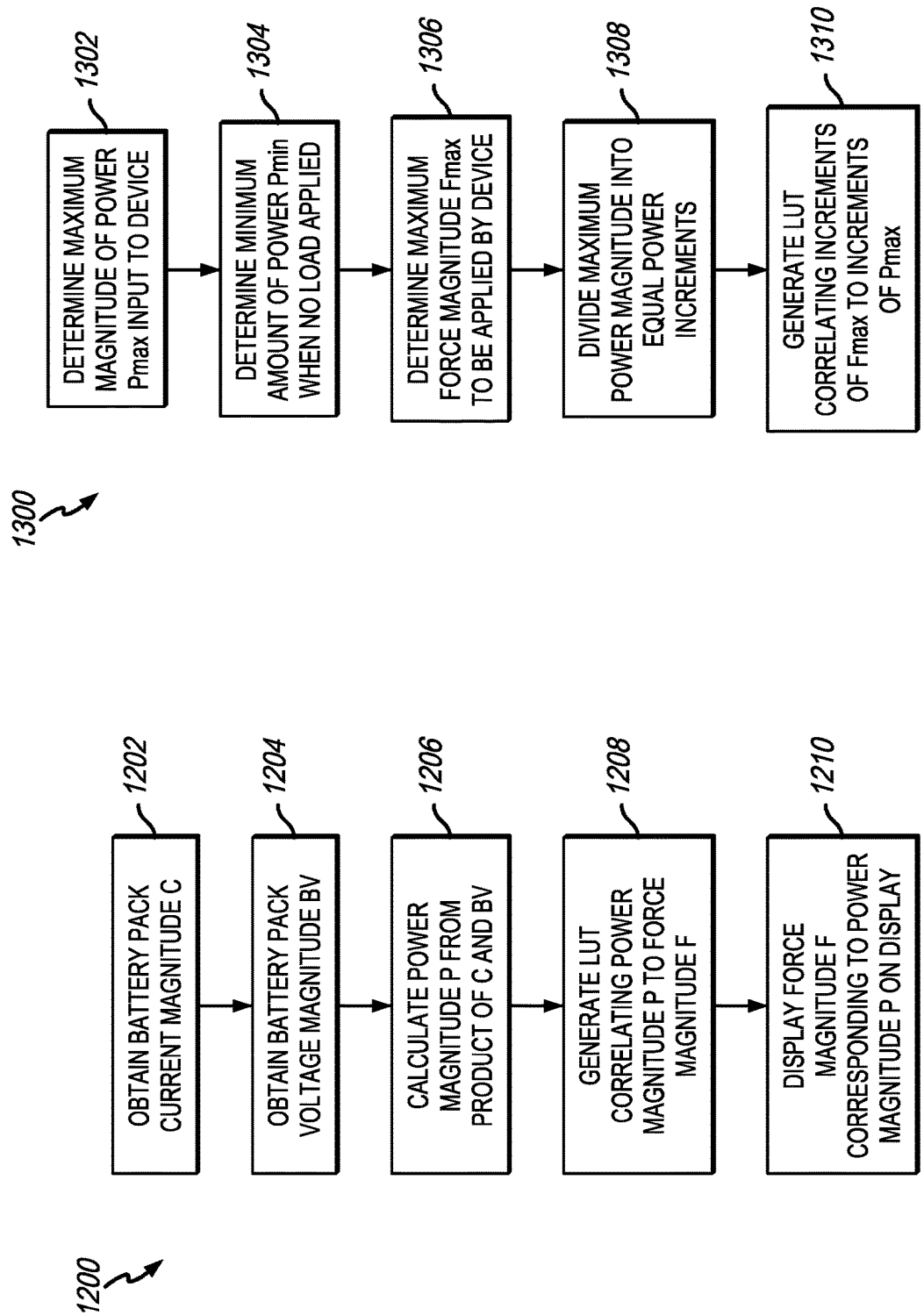
FIG. 28 is a flow diagram showing a method of detecting force applied by a percussive massage device in accordance with a preferred embodiment.
FIG. 29 is a flow diagram showing a method of generating a lookup table correlating power to force in accordance with a preferred embodiment.

FIG. 28 is a flow diagram showing a method 1200 of detecting force applied by a percussive massage device in accordance with a preferred embodiment. At Step 1202, current magnitude C of a battery pack is obtained. In an embodiment, current magnitude C is input into the microcontroller unit 701. At Step 1204, voltage magnitude BV of a battery pack is obtained. In an embodiment, voltage magnitude BV is input into the microcontroller unit 701. At Step 1206, power is calculated using the product of C and BV. In an embodiment, the microcontroller unit 701 is configured to calculate power by multiplying C and BV. At Step 1208, a lookup table is generated that correlates power magnitude P to force magnitude F. In an embodiment, the lookup table is generated using a method 1300 of generating a lookup table correlating power to force. For example, the power magnitude P may be expressed in watts. In an alternative embodiment, force magnitude F may be expressed in pounds of force or Newtons of force.

At Step 1210, the force magnitude F corresponding to power magnitude P is displayed on the percussive massage device with force meter 400. In an embodiment, a series of LED lights may be utilized to depict varying amounts of force as the force is being applied by the percussive massage device with force meter 400. Thus, as the amount of force magnitude F increases, more LEDs on the series of LED lights will be lit. Preferably, the series of LED lights consists of 12 LED lights.

FIG. 29 is a flow diagram showing a method 1300 of generating a lookup table correlating power to force. At Step 1302, a maximum magnitude of power, Fax, is determined. A theoretical maximum magnitude of power, however, is not a reasonable assumption if the total effective power may be calculated. Equation 1 may be utilized to determine Total Maximum Effective Power ($EP_{MAX}$).

$$\text{Total } EP_{MAX} = P_{MAX} \times \text{Total } EP \qquad \text{Equation 1:}$$

Equation 2 may be utilized to calculate Total EP, which is then input into Equation 1 above.

$$\text{Total } EP = EP_{BATTERY} \times EP_{PCBA} \times EP_{MOTOR} \qquad \text{Equation 2:}$$

where Total EP, $EP_{BATTERY}$, $EP_{PCBA}$, and $EP_{MOTOR}$ are all expressed in percentages, and where PCBA is a printed circuit board assembly.

In an embodiment, EP (Battery) is 85%, EP (PCBA) is 95%, and EP (Motor) is 75%. Thus, using Equation 2, Total EP is 85%*95%*75%=60.5625%.

In this embodiment, $P_{MAX}$ is calculated by multiplying the maximum voltage $V_{MAX}$ and the maximum amperage $C_{MAX}$ of the battery pack such as in Equation 3. $P_{MAX}$ is then input into Equation 1.

$$P_{MAX} = V_{MAX} \times C_{MAX}$$

In this embodiment, $V_{MAX}$ is 16.8 volts and $C_{MAX}$ is 20 amperes. Thus, $P_{MAX}$ is 336 watts.

Turning back now to Equation 1, if $P_{MAX}$ is 336 watts and Total EP is 60.5625%, then Total $EP_{MAX}$ is 203 watts.

At Step 1304, a minimum amount of power $P_{MIN}$ is determined. It will be recognized by one of ordinary skill in the art that the power without any force being applied (i.e., no load) will be non-zero. Thus, $P_{MIN}$ of 12 watts is assumed. One of ordinary skill will also understand that the value of is equivalent to the rated power without load, which may be derived from $V_{MAX}$ and $C_{MIN}$.

At Step 1306, a maximum magnitude of force, $F_{MAX}$, is determined. The magnitude of $F_{MAX}$ may be determined by assessing the maximum desired force to apply using the percussive massage device with force meter 400. As an example, $F_{MAX}$ is 60 pounds of force.

At Step 1308, Total $EP_{MAX}$ is divided into equal increments. In an embodiment, Total $EP_{MAX}$ is divided in 3 watt increments per one pound of force, starting at $P_{MIN}$ (12 watts). It will be recognized by one of ordinary skill in the art that if $F_{MAX}$ is 60 pounds of force, the total desired force output of the percussive massage device with force meter 400, then 60 pounds of force correlates to 189 watts, within the calculated Total $EP_{MAX}$.

Figure 30:
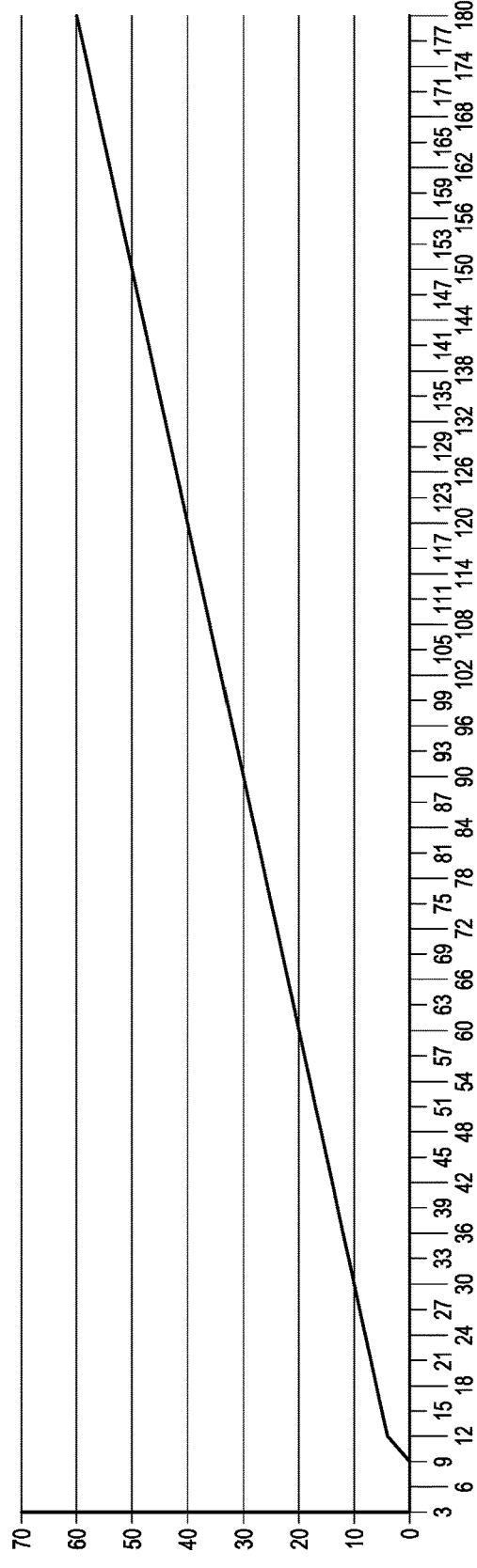
FIG. 30 is a graph plotting a lookup table for use by a method of detecting force of that was generated by correlating power to force in accordance with a preferred embodiment.

At Step 1310, a LUT is generated that correlates the increments of pounds of force with the increments of power in watts. This necessarily creates a linear relationship between force and voltage. FIG. 30 is a graph plotting the LUT for use by the method of detecting force of FIG. 28 that was generated using the specific example identified in FIG. 25. The graph depicts calculated force that was calculated using the method 1200.

Similarly to the method 900, a problem may arise in that the measured voltage of the battery pack at Step 1204 in the method 1200 is inaccurate. It may also be the case that as the percussive massage device with force meter 400 is used, the maximum available voltage degrades over time. In other words, the battery or battery pack voltage may decrease.

Figure 31:
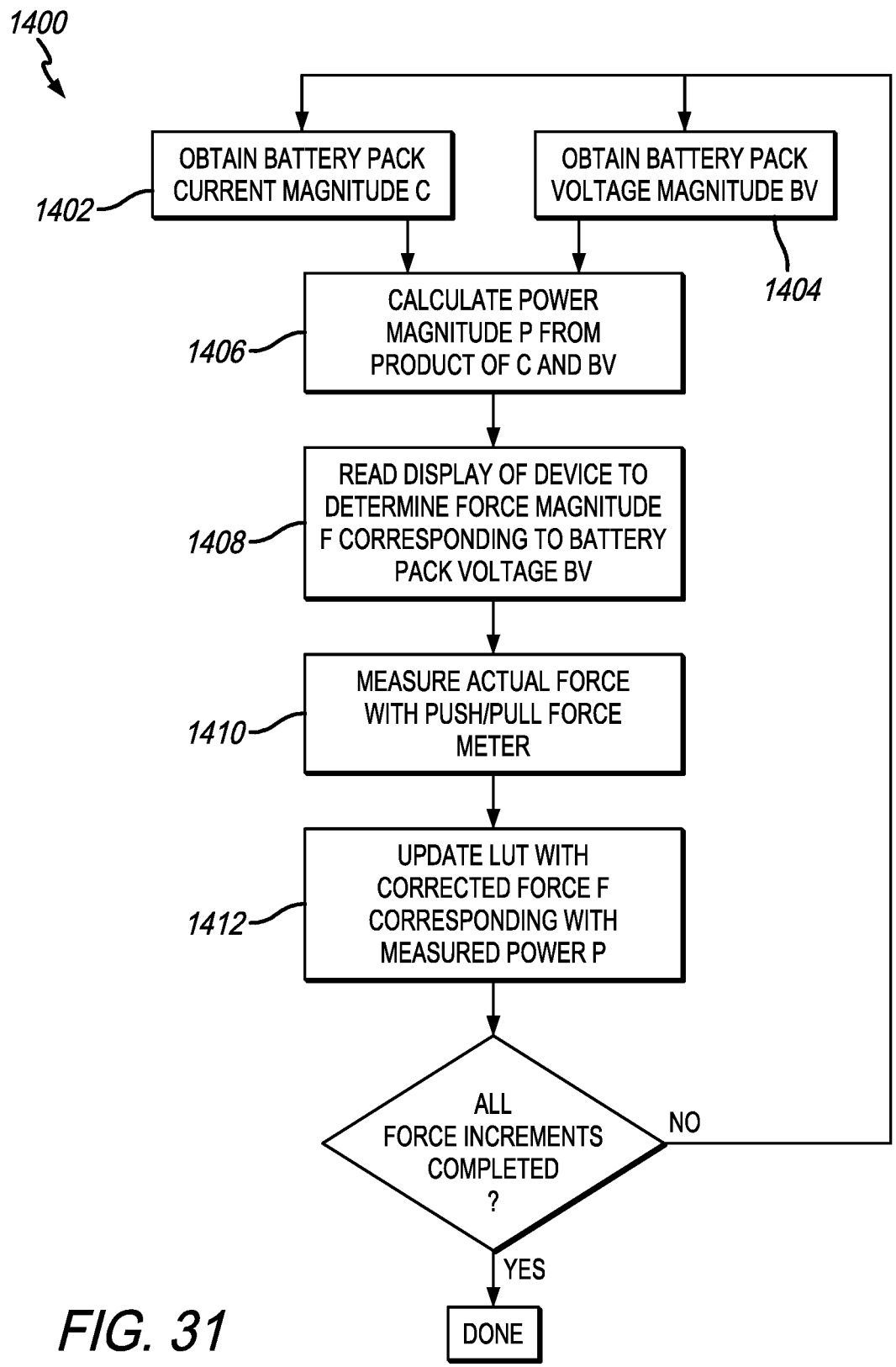
FIG. 31 is a flow diagram showing a method of calibrating a lookup table in accordance with a preferred embodiment.

FIG. 31 is a flow diagram showing a method 1400 of calibrating a LUT. The method 1400 may be performed after the method 900 or the method 1200, or entirely separately from the method 900 or the method 1200. At Step 1402, current magnitude C of a battery pack is obtained. In an embodiment, current magnitude C is input into the microcontroller unit 701.

At Step 1404, battery pack voltage BV is measured. In an embodiment, the measurement is done without applying any force from the percussive massage device with force meter 400. In an embodiment, the battery pack voltage BV is measured using an external voltage meter. In another embodiment, the battery pack and/or microcontroller unit 701 have embedded solutions for directly measuring battery pack voltage BV. At Step 1406, power is calculated using the product of C and BV. In an embodiment, the microcontroller unit 701 is configured to calculate power by multiplying C and BV.

Figure 32:
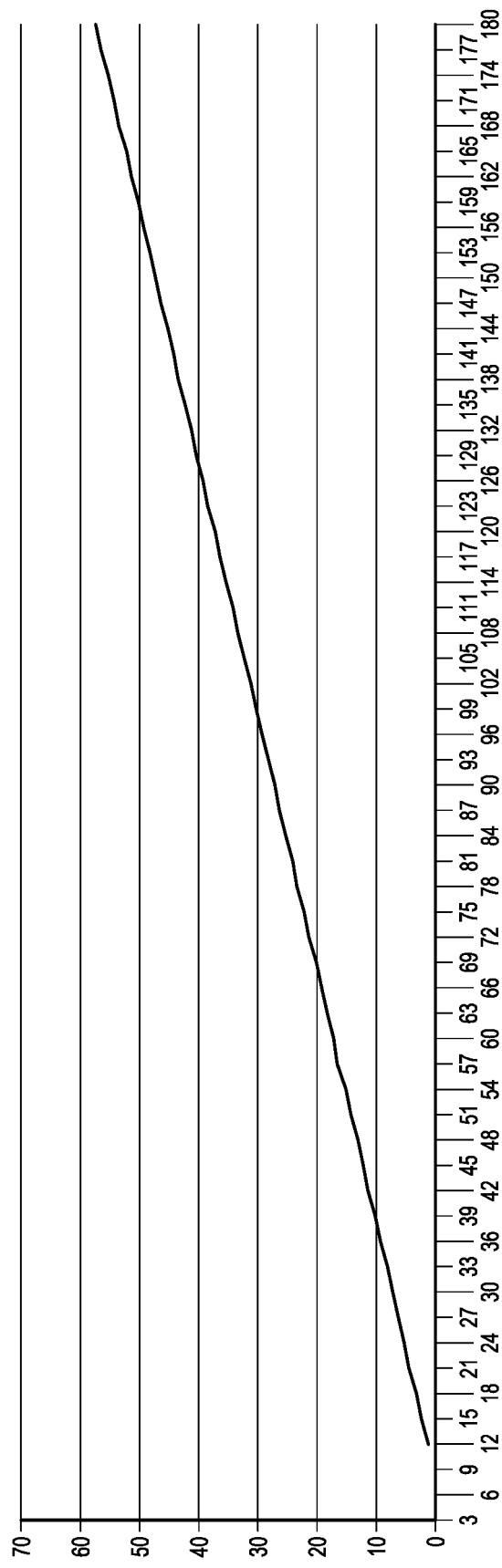
FIG. 32 is a graph plotting a lookup table after being calibrated in accordance with a preferred embodiment.

At Step 1408, the display on the percussive massage device with force meter 400 that displays the force magnitude F is read to determine the force magnitude F corresponding to the calculated power. At Step 1410, a force meter is used to measure actual force being applied. In an embodiment, the force meter is a push/pull force meter. The direct measurement of force allows calibration of the LUT by comparing the displayed force magnitude F with the measured actual force. At Step 1412, the LUT is updated with a corrected force corresponding with the measured power. After Step 1412, Steps 1402-1410 are repeated for each power or force increment. In the embodiment depicted in accordance with the method 900, Steps 1402-1410 are repeated for every 3-watt increment. FIG. 32 is a graph plotting the LUT calculated by the method 1400 after all 3-watt increments had been updated.

Figure 33:
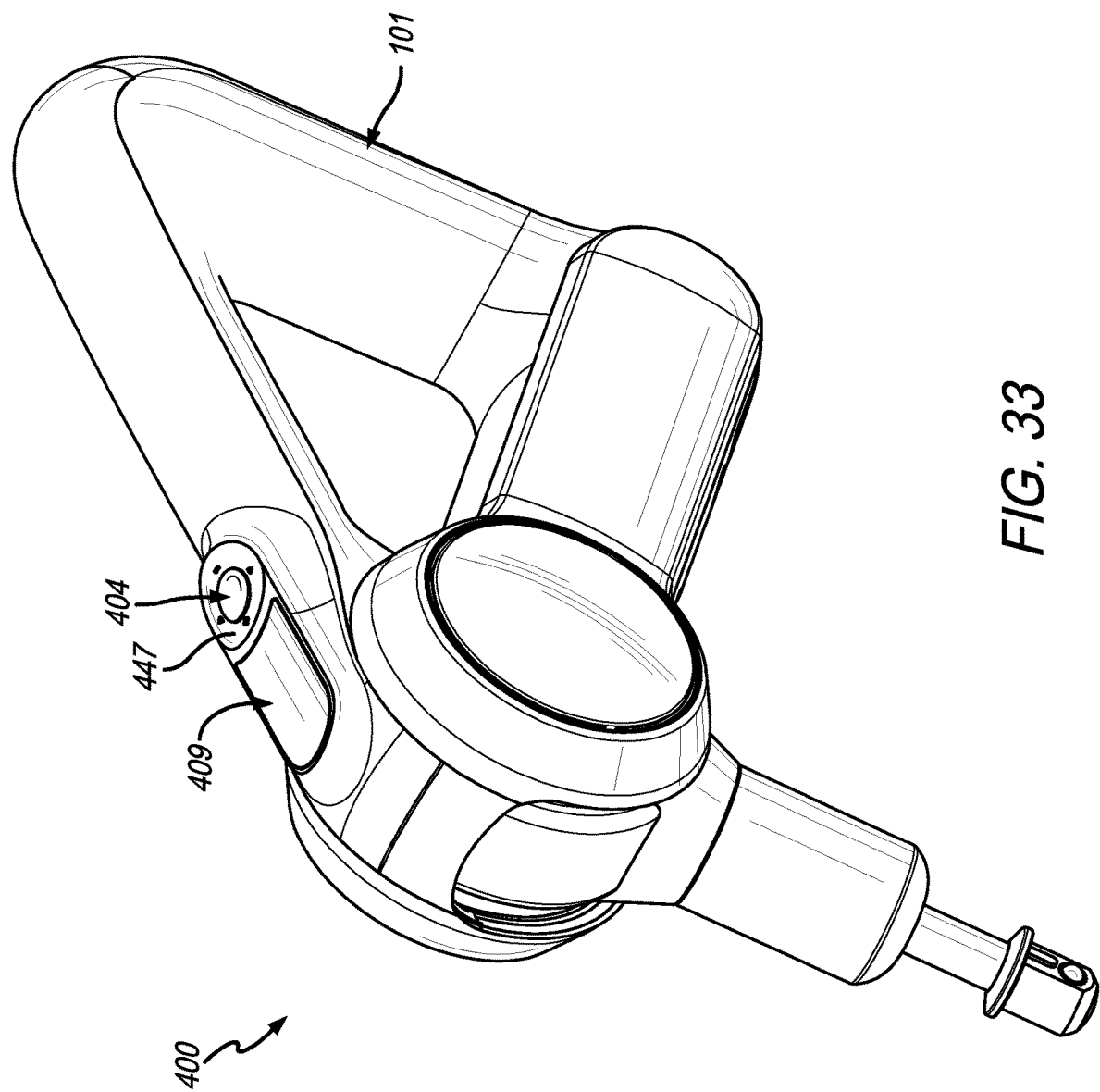
FIG. 33 is a perspective view of a percussive massage device in accordance with a preferred embodiment of the present invention.
Figure 34:
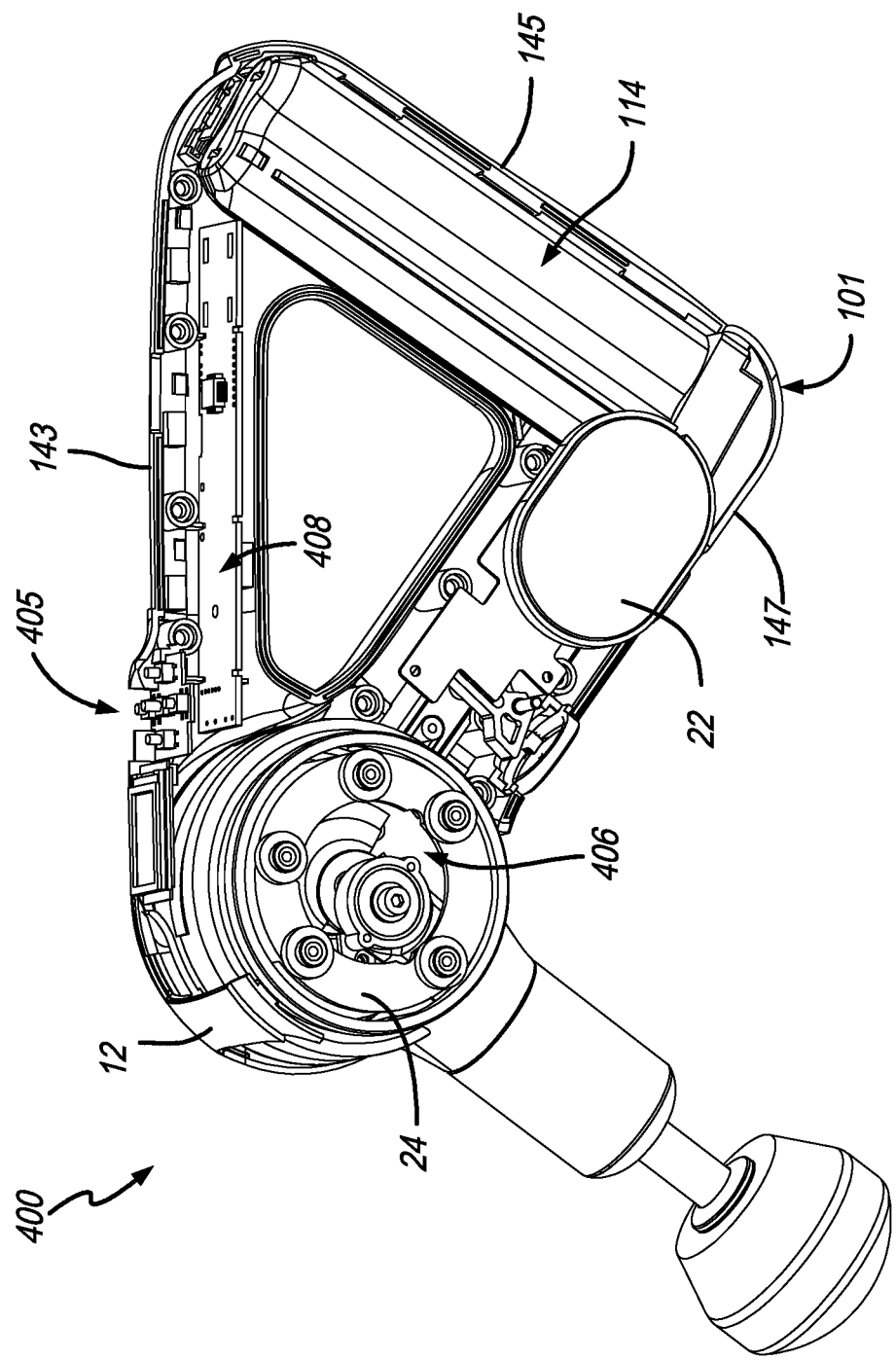
FIG. 34 is a perspective view of the percussive massage device of FIG. 13 with a portion of the housing removed.
Figure 35:
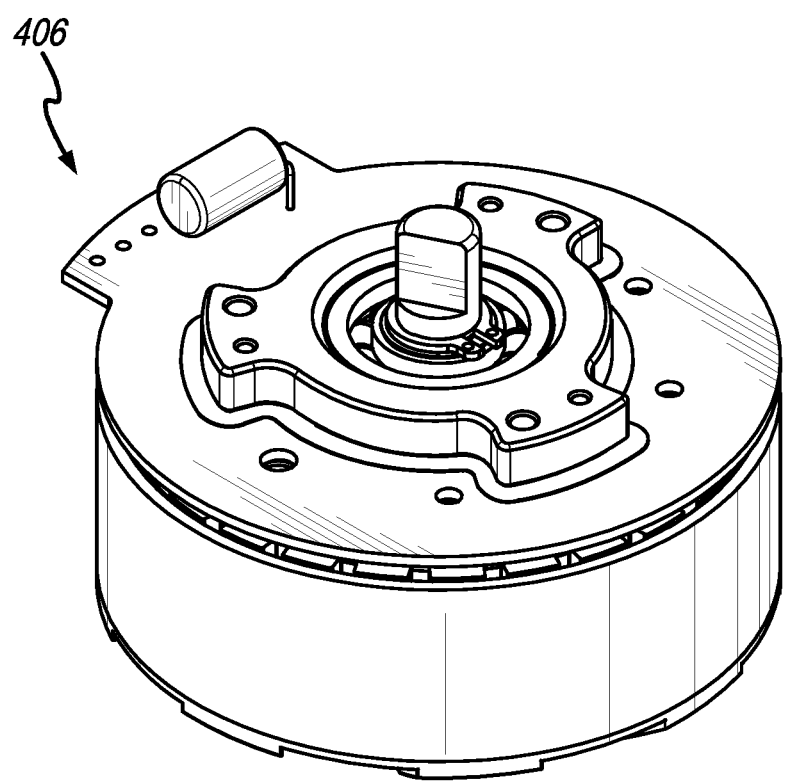
FIG. 35 is a perspective view of the motor.

FIGS. 33-35 show an exemplary percussive massage device 400 that embodies the features disclosed herein, and, in particular, in FIGS. 17-48 (or FIGS. 1-16). Generally, the percussive massage device 400 includes a housing 101, an electrical source or battery pack 114, a motor 406 positioned in the housing 101, and a switch 405 for activating the motor 406. The electronics (see printed circuit board 408 in FIG. 34) includes the controller that is configured to obtain a voltage of the motor, generate a lookup table correlating voltage to force applied by the percussive massage device, and display a force magnitude corresponding to the obtained voltage using the lookup table.

Figure 36:
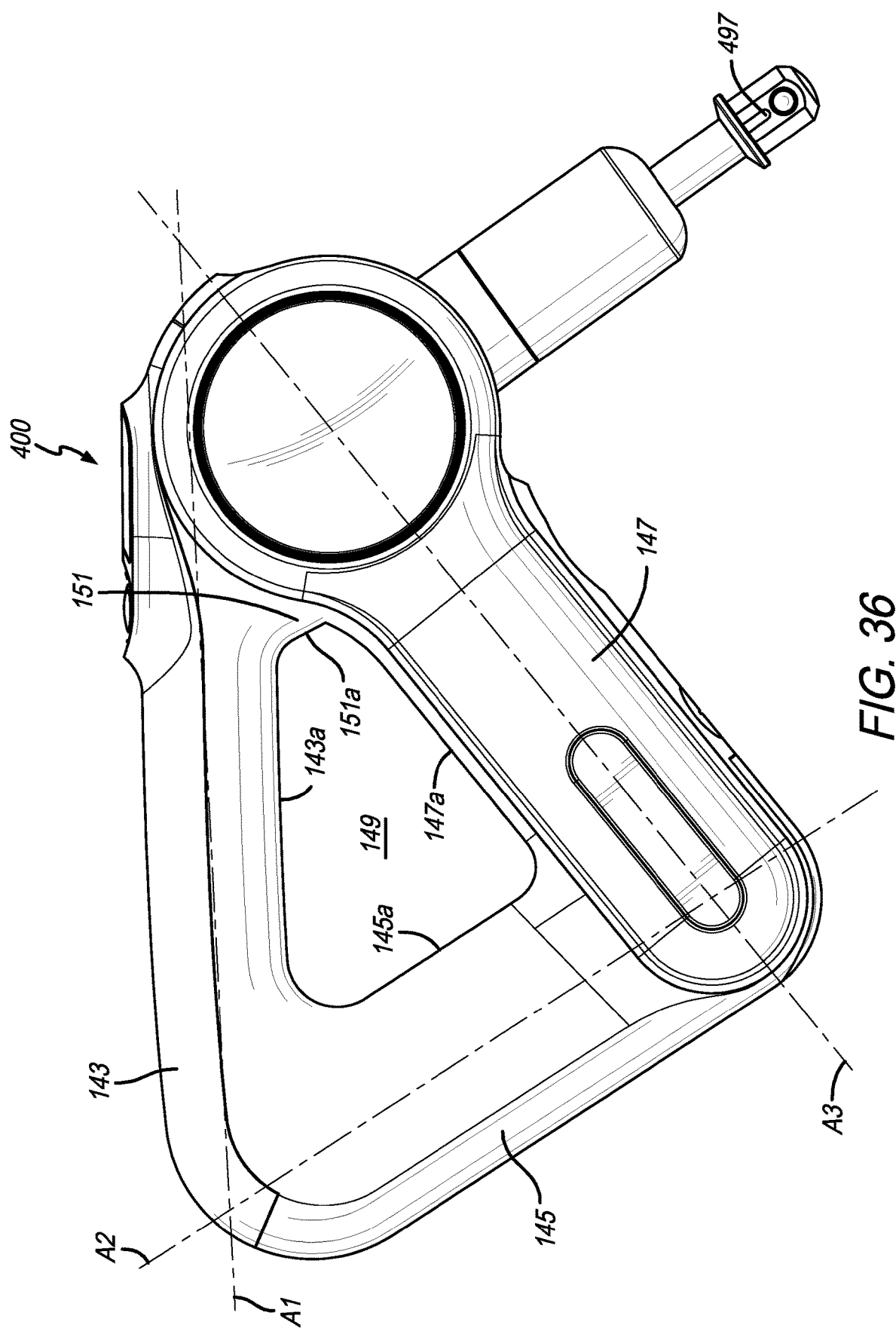
FIG. 36 is a side elevational view of the percussive massage device in accordance with a preferred embodiment of the present invention.
Figure 37:
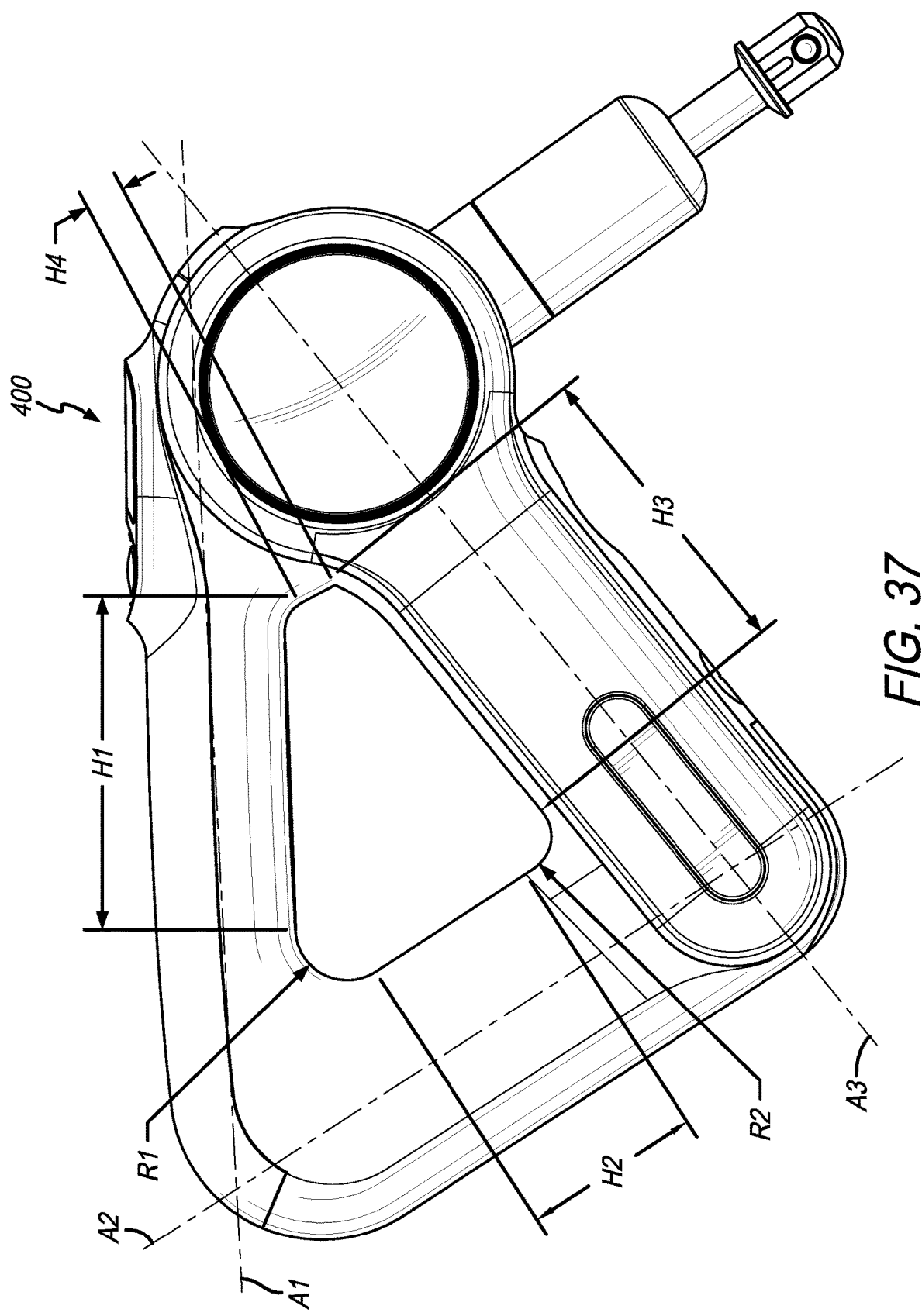
FIG. 37 is another side elevational view of the percussive massage device.

FIGS. 36-43A show further views of percussive massage device 400. FIGS. 36 and 37 are similar to FIGS. 1 and 1A and show that percussive massage device 400 includes a similar triangle shape with first, second and third handle portions 143, 145 and 147 that cooperate to define the handle portion 149. Refer to the description of at least FIGS. 1-5 for an explanation of the other reference numerals and features shown in FIGS. 36-40. All features and components described above with respect to any percussive therapy or massage devices may be included in percussive massage device 400.

Figure 41:
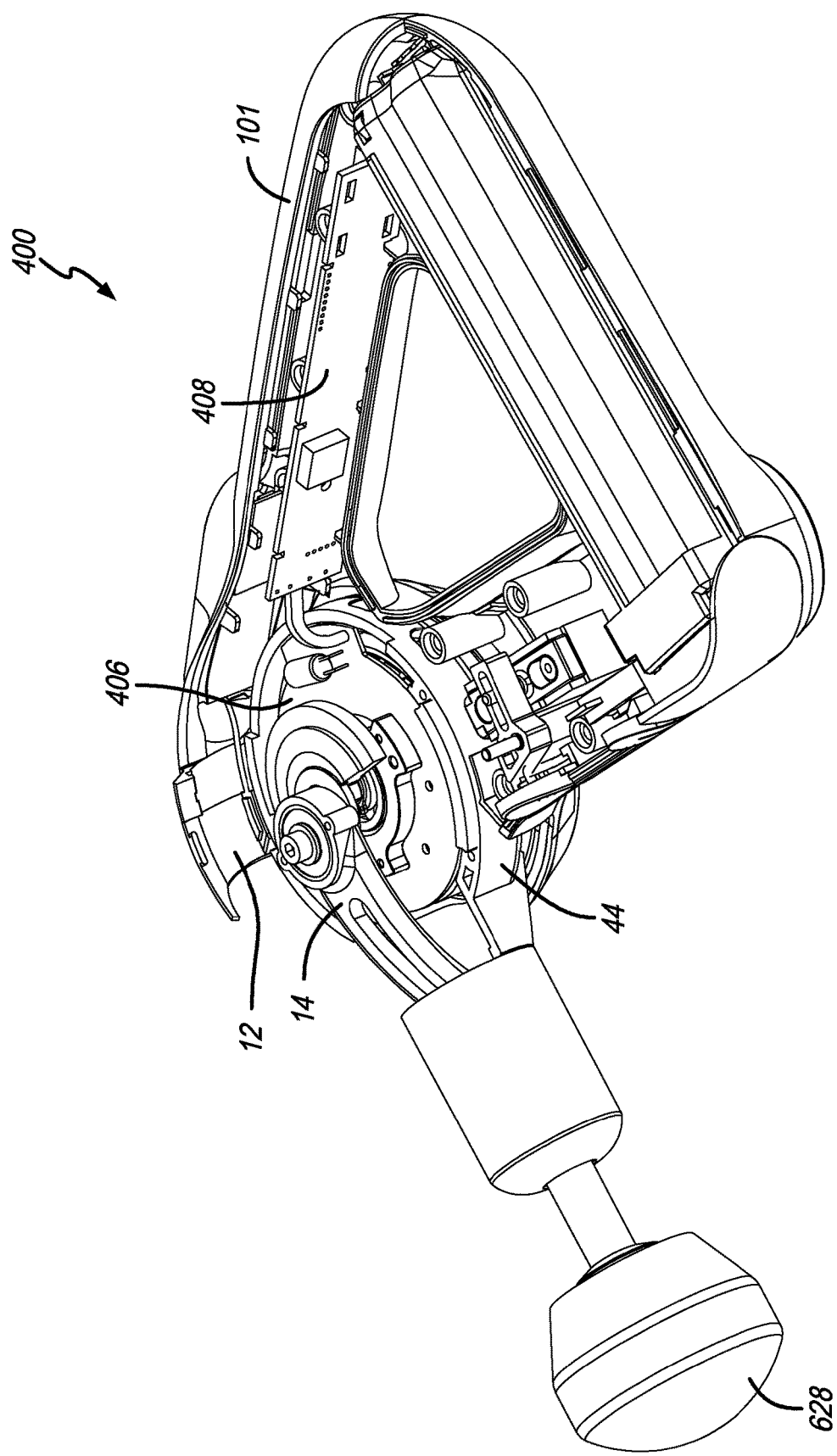
FIG. 41 is a perspective view of the percussive massage device of FIG. 18 with a portion of the housing removed.
Figure 42B:
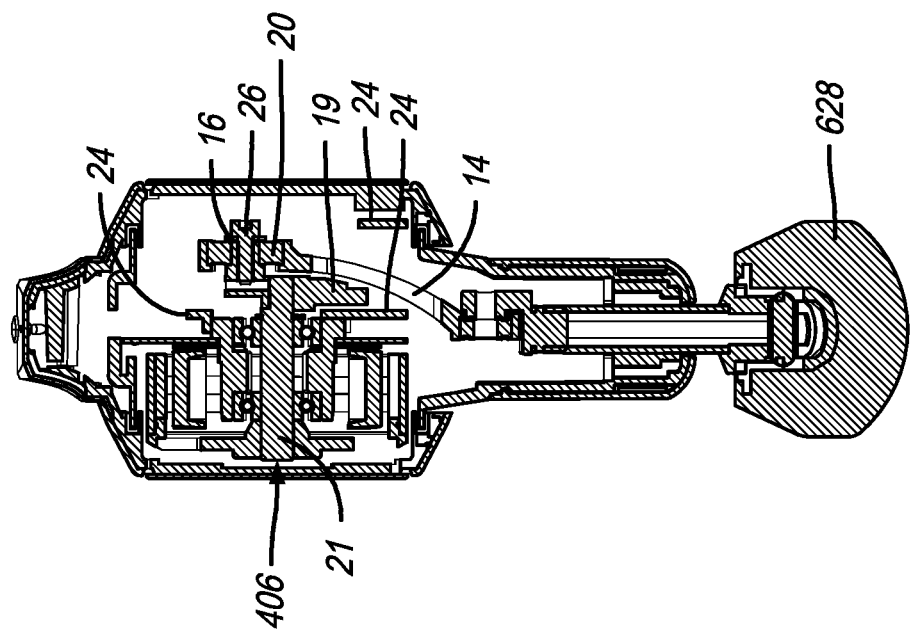
FIGS. 42A and 42B are cross sectional views of the head portion and motor.
Figure 42A:
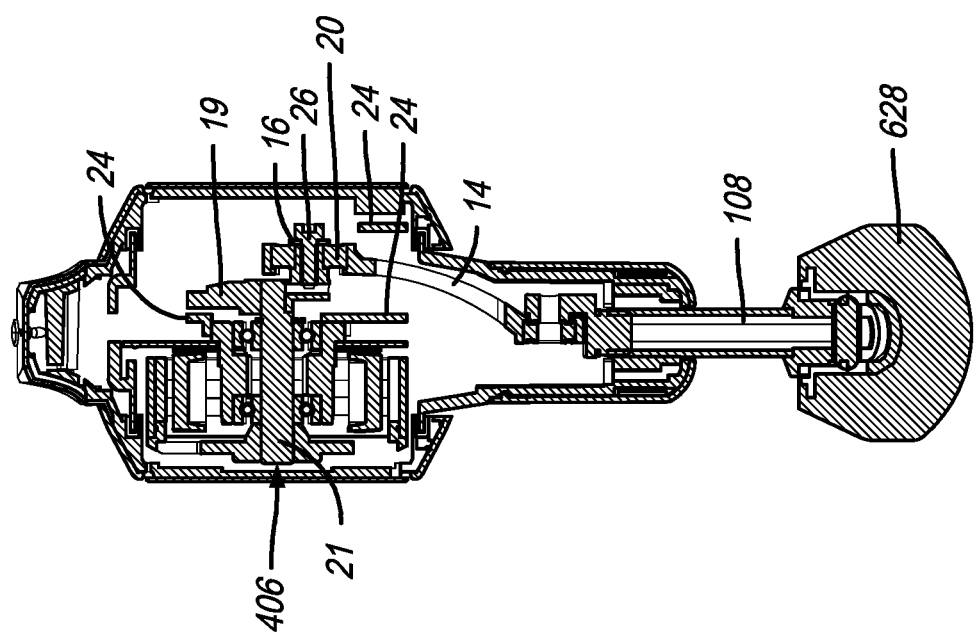
Figure 43:
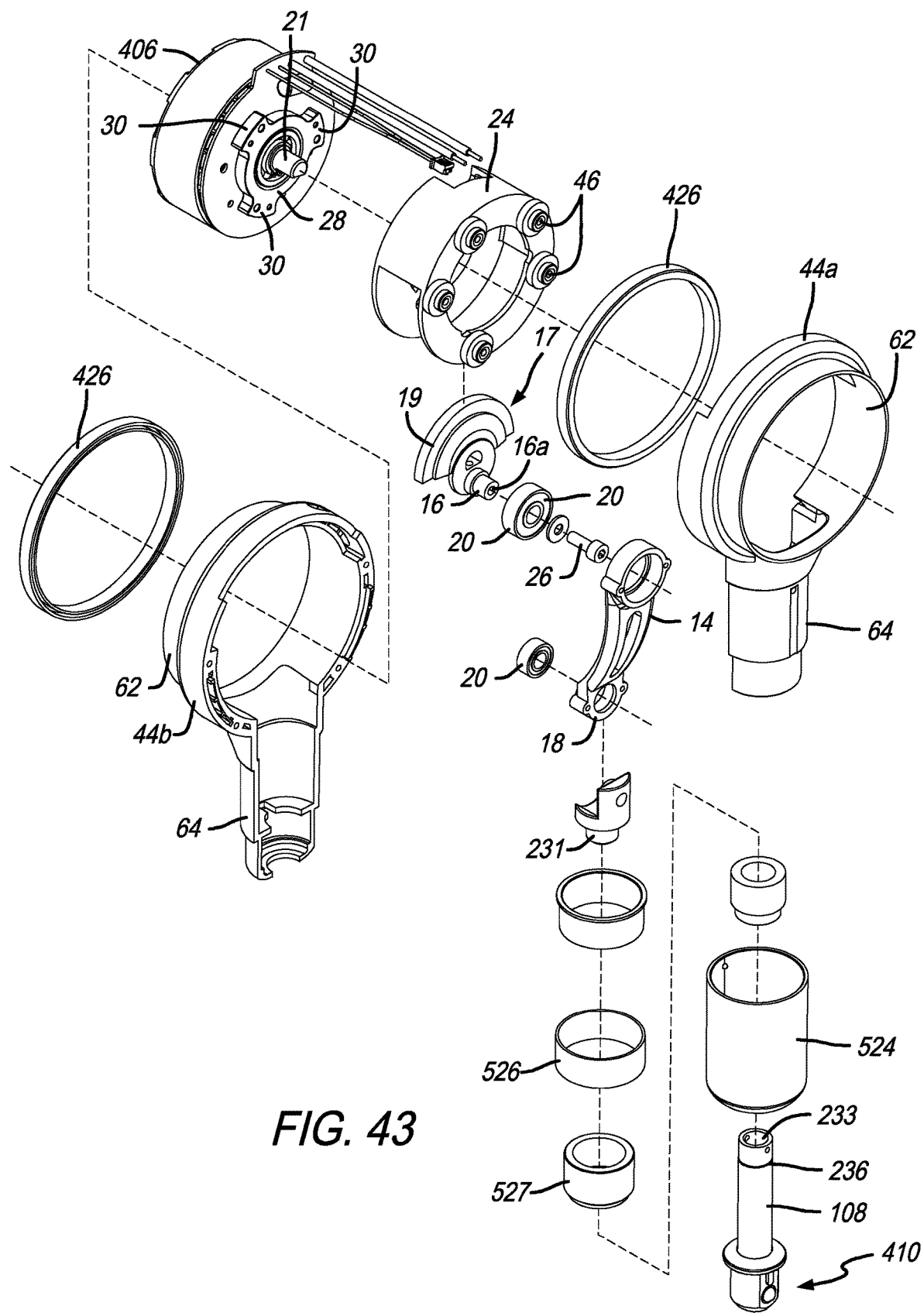
FIG. 43 is an exploded view of some of the internal components of percussive massage device of FIG. 33.

As shown in FIGS. 41-43, in a preferred embodiment, the brushless motor 406 is located in the head portion 12. The percussive massage device 400 can include a rotatable arm that is part of rotation housing 44. The motor 406 is located in the rotation housing 44, which is housed with the head portion 12 of the housing 101. In another embodiment, the rotation capability can be omitted.

In a preferred embodiment, the device includes a push rod or shaft 14 that is connected directly to a shaft 16 that is rotated by the motor 406 and the motor shaft 21 extending therefrom. The shaft 16 can be part of a counterweight assembly 17 that includes a counterweight 19. In a preferred embodiment, the push rod 14 is L-shaped or includes an arc shape, as shown in FIGS. 42A-42B. Preferably, the point where the push rod 14 is connected to the shaft 16 is offset from the reciprocating path that the distal end 18 of the push rod 14 (and the massage attachment 628) travel. This capability is provided by the arc or L-shape. It should be appreciated that the push rod 14 is designed such that it can transmit the force at least partially diagonally or in an arc along its shape instead of vertically so the motor can be located at or near the middle of the device, otherwise a large protrusion would be necessary to keep the shaft in the center with the motor offset therefrom (and positioned in the protrusion). The arc also allows the push rod 14 to have a close clearance with the motor, as shown in FIGS. 42A and 42B and allows the outer housing to be smaller than similar prior art devices, therefore making the device 400 lower profile. FIG. 42A shows the push rod 14 at the bottom dead center of its travel and FIG. 42B shows the push rod 14 at the top dead center of its travel. Preferably one or more bearings 20 are included at the proximal end of the push rod 14 where it connects to the motor to counteract the diagonal forces and preventing the push rod 14 from moving and touching the motor 406. The bearing 20 is received on shaft 16 and a threaded fastener 26 is received in a co-axial opening 16a in shaft 16. The proximal end of the push rod 14 is received on bearing 20. These components are all shown in FIG. 43.

As shown in FIG. 33, in a preferred embodiment, the device 400 includes a touch screen 409 (also referred to herein as touch screen 1582 in association with method steps) as well as button(s) for operating the device (e.g., stopping, starting, activating, changing speeds, amplitudes, etc.). The touch screen 409 can also include other functions. The device 400 can also include a thumbwheel or rolling button positioned near the touch screen/on off button to allow the user to scroll or navigate through the different functions. touch screen 409 for operating the device. In the embodiment, shown in FIG. 33, the device 400 includes touch screen 409, a center button 404 for turning the device on and off and a ring/rocker button 447 that provides the ability to scroll left and right (e.g., to the preset treatments discussed herein) and up and down (e.g., to control the speed or frequency). The screen can also be a non-touch screen or just used for display.

In another preferred embodiment, any of the devices taught herein can include the ability to vary the amplitude or stroke, thus providing a longer or shorter stroke depending on the application or needs of the user. For example, the stroke can change or be changed between about 8-16 mm. In another embodiment, the stroke can be varied up to 25 or more mm. The amplitude/stroke variability can also be part of the routines, presets or protocols discussed herein. For example, the device can include a mechanical switch that allows the eccentricity of the connector to be modified (e.g., between 4 mm and 8 mm). The mechanism can include a push button and a slider. The pin structure has a spring that lets it fall back into the locked position.

Similar to percussive massage devices 208, 210 and 212 above, in a preferred embodiment, device 400 includes a number of dampening components that are made of an elastomer or the like and damp vibrations to keep the device relatively quiet. For example, as shown in FIG. 43, device 400 includes dampening rings 426 (similar to inner suspension rings 219) that surround the rotation housing 44 (with first and second rotation housing halves 44a and 44b) and help dampen the sound of vibration between the rotation housing and outer housing 101.

Figure 43A:
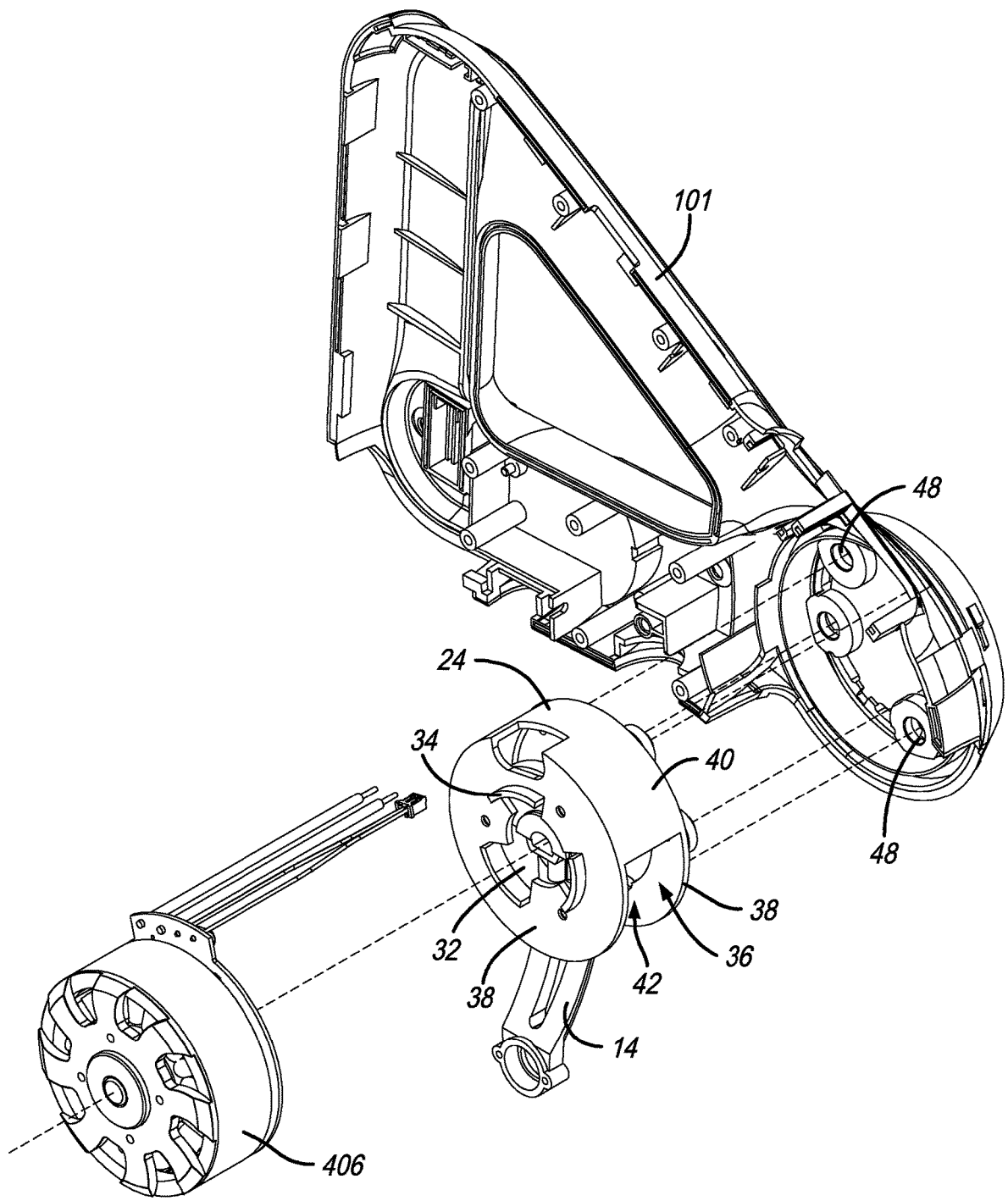
FIG. 43A is an exploded view of the motor and motor mount.

As shown in FIGS. 43 and 43A, the device 400 preferably also includes a motor mount 24 that secures the motor 406 in place and is secured to the housing 101. Motor 406 includes a receiving member 28 with three protrusions 30 (and number between one and ten can be included) that is received in a protrusion opening 32 defined in the motor mount 24 (in first wall 38). Flanges 34 extending from the motor mount 24 help keep the protrusions 30 in place. The motor 406 is preferably secured via threaded fasteners or the like to the motor mount 24. Motor shaft 21 extends into the motor mount interior 36, which is defined between first and second walls 38 and a side 40 that extends part of the way around the circumference. The counterweight assembly 17, proximal end of the push rod 14 and related components for converting the rotation of the motor shaft 21 to reciprocating motion are position in the motor mount interior 36. The push rod 14 extends downwardly out of the motor mount interior and through a push rod opening 42 in the side 40. In a preferred embodiment, the motor mount 24 is connected directly to the housing 101 via fasteners 46 that are secured to mounting members 48 in the housing (see FIG. 43A). It will be appreciated that the term push rod assembly used herein includes any of the components discussed herein or combinations thereof, e.g., push rod 14, output shaft 108, reciprocator 310, second rod portion 236, that extend from the rotating motor shaft 21, shaft 246 or the like that provide reciprocating motion and include the attachment on the distal end thereof. The push rod assembly also includes the male connector 110 (and any related components) or any other connector at the end of the reciprocating components that allows connection of an attachment to be used for massage or therapy.

Preferably the device can be wirelessly charged. FIG. 34 shows the wireless charging receiver 22, which is positioned in the third handle portion 147. In another embodiment, the wireless charging receiver 22 can be located either of the first and second handle portions 143 and 145 or in the head portion 12.

In a preferred embodiment, the device 400 is associated with and can be operated by an app or software that runs on a mobile device such as a phone, watch or tablet (or any computer). The app can connect to the device 400 via bluetooth or other wireless connection protocol. The app can have any or all of the following functions. Furthermore, any of the functions discussed herein can be added to the touch screen/scroll wheel or button(s) capability directly on the device. If the user walks or is located too far away from the device, the device will not work or activate. The device can be turned on an off using the app as well as the touch screen or button on the device. The app can control the variable speeds (e.g., anywhere between 1750-3000 RPM). A timer can be implemented so the device stops after a predetermined period of time.

In a preferred embodiment the device, via the app or the touch screen and other functional buttons, etc. includes different treatment protocols or routines associated therewith. During the routine, the device can vary different aspects or outputs of the device or make changes based on time, speed (frequency), amplitude (stroke), arm position, force, temperature, grip (i.e., which handle portion to grip), attachment (e.g., cone, ball, dampener, etc.) and body part. The device (via the app, touch screen, haptic feedback or audibly via a speaker) can also prompt the user to make some of these changes at certain points throughout the routine, e.g., arm position, grip, attachment changes and body part changes. One of ordinary skill in the art will understand that, depending upon the particular design of the device, one or more of these outputs are applicable, while in other devices, all options described are applicable.

Figure 38:
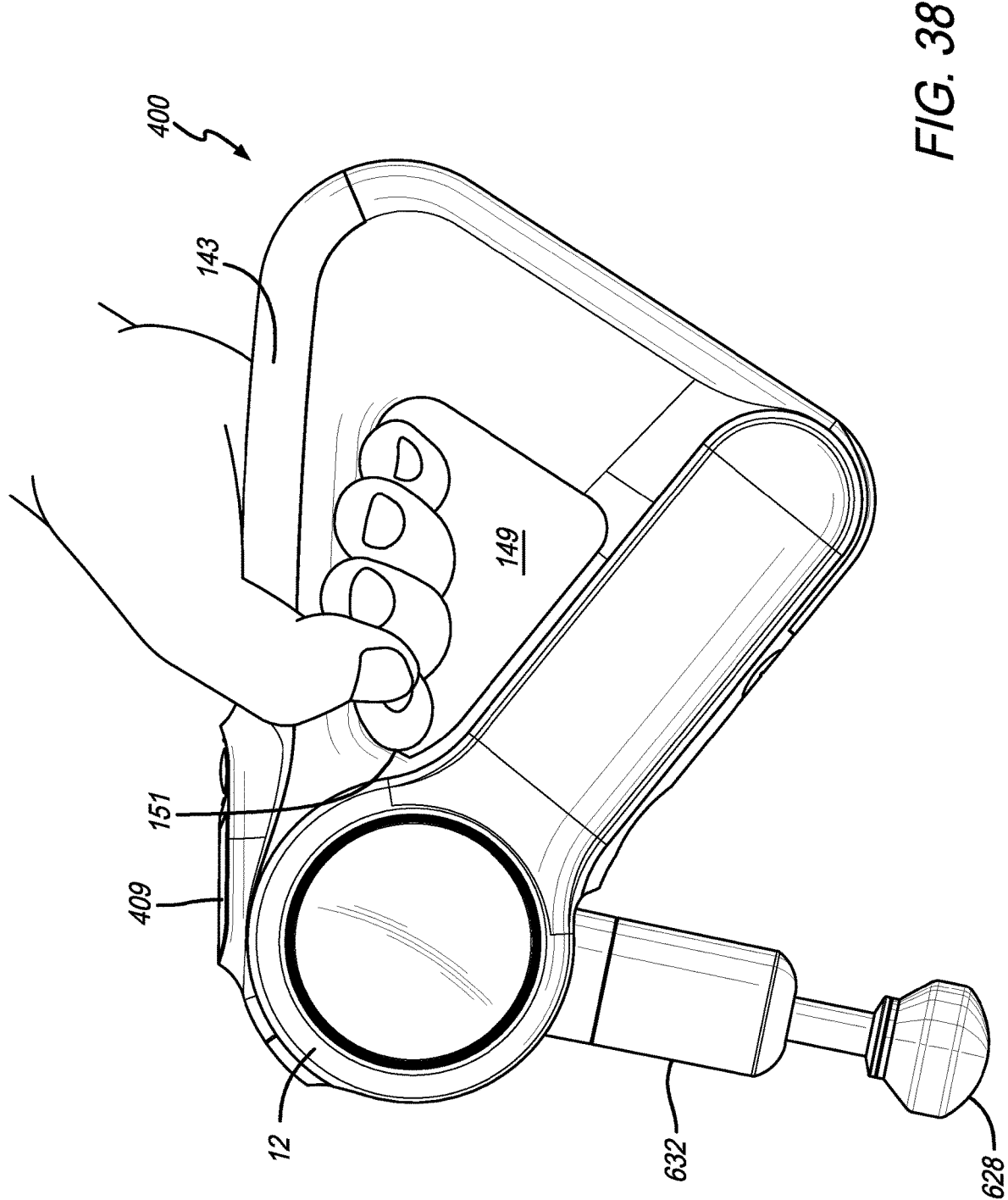
FIG. 38 is a side elevational view of the percussive massage device showing a user grasping the first handle portion.
Figure 39:
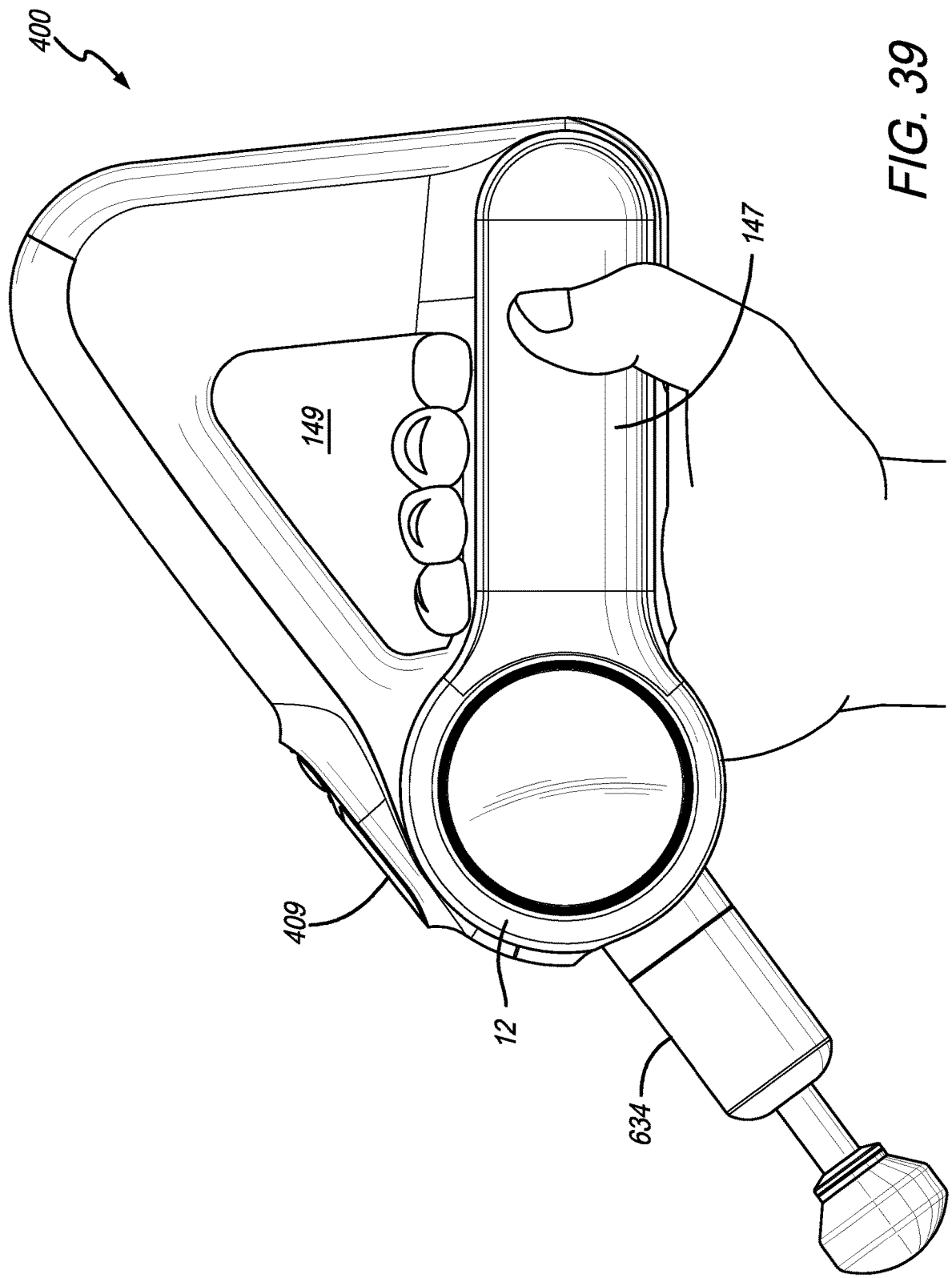
FIG. 39 is a side elevational view of the percussive massage device showing a user grasping the third handle portion.
Figure 40:
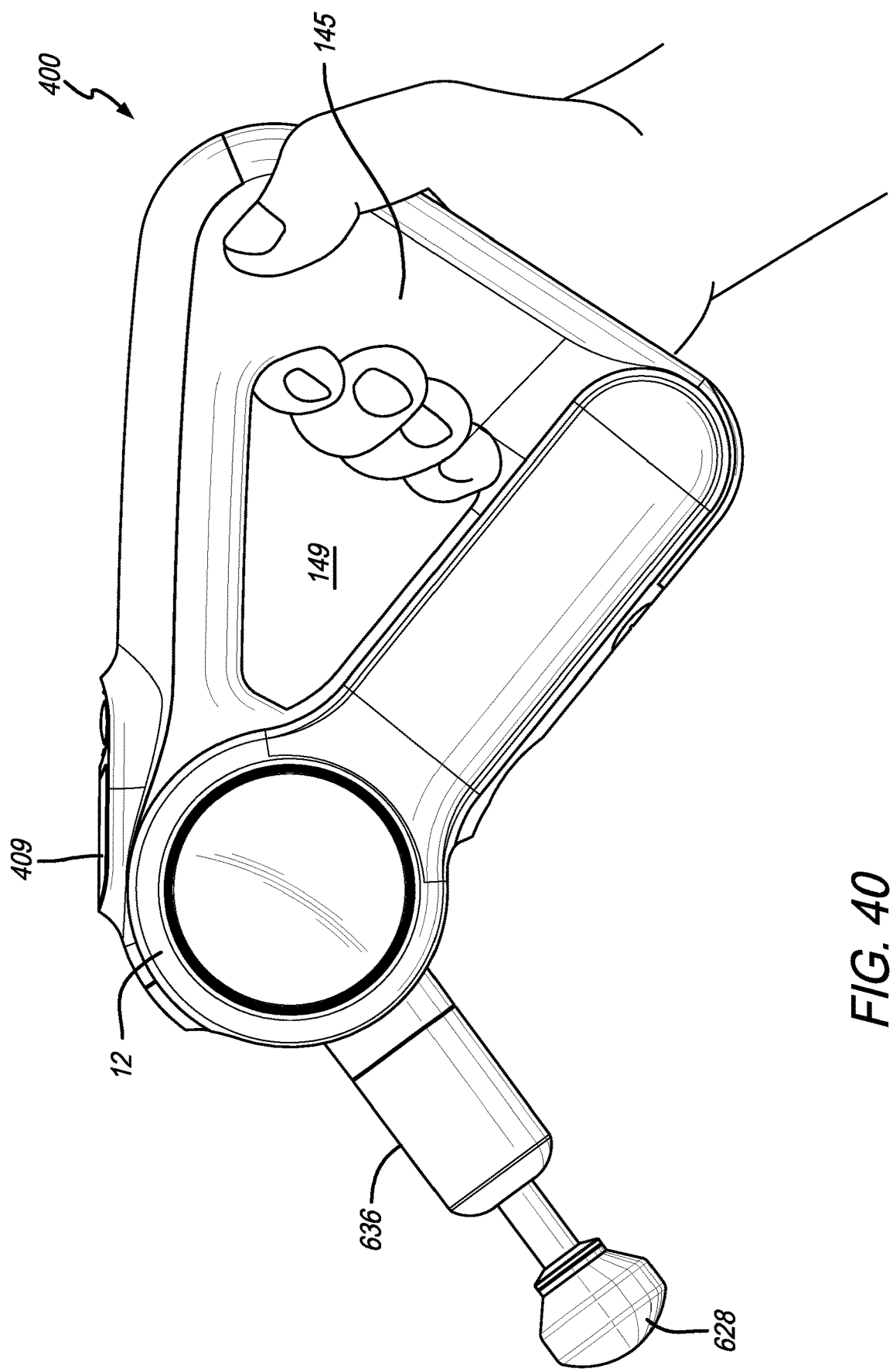
FIG. 40 is a side elevational view of the percussive massage device showing a user grasping the second handle portion.

When the start of the protocol is selected, the device runs through a preprogrammed routine. For example, the device may operate at a first RPM for a first period of time and then operate at a second RPM for a second period of time and/or at a first amplitude for a first period of time and then operate at a second amplitude for a second period of time. The routines can also include prompts (e.g., haptic feedback) for letting the user to know to move to a new body part. These routines or treatments can be related to recovery, blood flow increase, performance, etc. and can each include a preprogrammed routine or protocol. These routines can also help facilitate certain activities, such as sleep, interval training, stairs, post-run, post-workout, recovery, wellness, post-core exercise, high intensity (plyometric) workouts, among others. The routines can also assist in providing relief and recovery from ailments such as plantar fasciitis, "tech neck," muscle cramps, jet lag, sciatica, carpal tunnel, knots, and shin splints, among others. The routines can also prompt or instruct the user to switch attachments (e.g., attachment 628 shown in FIG. 40) or positions of the arm or rotation housing. The prompts can include sounds, haptic feedback (e.g., vibration of the device or mobile device), textual instructions or visual representation such as a graphic or picture on the app or touch screen, etc. For example, the app may instruct the user to start with the ball attachment with the arm in position two. Then the user hits start and the device runs at a first frequency for a predetermined amount of time. The app or device then prompts the user to begin the next step in the routine and instructs the user to change to the cone attachment and to place the arm in position 1 (e.g., see the arm position in FIG. 38). The arm can include any number of positions, e.g., 1-10 positions or 1-3 positions or 1-2 positions. FIGS. 38-40 show the arm in three different positions. The user hits start again and the device runs at a second frequency for a predetermined amount of time. The protocol can be divided into steps where, at each step, varied outputs are predetermined or specified.

In a preferred embodiment, the device 400 includes a housing 101, an electrical source 114, a motor 406 positioned in the housing 101, a switch 405 (which can be any of the touch screen 409, rocker button 447, button 404 or any other switch or button) for activating the motor 406, and a routine controller 630. The device 400 is configured to mate with an attachment 628. The attachment can be, for example, the attachment 628 shown in FIG. 38. The attachment is affixed to the male connector 110 so that the shaft or push rod assembly 108 moves the attachment reciprocally in accordance with a specified amplitude. For example, the amplitude is depicted in FIGS. 42A and 42B, where FIG. 42A shows the attachment at a maximum extended position and FIG. 42B shows the attachment at a minimum extended position. The distance between maximum and minimum extended positions can, in an embodiment, define the amplitude.

The attachment 628 can be a variety of attachments configured to provide therapeutic relief to specified portions of the body. For example, the attachment 628 can be a standard ball (see U.S. patent application Ser. No. 29/677,157, the entirety of which is incorporated herein by reference) attachment targeted for overall use on both large and small muscle groups. The attachment 628 can be a cone attachment (see U.S. Pat. No. D849,261, the entirety of which is incorporated herein by reference) for pinpoint muscle treatment, trigger points, and small muscle areas like the hands and feet. The attachment 628 can also be a dampener attachment (see U.S. patent application Ser. No. 29/676,670, the entirety of which is incorporated herein by reference) used for tender or bony areas, but also for overall uses. The attachment 628 can be a wedge attachment (see U.S. Pat. No. D845,500, the entirety of which is incorporated herein by reference) for use on shoulder blades ant IT bands, used for "scraping" and "flushing" motions that help to flush lactic acid out of muscles. The attachment 628 can be a large ball (see U.S. patent application Ser. No. 29/677,016, the entirety of which is incorporated herein by reference) for large muscle groups like glutes and quads. The attachment 628 can be a thumb attachment (see U.S. Pat. No. D850,639, the entirety of which is incorporated herein by reference) used on trigger points and the lower back. The attachment 628 can be a Supersoft™ attachment (see U.S. patent application Ser. No. 29/726,305, the entirety of which is incorporated herein by reference), designed to provide therapeutic relief to sensitive areas, including bones. One of ordinary skill in the art would recognize that the attachments described herein are non-limiting and other configurations of attachments, including varying materials and shapes, may be utilized in accordance with this embodiment. Spherical, forked, flat or other shaped attachments are all within the scope of the invention.

The routine controller 630 is configured to perform a routine in connection with one or more specified protocols. The routine controller 630 can be, for example, the microcontroller unit 701 depicted in FIG. 17. The routine controller 630 can also be a standalone microcontroller separate from the microcontroller 701. The routine controller can step through different steps of a specified protocol designed to target specified muscle groups and to provide certain therapeutic effects, as described herein.

FIG. 44 is a table showing an example of a protocol in accordance with a preferred embodiment. Protocol 1 is divided into four steps, each depicting a specified time, speed, amplitude, attachment, force, temperature, and grip. At Step 1, the device 400 is activated for 30 seconds at a speed of 1550 RPM. A routine controller 630 may be utilized to turn on the percussive massage device and implement a speed of the attachment 628 of 1550 RPM. One of ordinary skill in the art would understand that the speed of the attachment 628 is directly proportional to the speed of the motor 406. The amplitude of the percussive massage device is set to be 2 in accordance with Protocol 1. This may translate to a specified distance that an attachment 628 moves while in use, as described above. Step 1 also specifies a dampener attachment affixed to the device 400, a force of "1" be applied by the device 400, and a temperature of 21° C. be applied to the attachment.

One of ordinary skill in the art would understand that the force to be applied by the device 400 may depend upon the pressure exerted by the user in pressing the attachment onto a person's body part. As described more fully herein, the force to be applied by the device 400 may be the target force. In an embodiment where the user provides pressure to exert a particular force upon a person's body part, the routine controller 630 may adjust the output of the device 400 to ensure that the force actually applied by the attachment is the target force. The routine controller 630 may also be configured to provide feedback to the user to increase or decrease pressure on a person's body part to meet the target force. Each of these embodiments is applicable to each of the steps of a given protocol, including in Steps 2-4 below, as well as Steps 1-4 of the protocol shown in FIG. 45.

Step 1 also specifies that the device 400 is to be operated using grip 1. Grip 1, for example, may be the grip shown on the first handle portion 143 depicted in FIG. 38, otherwise referred to as a "regular" or "standard" grip. Grip 2, for example, may be the grip shown on the third handle portion 147 depicted in FIG. 39, otherwise referred to as a "reverse" grip. An "inverse" grip can also be used on third handle portion 147 (not shown). Grip 3, for example, may be the grip shown on the second handle portion 145 depicted in FIG. 40, otherwise referred to as a "base" grip.

At Step 2, Protocol 1 specifies that the device 400 be activated for 15 seconds at 2100 RPM, with an amplitude of "3", a force of "3", and a temperature of 26° C. Step 2 specifies that the small ball attachment 628 be used, and that the device 400 is to be operated using grip 1. Step 2 therefore requires that the dampener attachment in Step 1 be replaced by the small ball attachment, but specifies that the same grip is to be used.

At Step 3, Protocol 1 specifies that the device 400 be activated for 30 seconds, at 2200 RPM, with an amplitude of "1", a force of "3", and a temperature of 29° C. Step 3 specifies that the dampener attachment 628 be used, and that the device 400 is to be operated using grip 1. Step 3 therefore requires that the small ball attachment in Step 2 be replaced by the dampener attachment, but specifies that the same grip is to be used.

At Step 4, Protocol 1 specifies that the device 400 be activated for 45 seconds, at 2400 RPM, with an amplitude of "4", a force of "2", and a temperature of 32° C. Step 3 specifies that the large ball attachment be used, and that the device 400 is to be operated using grip 1. Step 3 therefore requires that the dampener attachment in Step 2 be replaced by the large ball attachment, but specifies that the same grip is to be used. It will be appreciated that Protocol 1 is provided as an example to the reader of many of the different outputs that can be changed during a myriad of treatment protocols that can be provided or developed. It will be further appreciated that any one or more of the outputs can be a part of a protocol or routine and any of the outputs discussed herein can be omitted. For example, a protocol may only include time and speed or only time speed and force, or only time, speed and grip or any other combination of the outputs described herein.

FIG. 45 is a table showing an example of a "Shin Splints" protocol in accordance with a preferred embodiment. Like Protocol 1, the Shin Splints protocol is divided into four steps, each depicting a specified time, speed, amplitude, attachment, force, temperature, and grip, but also specifying a particular arm position and body part to which to apply the attachment. At Step 1, the device 400 is activated for 1 minute at a speed of 1500 RPM, with an amplitude of "1", a force of "2", and a temperature of 21° C. Step 1 specifies that the dampener attachment be used, and that the device 400 is to be operated using grip 2 ("Reverse"), to the right shin.

Step 1 also specifies the arm position 632, 634, 636 to be used is arm position 1. One of ordinary skill in the art would understand that the numbers of arm position (e.g., 1, 2, 3, 4, etc.) are predetermined arm positions intended to be used during a particular protocol. The part of the body to which the attachment 628 is to be applied is one of the factors in determining an optimal arm position. The arm position, however, may be determined by the user and is not required to otherwise implement a protocol. As shown in FIG. [[39]] 38, a "standard" grip may be utilized with arm position 632 to apply to specific parts of the body. As shown in FIG. 39, a "reverse" grip may be utilized with arm position 634 to apply to specific parts of the body. As shown in FIG. 40, a "base" grip may be utilized with arm position 636 to apply to specific parts of the body. One of ordinary skill in the art would recognize that the arm position 632, 634, 636 in combination with the particular grip 143, 145, 147 may vary depending on the application. One of ordinary skill in the art will understand that setting the arm position of a device 400 depends upon the specific device. For example, certain devices may allow a user to adjust arm position while others do not. For those that do not, this step does not apply. In other embodiments, this step may be performed during execution of the steps of the particular protocol.

At Step 2, the Shin Splints protocol specifies that the device 400 be activated for 1 minute at 1500 RPM, with an amplitude of "1", a force of "2", and a temperature of 21° C. Step 2 specifies that the dampener attachment be used, and that the device 400 is to be operated using grip 2 ("Reverse"), at an arm position 1, to the left shin. Step 2 therefore uses the same attachment, grip, and arm position as Step 1, but is applied to the other shin.

At Step 3, the Shin Splints protocol specifies that the device 400 be activated for 1 minute at 2000 RPM, with an amplitude of "3", a force of "3", and a temperature of 24° C. Step 2 specifies that the dampener attachment be used, and that the device 400 is to be operated using grip 3 ("Base"), at an arm position 1, to the right calf Step 3 therefore requires that the user change grips from "reverse" to "base" grips, but specifies that the same attachment and arm position be used.

At Step 4, the Shin Splints protocol specifies that the device 400 be activated for 1 minute at 2000 RPM, with an amplitude of "3", a force of "3", and a temperature of 24° C. Step 2 specifies that the dampener attachment be used, and that the device 400 is to be operated using grip 3 ("Base"), at an arm position 1, to the left calf Step 2 therefore uses the same attachment, grip, and arm position as Step 1, but is applied to the other calf.

FIG. 46 is a series of flow diagrams (FIGS. 46A, 46B, 46C) showing a method 1500 of executing a routine for a percussive massage device.

Figure 46A:
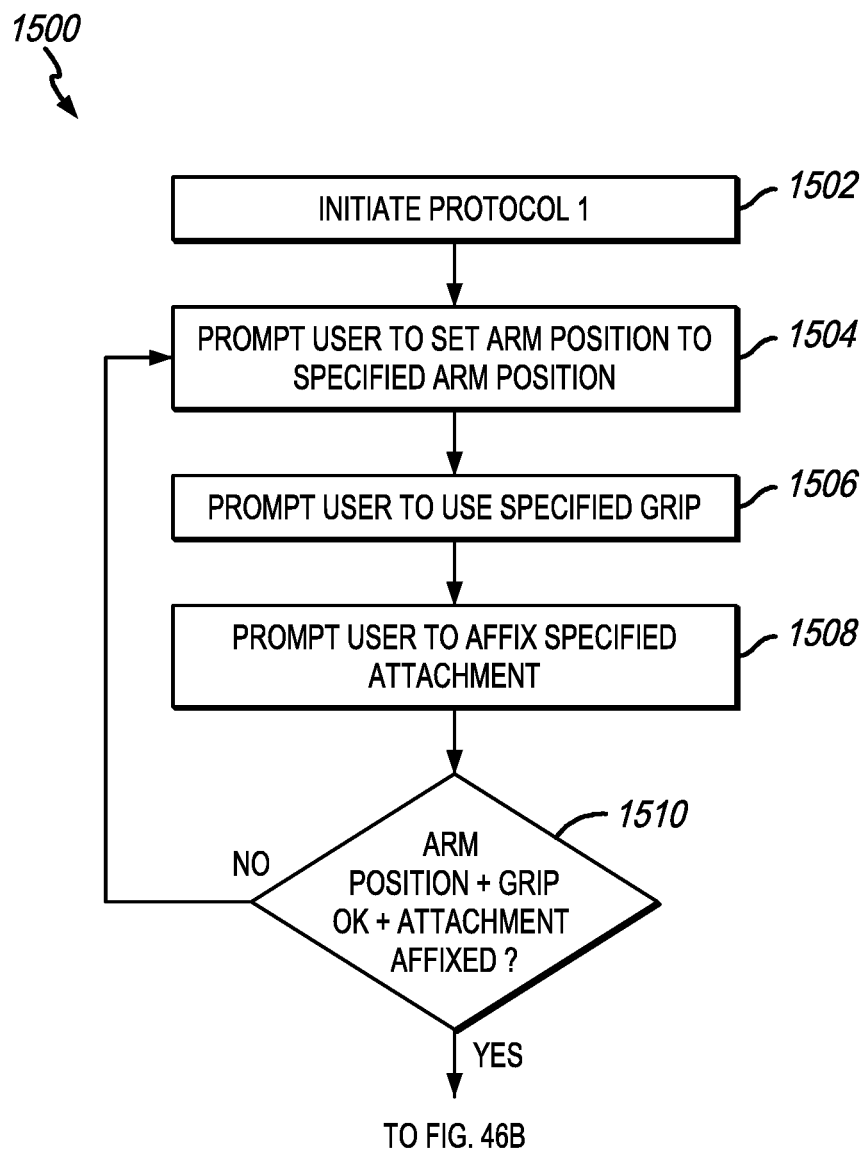
FIGS. 46A, 46B, 46C, and 46D are methods of performing a routine for a percussive massage device.

FIG. 46A is a flow diagram showing an exemplary protocol initiation. At Step 1502, Protocol 1 is initiated. Protocol 1, for example, is the Protocol 1 depicted in FIG. 44 or the "Shin Splints" Protocol depicted in FIG. 45. One of ordinary skill in the art would understand that Protocol 1 depicted in FIG. 44 does not include all of the outputs that are specified in the Shin Splints Protocol depicted in FIG. 45, and thus, not all steps of the method 1500 apply to the Protocol 1 depicted in FIG. 44.

At Step 1504, a user is prompted to set the arm position to the specified arm position 632, 634, 636. The user may be the person using the device 400 on their own body or on the body of another person. The arm position 632, 634, 636 specified in the Shin Splints Protocol is arm position 1, for example.

At Step 1506, the user is prompted to use a specified grip or handle portion 143, 145, 147 on the device 400. The grip specified in the Shin Splints Protocol is the third handle portion 147, for example. As described herein, the grip may vary depending on the particular protocol or step.

At Step 1508, the user is prompted to affix a specified attachment to the device 400. As described herein, the attachment may vary depending on the particular protocol or step.

At Step 1510, the method determines whether the arm position 632, 634, 636 and the grip position 143, 145, 147 are configured appropriately and whether the attachment 628 is affixed. Step 1510 may involve a prompt to the user by haptic feedback, application interface, or touch screen (among other types of prompts) in which the user is asked to proceed when the appropriate arm position, grip, and attachment are ready. In other embodiments, the device 400 may sense that the arm position and grip are appropriate and that an attachment is affixed before proceeding automatically. In an embodiment, Step 1510 is repeated until the arm position, grip, and attachment are ready.

Figure 46B:
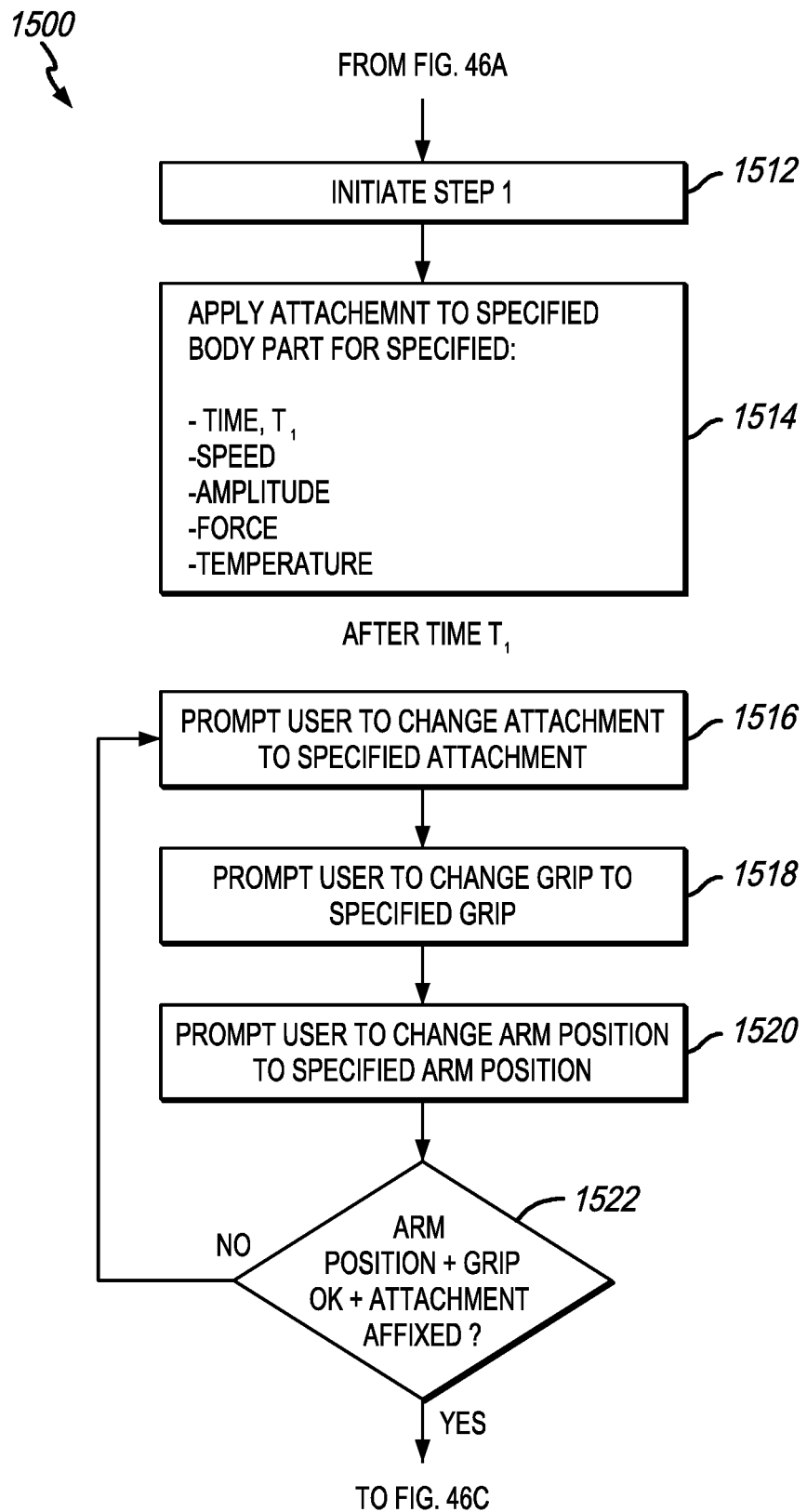

FIG. 46B is a flow diagram showing an exemplary Step 1 of the protocol, continuing the method 1500 where FIG. 46A left off.

At Step 1512, Step 1 of the protocol is initiated. Step 1, for example, is Step 1 depicted in FIGS. 44 and 45, for example.

At Step 1514, the method 1500 applies a specified time period ($T_1$) in which the device 400 is activated, a speed of the attachment, an amplitude of the attachment, a force of the attachment, and a temperature of the attachment. In an embodiment, one or more of these outputs of the device 400 are applied. These outputs may be applied by the routine controller 630. One of ordinary skill in the art would understand that a user's implementation of the device 400 on a body part is not required to apply certain of these outputs. For example, the time period, speed, amplitude, and temperature are not necessarily dependent upon a user applying pressure to a body part. On the other hand, the force applied by the attachment 628 may require a user to exert pressure on a body part for a target force (or a target force range) to be reached. Further, the temperature may vary depending on whether the attachment 628 is applied to a body part, or not, and to which body part it is applied. Thus, the temperature may need to be adjusted during application of the attachment 628 to reach a desired temperature predetermined by the protocol. In another embodiment, the temperature may be adjusted by a user.

After time period $T_1$, the user may be prompted to change the attachment 628, arm position 632, 634, 636, and/or grip position 143, 145, 147. These outputs may need to be implemented prior to the start of Step 2 of a protocol. In the Shin Splints Protocol depicted in FIG. 45, the attachment 628, arm position 632, 634, 636 and grip position 143, 145, 147 remain the same. At Step 1516, after time period $T_1$, the user is prompted to set the arm position to the specified arm position 632, 634, 636. The user may be the person using the device 400 on their own body or on the body of another person.

At Step 1518, the user is prompted to use a specified grip 143, 145, 147 on the device 400. As described herein, the grip may vary depending on the particular protocol or step.

At Step 1520, the user is prompted to affix a specified attachment 628 to the device 400. As described herein, the attachment 628 may vary depending on the particular protocol or step.

At Step 1522, the method determines whether the arm position 632, 634, 636 and the grip position 143, 145, 147 are configured appropriately and whether the attachment 628 is affixed. This step and all other like steps are optional. Step 1510 may involve a prompt to the user by haptic feedback, application interface, or touch screen (among other types of prompts) in which the user is prompted to move to the next step in the routine and/or requested to proceed when the appropriate arm position, grip, and attachment are ready. In other embodiments, the device 400 may sense that the arm position and grip are appropriate and that an attachment is affixed before proceeding automatically. In an embodiment, Step 1522 is repeated until the arm position, grip, and attachment are ready.

Figure 46C:
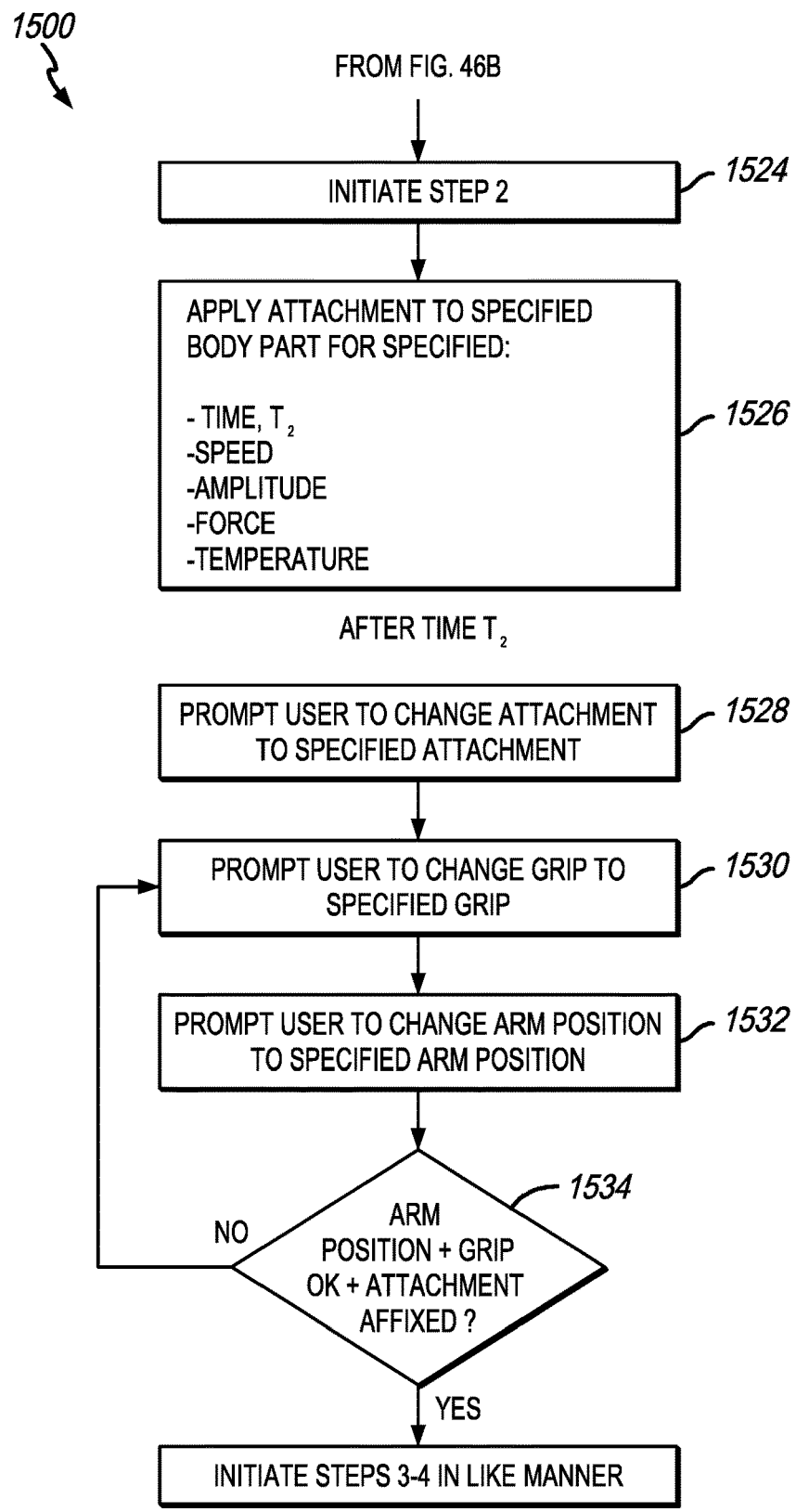

FIG. 46C is a flow diagram showing an exemplary Step 2 of the protocol, continuing the method 1500 where FIG. 46B left off.

At Step 1524, Step 2 of the protocol is initiated. Step 2, for example, is Step 2 depicted in FIGS. 44 and 45, for example.

At Step 1526, the method 1500 applies a specified time period ($T_2$) in which the device 400 is activated, a speed of the attachment, an amplitude of the attachment, a force of the attachment, and a temperature of the attachment. In an embodiment, one or more of these outputs of the device 400 are applied. These outputs may be applied by the routine controller 630. One of ordinary skill in the art would understand that a user's implementation of the device 400 on a body part is not required to apply certain of these outputs. For example, the time period, speed, amplitude, and temperature are not necessarily dependent upon a user applying pressure to a body part. On the other hand, the force applied by the attachment 628 may require a user to exert pressure on a body part for a target force to be reached. Further, the temperature may vary depending on whether the attachment 628 is applied to a body part, or not, and to which body part it is applied. Thus, the temperature may need to be adjusted during application of the attachment 628 to reach a desired temperature predetermined by the protocol. In another embodiment, the temperature may be adjusted by a user.

After time period $T_2$, the user may be prompted to change the attachment 628, arm position 632, 634, 636, and/or grip position 143, 145, 147. These outputs may need to be implemented prior to the start of Step 3 of a protocol. In the Shin Splints Protocol depicted in FIG. 45, the attachment 628 and arm position 632, 634, 636 remain the same, but the grip 143, 145, 147 is adjusted to the base grip. At Step 1528, after time period $T_2$, the user is prompted to set the arm position to the specified arm position 632, 634, 636. The user may be the person using the device 400 on their own body or on the body of another person.

At Steps 1528-1534, therefore, steps substantially the same as Steps 1516-1522 are performed. After Step 1534, Steps 3-4 are initiated in substantially the same manner as Steps 1-2. For example, Steps 3 and 4 may be Steps 3 and 4 of the Protocol 1 depicted in FIG. 44 or the Shin Splints Protocol depicted in FIG. 45. Furthermore, Step 1534 can be omitted in a device where none of the grip, arm position or attachment can be sensed by the device. In this embodiment, the given protocol simply moves from step 1 to step 2 prompting the user to make a change (but regardless of whether the user has actually made a change).

Figure 46D:
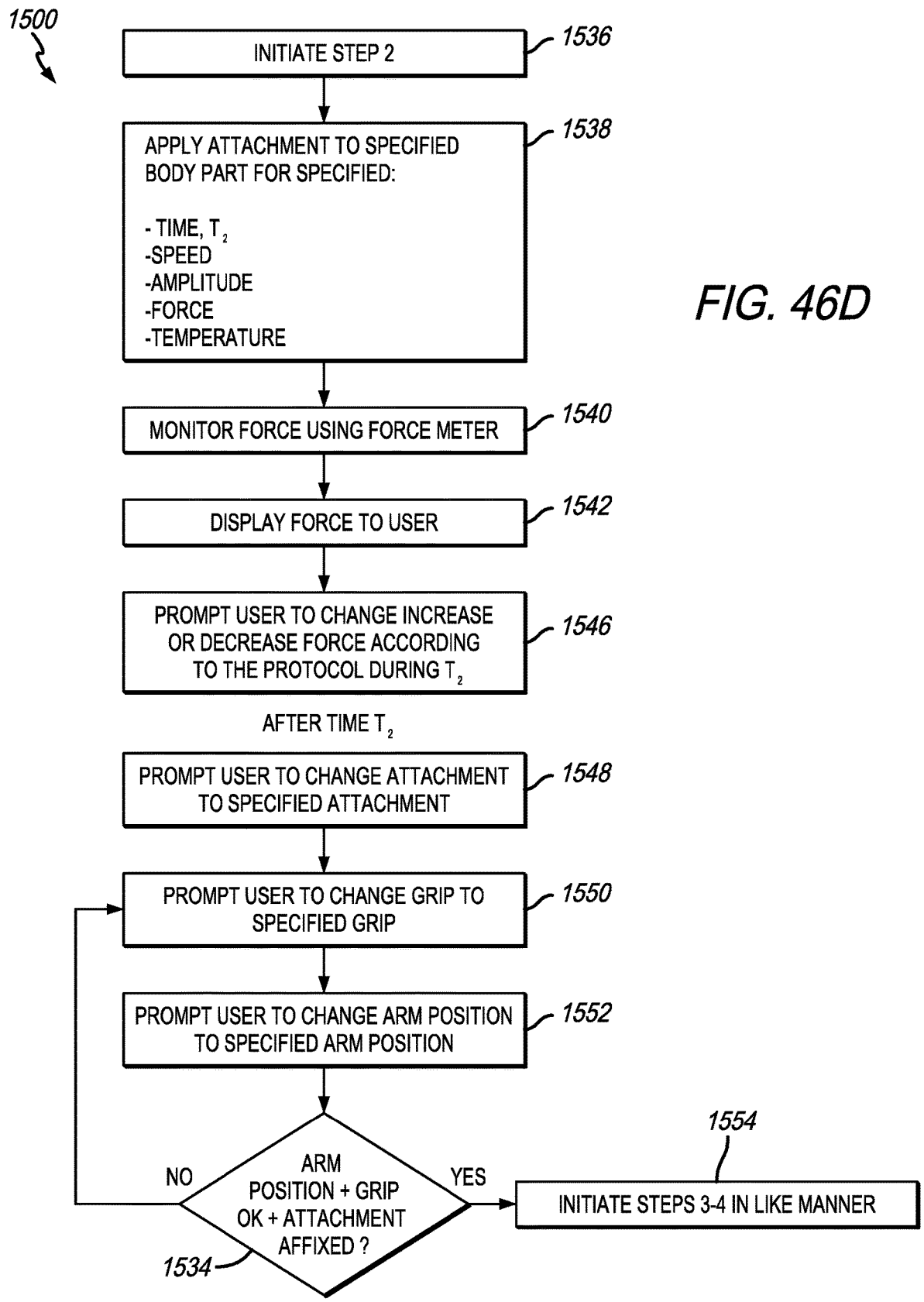

As an alternative to FIG. 46C, FIG. 46D is a flow diagram depicting an alternative Step 2 of a protocol. In the alternative Step 2, a force meter adjustment is implemented.

Steps 1536-1538 are performed substantially the same as Steps 1524-1526 in previous Step 2 above.

At Step 1540, the force being applied by the attachment 628 is monitored. In the embodiment shown in FIG. 46D, the method 1500 utilizes the force meter 400 to monitor the force actually being applied by the user.

At Step 1542, the force is displayed to the user. In an embodiment, the force is displayed on an application interface 1584 such as a graphical user interface. In other embodiments, individual use or combined use of the application interface 1584, touch screen 1582, the OLED screen 711, or the like, may be used to display the force.

Figure 48:
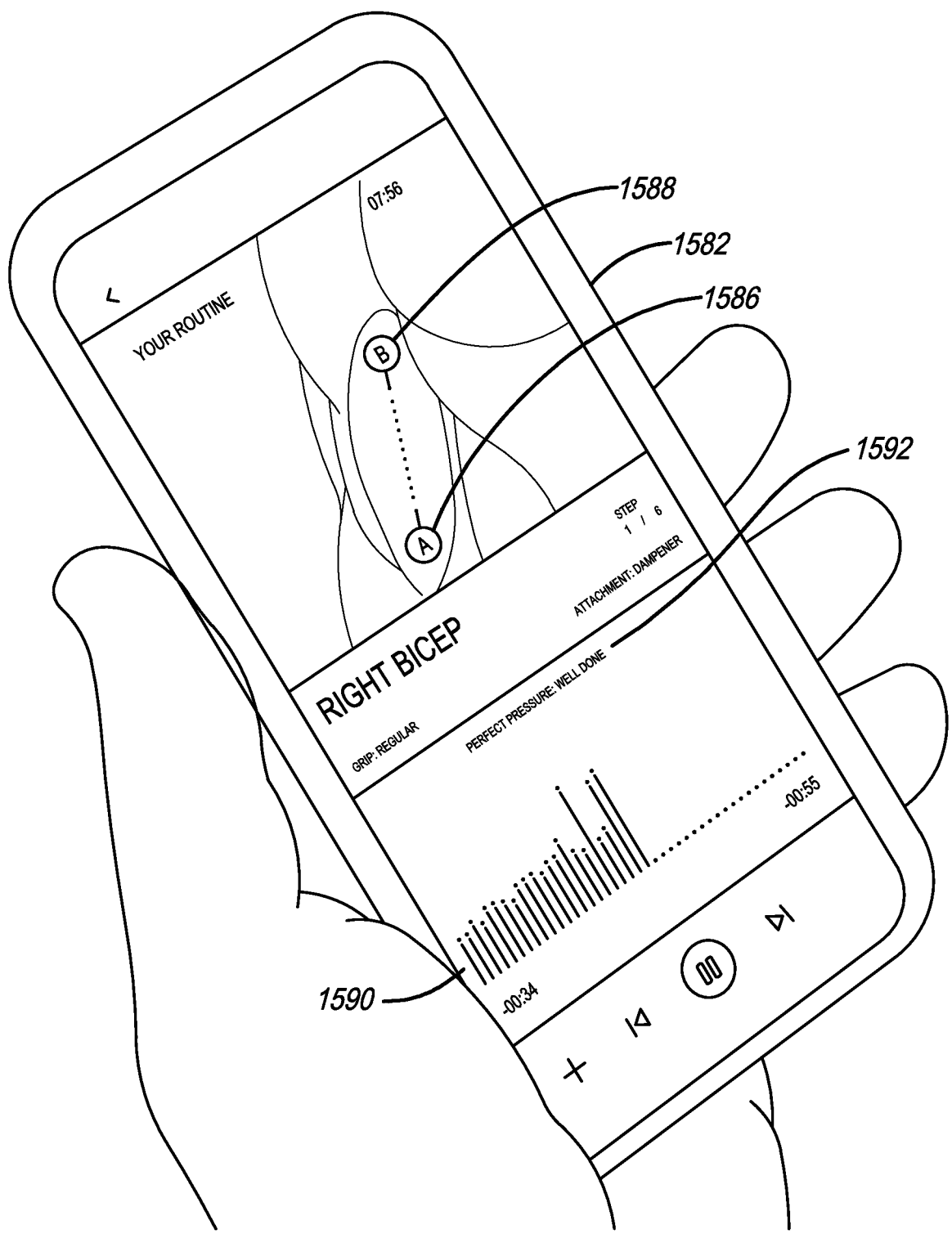
FIG. 48 is a front view of a graphical user interface showing a "Right Bicep" protocol.

At Step 1546, the user is prompted to increase or decrease the force being applied to a body part according to the specified protocol during $T_2$. FIG. 48 is a diagram showing a touch screen 1582 in accordance with an exemplary embodiment of the display of the force. A force display 1590 shows an exemplary embodiment of Step 1546. The force display 1590 shows a series of force measurements over the course of the "Right Bicep" step of a protocol. A force display prompt 1592 is used to display a message to the user such as "PERFECT PRESSURE: WELL DONE" when the force applied by the attachment 628 matches or corresponds to a target force predetermined by the protocol. In this embodiment, the force display prompt 1592 may recite "INCREASE PRESSURE" or the like if the measured force applied by the attachment 628 is lower than the target force predetermined by the protocol. Consequently, if the measured force applied by the attachment 628 is higher than the target force predetermined by the protocol, then the force display prompt 1592 may recite "DECREASE PRESSURE" or the like. The user may then adjust the pressure the user is exerting on the body part to either increase pressure or decrease pressure according to the force display prompt 1592 so that the measured force is equivalent or substantially equivalent to the target force.

After time period $T_2$, the user may be prompted to change the attachment 628, arm position 632, 634, 636, and/or grip position 143, 145, 147. These outputs may need to be implemented prior to the start of Step 3 of a protocol. In the Shin Splints Protocol depicted in FIG. 45, the attachment 628 and arm position 632, 634, 636 remain the same, but the grip 143, 145, 147 is adjusted to the base grip. At Step 1528, after time period $T_2$, the user is prompted to set the arm position to the specified arm position 632, 634, 636. The user may be the person using the device 400 on their own body or on the body of another person.

At Steps 1548-1552, therefore, steps substantially the same as Steps 1516-1522 are performed. After Step 1534, Steps 3-4 are initiated in substantially the same manner as Steps 1-2. For example, Steps 3 and 4 may be Steps 3 and 4 of the Protocol 1 depicted in FIG. 44 or the Shin Splints Protocol depicted in FIG. 45.

Figure 47:
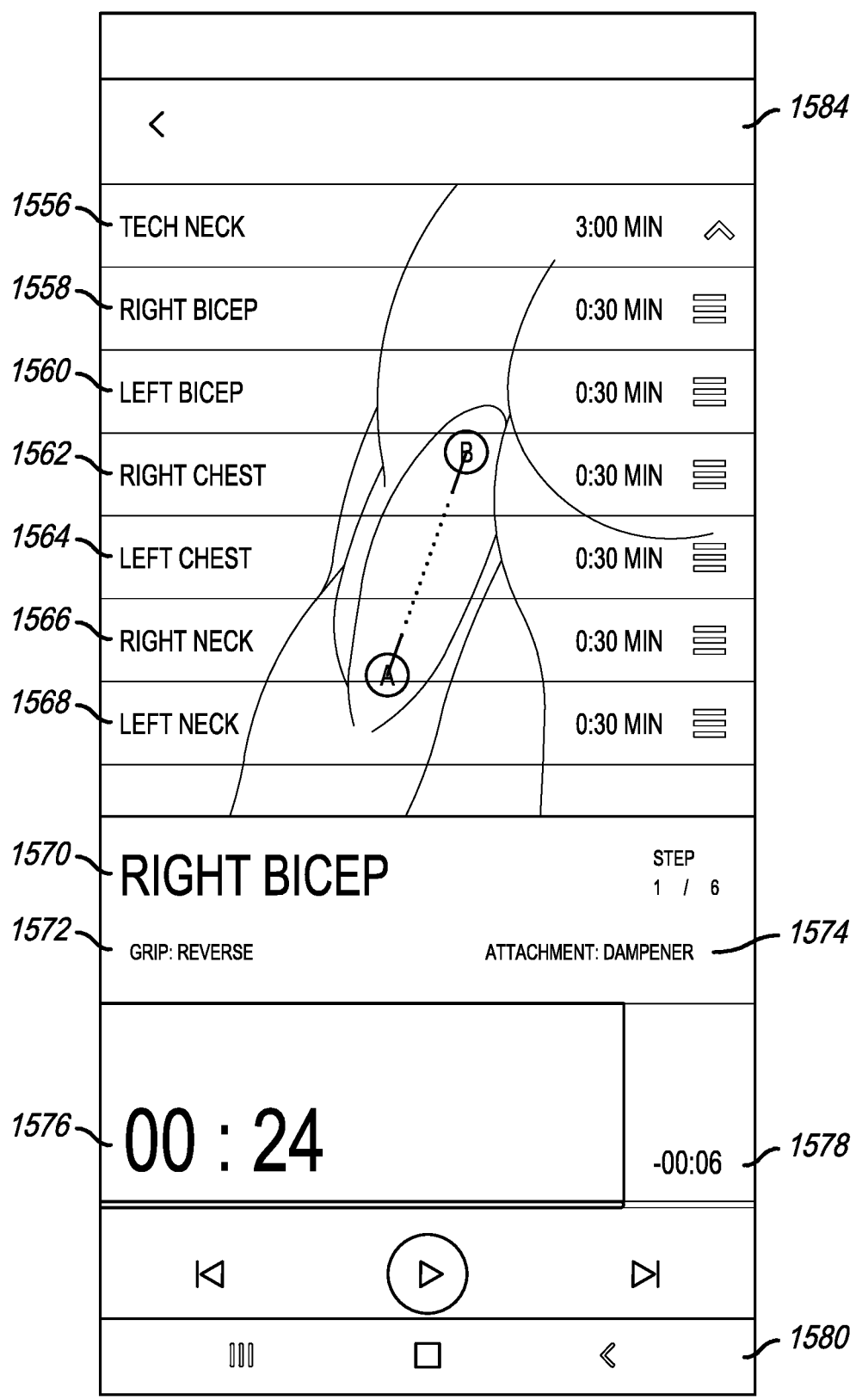
FIG. 47 is a front view of a graphical user interface showing a "Tech Neck" protocol.

FIG. 47 is a diagram in accordance with an exemplary embodiment of an application interface 1584. At the top of the interface 1584, a protocol field 1556 is displayed to the user. In this embodiment, the protocol field 1556 is "TECH NECK." The protocol title 1556 also shows the overall time period of the protocol.

The next portion of the interface 1584 shows step fields 1558-1568 of the protocol that are displayed to the user. In this embodiment, the step fields identify the title of the step and time period of the step. For example, step field 1558 is titled "RIGHT BICEP" (where the treatment will be provided) and the time period of activation is "0:30 MIN."

The interface 1584 also includes a current step field 1570 that identifies the current step title 1570, a grip title display 1572, and an attachment title display 1574.

The interface 1584 also includes a time display 1576 and a time remaining display 1578 to show the user how much time has occurred during that step and the time remaining in that step. Finally, the interface 1584 includes a control field 1580 to play, skip back, and skip forward from step to step.

As described above, FIG. 47 shows a touch screen 1582 on a mobile device. The touch screen 1582 displays a graphic depicting a starting point 1586 "A" and an end point 1588 "B" (thereby defining a treatment path) showing the user where to apply the attachment 628 to the specified body part. In FIG. 47, the display instructs the user to move the attachment from the lower portion of the right bicep to the upper portion of the right bicep (the treatment path) during the current step. In some embodiments, during a single step, the user may be prompted or shown on the graphical user interface more than one treatment path (or a first treatment path and a second treatment path) on the same body part/muscle or on different body parts/muscles. For example, during the right bicep step, the user may be prompted to first move the device along the path shown in FIG. 47, but, during the same 30 second step may also be prompted or shown a path that is parallel to the path shown in FIG. 47.

Although the operations of the method(s) herein are shown and described in a particular order, the order of the operations of each method may be altered so that certain operations may be performed in an inverse order or so that certain operations may be performed, at least in part, concurrently with other operations. In another embodiment, instructions or sub-operations of distinct operations may be implemented in an intermittent and/or alternating manner.

Unless the context clearly requires otherwise, throughout the description and the claims, the words "comprise," "comprising," and the like are to be construed in an inclusive sense, as opposed to an exclusive or exhaustive sense; that is to say, in the sense of "including, but not limited to." As used herein, the terms "connected," "coupled," or any variant thereof, means any connection or coupling, either direct or indirect, between two or more elements; the coupling of connection between the elements can be physical, logical, or a combination thereof. Additionally, the words "herein," "above," "below," and words of similar import, when used in this application, shall refer to this application as a whole and not to any particular portions of this application. Where the context permits, words in the above Detailed Description of the Preferred Embodiments using the singular or plural number may also include the plural or singular number respectively. The word "or" in reference to a list of two or more items, covers all of the following interpretations of the word: any of the items in the list, all of the items in the list, and any combination of the items in the list.

Embodiments are envisioned where any of the aspects, features, component or steps herein may be omitted and/or are option. Furthermore, where appropriate any of these optional aspects, features, component or steps discussed herein in relation to one aspect of the invention may be applied to another aspect of the invention.

The above-detailed description of embodiments of the disclosure is not intended to be exhaustive or to limit the teachings to the precise form disclosed above. While specific embodiments of and examples for the disclosure are described above for illustrative purposes, various equivalent modifications are possible within the scope of the disclosure, as those skilled in the relevant art will recognize. For example, while processes or blocks are presented in a given order, alternative embodiments may perform routines having steps, or employ systems having blocks, in a different order, and some processes or blocks may be deleted, moved, added, subdivided, combined, and/or modified to provide alternative or subcombinations. Each of these processes or blocks may be implemented in a variety of different ways. Also, while processes or blocks are at times shown as being performed in series, these processes or blocks may instead be performed in parallel, or may be performed, at different times. Further any specific numbers noted herein are only examples: alternative implementations may employ differing values or ranges.

The above-detailed description of embodiments of the disclosure is not intended to be exhaustive or to limit the teachings to the precise form disclosed above. While specific embodiments of and examples for the disclosure are described above for illustrative purposes, various equivalent modifications are possible within the scope of the disclosure, as those skilled in the relevant art will recognize. Further, any specific numbers noted herein are only examples: alternative implementations may employ differing values, measurements or ranges. It will be appreciated that any dimensions given herein are only exemplary and that none of the dimensions or descriptions are limiting on the present invention.

The teachings of the disclosure provided herein can be applied to other systems, not necessarily the system described above. The elements and acts of the various embodiments described above can be combined to provide further embodiments.

Any patents and applications and other references noted above, including any that may be listed in accompanying filing papers, are incorporated herein by reference in their entirety. Aspects of the disclosure can be modified, if necessary, to employ the systems, functions, and concepts of the various references described above to provide yet further embodiments of the disclosure.

These and other changes can be made to the disclosure in light of the above Detailed Description of the Preferred Embodiments. While the above description describes certain embodiments of the disclosure, and describes the best mode contemplated, no matter how detailed the above appears in text, the teachings can be practiced in many ways. Details of the system may vary considerably in its implementation details, while still being encompassed by the subject matter disclosed herein. As noted above, particular terminology used when describing certain features or aspects of the disclosure should not be taken to imply that the terminology is being redefined herein to be restricted to any specific characteristics, features or aspects of the disclosure with which that terminology is associated. In general, the terms used in the following claims should not be construed to limit the disclosures to the specific embodiments disclosed in the specification unless the above Detailed Description of the Preferred Embodiments section explicitly defines such terms. Accordingly, the actual scope of the disclosure encompasses not only the disclosed embodiments, but also all equivalent ways of practicing or implementing the disclosure under the claims.

While certain aspects of the disclosure are presented below in certain claim forms, the inventors contemplate the various aspects of the disclosure in any number of claim forms. For example, while only one aspect of the disclosure is recited as a means-plus-function claim under 35 U.S.C. § 112, ¶6, other aspects may likewise be embodied as a means-plus-function claim, or in other forms, such as being embodied in a computer-readable medium. (Any claims intended to be treated under 35 U.S.C. § 112, ¶6 will begin with the words "means for"). Accordingly, the applicant reserves the right to add additional claims after filing the application to pursue such additional claim forms for other aspects of the disclosure.

Accordingly, although exemplary embodiments of the invention have been shown and described, it is to be understood that all the terms used herein are descriptive rather than limiting, and that many changes, modifications, and substitutions may be made by one having ordinary skill in the art without departing from the spirit and scope of the invention.

What is claimed is:

1. A percussive therapy device comprising:
   a housing, wherein the housing includes first, second and third handle portions and a head portion that cooperate to define a handle opening, wherein the first handle portion defines a first axis, the second handle portion defines a second axis and the third handle portion defines a third axis, wherein the first, second and third axes cooperate to form a triangle, such that a user can grasp any of the first, second or third handle portions independently to use the percussive therapy device,
   an electrical source,
   a motor positioned in the head portion of the housing,
   a switch for activating the motor, and
   a push rod assembly operatively connected to the motor and configured to reciprocate in response to activation of the motor.

2. The percussive therapy device of claim 1 wherein at least a portion of the push rod assembly extends outside of the head portion.

3. The percussive therapy device of claim 1 wherein the first handle portion is generally straight, wherein the second handle portion is generally straight, and wherein the third handle portion is generally straight.

4. The percussive therapy device of claim 1 further comprising a wireless connection device.

5. The percussive therapy device of claim 1 wherein the electrical source is a rechargeable battery, and wherein the percussive massage device further comprising a wireless charging receiver that is in electrical communication with the battery.

6. The percussive therapy device of claim 1 further comprising a touchscreen.

7. The percussive therapy device of claim 1 wherein the electrical source is a battery that is positioned in the second handle portion, and wherein a wireless charging receiver that is in electrical communication with the battery is positioned in the third handle portion.

8. The percussive therapy device of claim 1 wherein the percussive therapy device is configured to provide haptic feedback.

9. The percussive therapy device of claim 1 wherein the first handle portion includes a first handle portion interior edge and defines a first handle portion length, wherein the first handle portion length is long enough that when a user grasps the first handle portion with a hand at least a portion of three fingers extend through the handle opening and contact the first handle portion interior edge, wherein the second handle portion includes a second handle portion interior edge and defines a second handle portion length, wherein the second handle portion length is long enough that when a user grasps the second handle portion with a hand at least a portion of three fingers extend through the handle opening and contact the second handle portion interior edge, wherein the third handle portion includes a third handle portion interior edge and defines a third handle portion length, wherein the third handle portion length is long enough that when a user grasps the third handle portion with a hand at least a portion of three fingers extend through the handle opening and contact the third handle portion interior edge.

10. The percussive therapy device of claim 9 wherein at least two of the first handle portion, second handle portion and third handle portion are generally straight.

11. The percussive therapy device of claim 10 further comprising a fourth interior surface that at least partially defines the handle opening, wherein the first handle portion interior surface, second handle portion interior surface, third handle portion interior surface and fourth interior surface cooperate to define a quadrilateral.

12. A percussive therapy device comprising:
    a housing,
    an electrical source,
    a motor positioned in the housing, wherein the motor is a brushless motor,
    a motor mount positioned in the housing, wherein the motor mount includes a first side wall that includes opposing inner and outer major surfaces, and a second side wall that includes opposing inner and outer major surfaces, wherein a motor mount interior is defined between the inner major surfaces of the first and second side walls, wherein the motor is secured to the outer major surface of the first side wall and the second side wall is secured to the housing, wherein the first side wall defines a first side wall axis, wherein the motor includes a motor shaft that defines a motor shaft axis and extends through a protrusion opening defined in the first side wall of the motor mount and into the motor mount interior, wherein the motor shaft axis extends parallel to the first side wall axis, wherein the first side wall axis is normal to the outer major surface of the first side wall,
    a switch for activating the motor, and
    a push rod assembly operatively connected to the motor and configured to reciprocate in response to activation of the motor, wherein at least a portion of the push rod assembly is positioned in the motor mount interior.

13. The percussive therapy device of claim 12 wherein the push rod assembly extends through a push rod opening defined in the motor mount and out of the motor mount interior, and wherein the push rod assembly extends in a direction perpendicular to the motor shaft.

14. The percussive therapy device of claim 12 wherein the first side wall includes at least a first flange extending outwardly therefrom, wherein the first flange is positioned adjacent a first protrusion on the motor.

15. The percussive therapy device of claim 14 wherein the first side wall includes second and third flanges extending outwardly therefrom, wherein the second and third flanges are positioned adjacent second and third protrusions on the motor.

16. A method of using a percussive massage device, the method comprising the steps of:
obtaining the percussive massage device, wherein the percussive massage device includes a housing that includes first, second and third handle portions that cooperate to at least partially define a handle opening, an electrical source, a motor positioned in the housing, a switch for activating the motor, and a push rod assembly operatively connected to the motor and configured to reciprocate in response to activation of the motor, wherein the first handle portion defines a first axis, the second handle portion defines a second axis and the third handle portion defines a third axis, wherein the first handle portion includes a first handle portion interior edge and defines a first handle portion length, wherein the first handle portion length is long enough that when a user grasps the first handle portion with a hand at least a portion of three fingers extend through the handle opening and contact the first handle portion interior edge, wherein the second handle portion includes a second handle portion interior edge and defines a second handle portion length, wherein the second handle portion length is long enough that when a user grasps the second handle portion with a hand at least a portion of three fingers extend through the handle opening and contact the second handle portion interior edge, wherein the third handle portion includes a third handle portion interior edge and defines a third handle portion length, wherein the third handle portion length is long enough that when a user grasps the third handle portion with a hand at least a portion of three fingers extend through the handle opening and contact the third handle portion interior edge,
activating the motor using the switch,
grasping the first handle portion using a first hand,
massaging a first body part,
reorienting the percussive massage device, grasping the second handle portion using the first hand and massaging the first body part or a second body part, and
reorienting the percussive massage device, grasping the third handle portion using the first hand and massaging the first body part, the second body part or a third body part.

17. The method of claim 16 wherein the housing includes a head portion, and wherein the motor is positioned in the head portion.

18. The method of claim 16 wherein at least two of the first handle portion, second handle portion and third handle portion are generally straight.

19. The method of claim 16 wherein the first handle portion, second handle portion and third handle portion are generally straight.

20. The method of claim 16 wherein the housing defines a housing length, wherein at least a portion of the handle opening extends forwardly of half the housing length.

21. The method of claim 16 wherein a transverse plane that bifurcates the housing extends through the handle opening.

22. The method of claim 16 further comprising a fourth interior surface that at least partially defines the handle opening, wherein the first handle portion interior surface, second handle portion interior surface, third handle portion interior surface and fourth interior surface cooperate to define a quadrilateral.

23. A percussive therapy device comprising:
a housing,
an electrical source,
a motor positioned in the housing, wherein the motor is a brushless motor,
a motor mount positioned in the housing, wherein the motor mount includes a first side wall that includes opposing inner and outer major surfaces, and a second side wall that includes opposing inner and outer major surfaces, wherein a motor mount interior is defined between the inner major surfaces of the first and second side walls, and wherein the motor is directly secured to the outer major surface of the first side wall and wherein the second side wall is secured to the housing,
a switch for activating the motor, and
a push rod assembly operatively connected to the motor and configured to reciprocate in response to activation of the motor.

* * * * *